United States Patent [19]

Donahue et al.

[11] Patent Number: 5,359,047

[45] Date of Patent: Oct. 25, 1994

[54] NUCLEIC ACIDS ENCODING DNA STRUCTURE-SPECIFIC RECOGNITION PROTEIN AND USES THEREFOR

[75] Inventors: Brian A. Donahue, Menlo Park, Calif.; Jeffrey H. Toney, Westfield, N.J.; John M. Essigmann, Brookline, Mass.; Stephen J. Lippard, Cambridge, Mass.; Pieter M. Pil, Cambridge, Mass.; Suzanne L. Bruhn, Cambridge, Mass.; Steven J. Brown, Cambridge, Mass.; Patti J. Kellett, Cincinnati, Ohio

[73] Assignee: Massachusetts Institute of Technology, Cambridge, Mass.

[21] Appl. No.: 814,964

[22] Filed: Dec. 26, 1991

Related U.S. Application Data

[63] Continuation-in-part of Ser. No. 539,906, Jun. 18, 1990, abandoned, which is a continuation-in-part of Ser. No. 410,981, Sep. 22, 1989, abandoned, which is a continuation-in-part of Ser. No. 247,774, Sep. 22, 1988, abandoned.

[51] Int. Cl.$^5$ .............................................. C17N 5/12
[52] U.S. Cl. ................................ 536/23.5; 536/23.1; 435/6; 935/3; 935/9; 935/78; 530/350
[58] Field of Search .................. 536/23.1, 23.5; 435/6; 935/3, 9, 78; 530/350

[56] References Cited

FOREIGN PATENT DOCUMENTS 0057553 8/1982 European Pat. Off. .
WO90/03396 9/1989 PCT Int'l Appl. .

OTHER PUBLICATIONS

PCT/US92/11107, International Search Report, 18 Dec. 1992.
Lenz et al. (1990), *Identification of a mammalian nuclear factor and human cDNA-encoded proteins that recognize DNA containing apurnic sites,* 87 Proc. Natl. Acad. Sci. USA 3396–3400.
Bruhn et al. (Mar. 1992), *Isolation and characterization of human cDNA clones encoding a high mobility group box protein that recognizes structural distortions to DNA caused by binding of the anticancer agent ciplatin,* 89 Proc. Natl. Acad. Sci. USA 2307–2311.
Donahue et al. (1990) *Characterization of a DNA damage-recognition protein from mammalian cells that binds specifically to intrastand d(GpG) and d(ApG) DNA adducts of the anticancer drug cisplatin,* 29 Biochemistry 5872–5880.
Toney et al. (Nov. 1989), *Isolation of cDNAs encoding a human protein that binds selectively to DNA modified by the anticancer drug cis-diammine-dichloroplatinum(II),* 86 Proc. Natl. Acad. Sci. USA 8328–8332.
Andrews and Jones (1991), *Characterization of binding proteins from ovarian carcinoma and kidney tubule cells that are specific for cisplatin modified DNA,* 3 Cancer Communications (No. 1) 1–10.
Paonessa et al. (1987), 15 Nucl. Acids Res. (No. 21) 9077.
Lee et al. (1987) 15 Nucl. Acids Res. (No. 13) 5051–5067.
Singh et al. (Feb. 12, 1988), 52 Cell 415–423.
Wen et al. (1989), 17 Nucl. Acids Res. (No. 3) 1197–1214.
Andrews and Jones (1991), 3 Cancer Comm. (No. 1) 1–10.
Chao et al. (1991), 277 Biochem J. 875–878.

(List continued on next page.)

Primary Examiner—Robert J. Hill, Jr.
Assistant Examiner—Shelly Guest Cermak
Attorney, Agent, or Firm—Testa, Hurwitz & Thibeault

[57] ABSTRACT

DNA structure specific recognition protein of eukaryotic origin and DNA encoding such a factor, as well as probes specific for DNA structure specific recognition protein or DNA encoding it and methods of detecting DNA structure specific recognition protein in eukaryotic cells. In particular, a mammalian cellular factor that selectively recognizes and binds DNA damaged or modified by a drug (the anticancer drug, cis-diamminedichloroplatinum (II) or cisplatin) has been identified.

9 Claims, 16 Drawing Sheets

OTHER PUBLICATIONS

Shirikata et al. (Sep. 1991), 11 Mol. Cell. Biol. (No. 9) 4528–4536.

Diffley and Stillman (Sep. 1991), 88 Proc. Natl. Acad. Sci. USA 7864–7868.

Howle and Gale (1970), 19 Biochem. Pharmacol. 2757–2762.

Harder and Rosenberg (1970), 6 Int. J. Cancer 207–216.

Feldberg and Grossman (1976), 15 Biochemistry (No. 11) 2402–2408.

Deutsch and Linn (Jan. 1979), 76 Proc. Natl. Acad. Sci. USA (No. 1) 141–144.

Roberts and Thomson (1979), 22 Prog. Nucl. Acid Res. & Mol. Biol. 71–133.

Moranelli and Lieberman (Jun. 1980), 77 Proc. Natl. Acad. Sci. USA (No. 6) 3201–3205.

Tsang and Kuhnlein (1982), 697 Biochim. Biophys. Acta 202–212.

Toulmé et al. (1983), 2 EMBO. J. (No. 4) 505–510.

Kuhnlein et al. (1983), 3 Biosci. Rep. 667–674.

Germanier et al. (1984), 145 Mutations Res. 35–41.

Carew and Feldberg (1985), 13 Nucl. Acid Res. (No. 1) 303–315.

Pinto and Lippard (Jul. 1985), 82 Proc. Natl. Acad. Sci. USA 4616–4619.

Fram et al. (1985), 28 Mol. Pharmacol. 51–55.

Beck et al. (1985), 13 Nucl. Acid. Res. (No. 20) 7395–7412.

Sundquist et al. (1986), 25 Biochemistry 1520–1524.

Sherman and Lippard (1987), 87 Chem. Rev. 1153–1181.

Burnouf et al. (Jun. 1987), 84 Proc. Natl. Acad. Sci. USA 3758–3762.

E. C. Friedberg, DNA Repair, Ch. 9 (W. F. Freeman & Co. 1988).

Rice et al. (Jun. 1988), 85 Proc. Natl. Acad. Sci. USA 4158–4161.

Chu and Chang (28 Oct. 1988), 242 Science 564–567.

Jiricny et al. (Dec. 1988), 85 Proc. Natl. Acad. Sci. USA 8860–8864.

Toney et al. (Nov. 1989), 86 Proc. Natl. Acad. Sci. USA 8328–8332.

```
              cis-{Pt(NH₃)2}
cis-d(GpG)    TCTCCTTCTTGGTTCTCTTCTC
              ACAGAGGAAGAACCAAGAGAAG cis-{Pt(NH₃)2}
cis-d(ApG)    TCTCCTTCTTAGTTCTCTTCTC
              AGAGAGGAAGAATCAAGAGAAG cis-{Pt(NH₃)2}
cis-d(GpTpG)  TCTCCTTCTTGTGTCTCTTCTC
              AGAGAGGAAGAACACAGAGAAG trans-{Pt(NH₃)2}
trans-d(GpTpG) TCTCCTTCTTGTGTCTCTTCTC
               AGAGAGGAAGAACACAGAGAAG cis-{Pt(NH₃)2(N3-cytosine)}
N7-d(G)       TCTCCTTCTTCGTTCTCTTCTC
              AGAGAGGAAGAAGCAAGAGAAG
```

FIG. 7

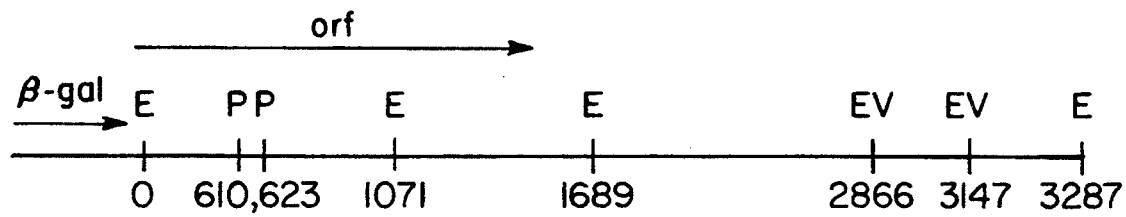

FIG. 17

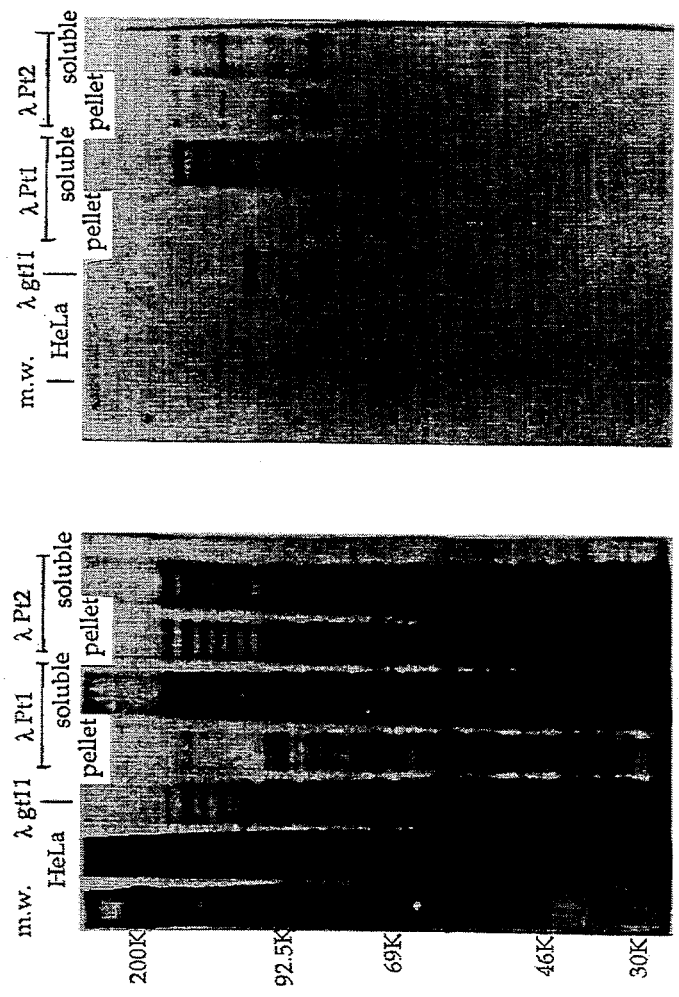

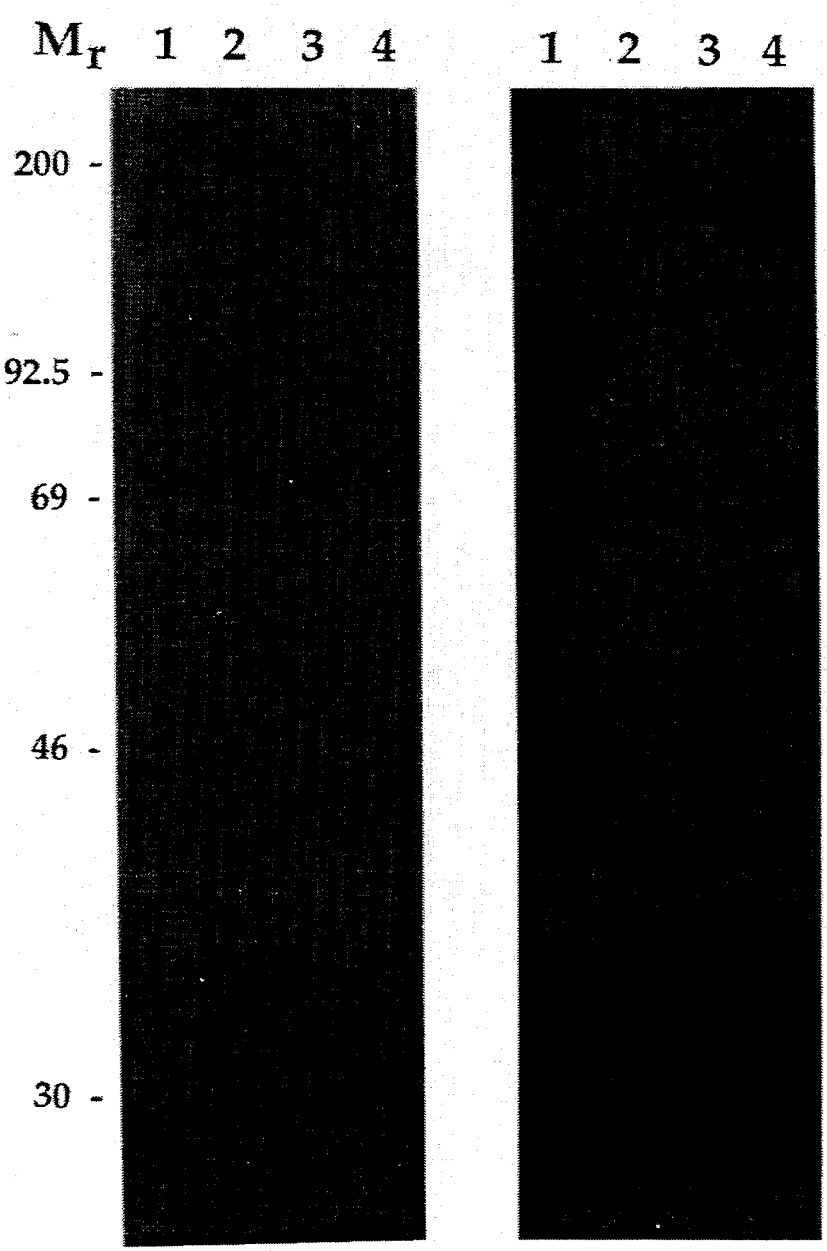

NUCLEIC ACIDS ENCODING DNA STRUCTURE-SPECIFIC RECOGNITION PROTEIN AND USES THEREFOR

FUNDING

Work described herein was supported by grants from the National Institutes of Health, a National Research Service Award, a grant from Bristol-Meyers Company and a Whitaker Health Sciences Fund predoctoral fellowship. The United States government has certain rights in the invention.

RELATED APPLICATIONS

The following is a continuation-in-part of U.S. Ser. No. 07/539,906, filed Jun. 18, 1990, now abandoned, which is a continuation-in-part of U.S. Ser. No. 07/410,981, filed Sep. 22, 1989, now abandoned, which is a continuation-in-part of U.S. Ser. No. 07/247,774, filed Sep. 22, 1988 now abandoned. The teachings of each of these documents are hereby incorporated by reference.

BACKGROUND

DNA can be damaged by a variety of environmental insults, including antitumor drugs, radiation, carcinogens, mutagens and other genotoxins. Chemical changes in the component nucleotides or of DNA secondary and tertiary structure which arise from such external causes are all considered herein to be DNA modification or damage. In addition, it is recognized that certain chemical and/or structural modifications in DNA may occur naturally, and may play a role in, for example, DNA replication, expression, or the coordinate regulation of specific genes. It has been proposed that some types of DNA modification or damage arising from external sources are similar to, or even mimic, certain types of natural DNA chemical and/or structural modification.

The mechanism(s) by or conditions under which DNA modification or damage occurs are presently unknown or poorly understood. It would be very helpful to have a better understanding of DNA damage, because DNA damage can lead to mutations and cancer, as well as cell death; the latter is exploited in chemo- and radio-therapeutics. A better understanding of DNA chemical and structural modifications, including DNA damage, would also be helpful in that it might serve as the basis for developing an enhanced ability to repair or otherwise modify the effects of such damage, leading in turn to improved organismal or suborganismal resistance to DNA damaging agents.

SUMMARY OF THE INVENTION

The present invention relates in one aspect to a DNA damage-binding factor, referred to herein as a DNA structure-specific recognition protein or SSRP; it has previously been referred to as a DNA damage recognition protein or DRP. The SSRP has been shown to bind selectively to damaged DNA in mammalian cell extracts.

In another aspect, the invention described herein relates to nucleotide sequences which encode SSRP. In still another aspect, it relates to a method of identifying SSRP in eukaryotic cells. Other aspects of the present invention relate to use of SSRP, nucleotide sequences encoding SSRP and antibodies which bind to the structure-specific recognition protein described herein.

Furthermore, this invention relates to methods of preventing or reducing damage to DNA that is the result of DNA processing (e.g., replication, recombination and repair) or is caused by contact with or exposure to a chemical compound, physical substance or other damaging agent which produces a particular, recognizable type of DNA structural damage.

The DNA structure-specific recognition protein of the present invention binds selectively to double-stranded (ds) DNA which has been structurally modified as a result of exposure to a chemical agent, such as a therapeutic agent administered for cancer therapy. Specifically, SSRP of the present invention binds selectively to ds DNA containing at least one 1,2-intrastrand dinucleotide adduct. SSRP has been shown to bind selectively to a damaged DNA fragment, by which is meant a ds DNA fragment which contains a 1,2-intrastrand dinucleotide adduct of a therapeutically active platinum compound, such as cis-diamminedichloroplatinum (II) (cis-DDP or cisplatin). As a result of selective binding of the SSRP to cisplatin-damaged DNA, a (damaged DNA fragment):(protein) complex is formed. The electrophoretic mobility of this complex is retarded, relative to the mobility of the damaged DNA fragment alone (i.e., not having SSRP bound thereto). Therefore, the complex can be electrophoretically resolved from the damaged DNA fragment alone.

cis-DDP SSRP of the present invention has been shown to bind selectively to damaged ds DNA containing the 1,2-intrastrand d(GPG) and d(ApG) dinucleotide adducts formed by cis-DDP. This binding is selective in that the SSRP does not significantly bind to single-stranded (ss) DNA, or to ds DNA lacking a 1,2-intrastrand dinucleotide adduct such as the d(ApG) and d(GpG) adducts formed by cisplatin.

The present invention also encompasses a generally applicable method of identifying other DNA structure-specific recognition proteins in eukaryotic cells, particularly those encoded by DNA which hybridizes to the DNA encoding the cis-DDP SSRP described and claimed herein. That is, this method can be used to identify other proteins having cis-DDP SSRP activity, encoded by DNA which comprises at least a region of sequence homologous to the cis-DDP SSRP gene. The present invention encompasses SSRPs identified by this method.

BRIEF DESCRIPTION OF THE DRAWINGS

FIG. 7 is an illustration of the nucleotide sequence of synthetic duplex oligonucleotides (Seq. ID Nos. 1–5) containing specific platinum adducts. The 22-base oligonucleotides containing specific platinum adducts and designated as Top strands are shown 5'→3' with their complementary bottom strands.

FIG. 8A is an autoradiograph of the results of an EMSA study showing that binding of the SSRP to the 1,2-d(GpG) dinucleotide adduct of cisplatin can be competed by cis-DDP modified DNA, but not by unmodified DNA.

FIG. 8B is an autoradiograph of the results of an EMSA study showing that binding of the SSRP to the 1,2-d(ApG) dinucleotide adduct of cisplatin can be competed by cis-DDP modified DNA, but not by unmodified DNA.

FIG. 8C is an autoradiograph of the results of an EMSA study showing that the SSRP does not bind selectively to platinated DNA containing 1,3-intrastrand dinucleotide adducts or monofunctional nucleotide adducts.

FIGS. 11A–D present the results of Western blotting and modified Western (i.e., Southwestern) blotting characterization of the proteins encoded by the λPt1 (Seq. ID No. 8) add and λPt2 (Seq. ID No. 9) clones. In each of FIGS. 11A–11D, the samples resolved in one dimension by SDS/PAGE were: lane 1, HeLa nuclei (25 μg total protein); lane 2, λgt11 lysogens; lane 3, solubilized pellet from λPt1 lysogens (the pellet was resuspended in SDS-PAGE loading bufer, then briefly sonicated); lane 4, soluble fraction from λPt1 lysogens; lane 5, solubilized pellet from λPt2 lysogens; and lane 6, soluble fraction from λPt2 lysogens.

FIG. 11A is a photograph of a blot which has been stained with India ink, and therefore shows the total protein contents of each electrophoretically resolved sample.

FIG. 11B is a photograph of a Western blot which has been probed with mouse monoclonal anti-β-galactosidase antibodies (1:50,000), followed by goat anti-mouse IgG conjugated with alkaline phosphatase (1:7500). β-galactosidase specific immune complexes were visualized using nitro blue tetrazolium and 5-bromo-4-chloro-3-indolyl phosphate.

FIG. 11C is an autoradiograph of a Southwestern blot which has been probed with radiolabelled, unmodified 422 bp DNA fragment ($1.5 \times 10^5$ cpm/mL.).

FIG. 11D is an autoradiograph of a Southwestern blot which has been probed with radiolabelled, cis-DDP-modified 422 bp DNA fragment ($r_b$=0.04 at $1.5 \times 10^5$ cpm/mL.). It shows the presence of proteins which form (damaged DNA fragment):(protein) complexes.

FIG. 17 is a schematic illustration of the positions of restriction endonuclease sites in the λyPt clone (Seq. ID No. 12).

DETAILED DESCRIPTION OF THE INVENTION

Figure 1:
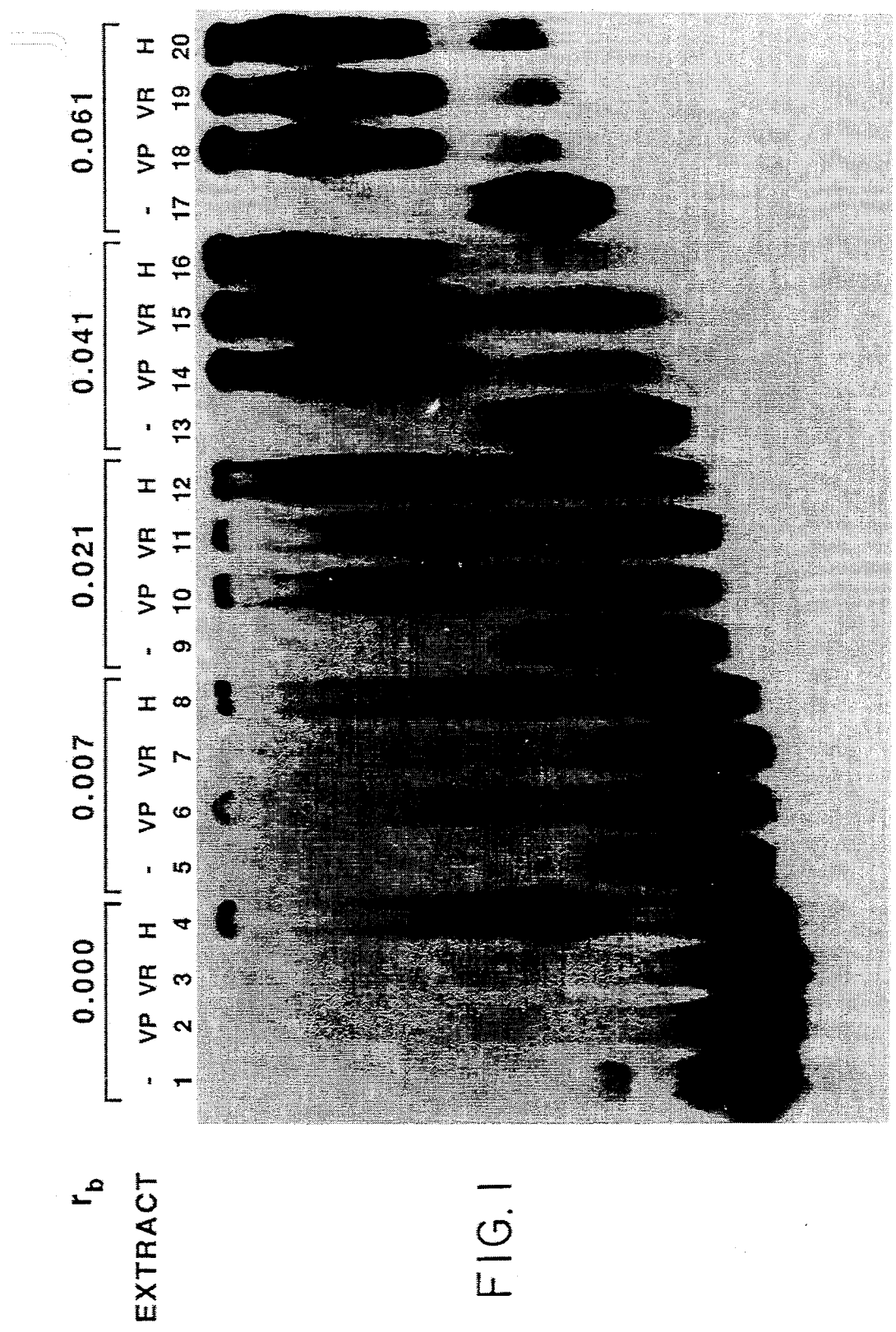
FIG. 1 is an autoradiograph of the results of an electrophoretic mobility shift assay (EMSA) showing the binding of cellular factors to platinated DNA (cis-DDP modified DNA) at different bound ratios of Pt/nucleotide ($r_b$) as indicated at the top of the autoradiograph. —, platinated DNA incubated in the absence of cellular extract; VP, platinated DNA incubated with V79 parental cell line extract; VR, platinated DNA incubated with V79 cis-DDP resistant cell line extract; H, platinated DNA incubated with HeLa cell line extract.

The present invention is based on the discovery in extracts of mammalian cells of a DNA structure-specific recognition protein (SSRP), which recognizes and selectively binds to a structural motif present in damaged DNA. SSRP was originally defined by its characteristic of selectively binding to DNA damaged by therapeutically active platinum compounds and thus it was previously referred to as a DNA damage-recognition protein (DRP), and specifically as a cis-DDP DRP. The protein disclosed and referred to as cis-DDP DRP in U.S. Ser. Nos. 07/539,906 now abandoned, and 07/410,981 now abandoned is the same as the protein described herein as SSRP.

The term "structural motif" is intended to encompass any type of nucleic acid secondary structure or tertiary structure which differs in a detectable manner from ordinary helical duplex DNA. Structural motifs can be sequence-dependent or sequence-independent. Thus, cruciform DNA, kinked DNA, overwound, partially unwound or underwound helical DNA, different helical forms of DNA (e.g., A or Z helices), junctions between different helical forms, modified bases (e.g., thymine dimers, methylated guanosine or cytosine residues), and combinations thereof, are all examples of DNA structural motifs. See generally, W. Saenger, Principles of Nucleic Acid Structure, *Springer Advanced Texts in Chemistry*, C. Cantor, series ed., Springer-Verlag New York, Inc., New York (1984).

Structural motifs can be generated during the course of normal or aberrant cellular activities in which DNA participates, such as DNA replication, recombination, or repair. Certain structural motifs comprise DNA damage or lesions; others are thought to be associated with the control of cellular processes. Structural motifs generally classified as DNA damage can be produced by drugs which interact with nucleic acids to form detectable lesions such as base- or sugar-drug adducts, or intercalations. DNA damage-associated structural motifs can also be produced spontaneously, e.g., by exposure to or contact with an environmental damage-causing agent. Such an agent can be a chemical compound or a physical agent (e.g., UV radiation). Friedberg, E. C., *DNA Repair*, Chapter 1, W. H. Freeman & Co., New York (1985).

A DNA structural motif of particular interest comprises a 1,2-intrastrand dinucleotide adduct. This type of structural motif or lesion is known to be formed as a result of the interaction of therapeutically effective platinum compounds which are used for the treatment of cancer (e.g., cis-DDP or cisplatin) with DNA. As described more fully below, it has been suggested that the structural motif or lesion produced by therapeutically active platinum drugs interacts with the cellular machinery for DNA repair. Therefore, a factor, such as a protein, which is capable of selectively recognizing this structural motif (i.e., a platinated DNA motif comprising a region of DNA damage or a lesion, specifically a 1,2-intrastrand dinucleotide adduct of cisplatin), is a valuable tool for developing an understanding of the mechanisms underlying susceptability and/or resistance to cancer and to particular cancer therapeutics. Accordingly, the platinated 1,2-intrastrand dinucleotide adduct DNA structural motif has been employed as a model system for the method of the invention described herein. It will be understood that the present method of identification and isolation of structure-specific recognition proteins (SSRPs) can also be used to identify and isolate SSRPs which recognize other DNA structural motifs; its utility is not confined to the 1,2-intrastrand dinucleotide adduct of a therapeutically effective platinum compound.

The present invention relates to a method of identifying and isolating DNA structure specific recognition proteins (SSRPs) which bind selectively to particular DNA structural motifs present in mamalian cells as a result of spontaneous damage or environmental damage. It relates to SSRPs identified according to this method, and to antibodies reactive with these SSRPs. It relates further to DNA and RNA and to nucleic acid probes encoding SSRPs identified according to the method described herein. The method of the present invention will now be described in the context of its use to identify and characterize a DNA structure-specific recognition protein which selectively binds cisplatin-modified DNA. cis-DDP SSRP was identified and characterized in mammalian and other eukaryotic cells, as described more fully in the Examples which follow. Isolation and cloning of a human cDNA encoding SSRP (Seq. ID No. 6) of the present invention is also described herein. Other aspects of the present invention comprising the use of SSRP as well as of nucleotide sequences encoding it and antibodies reactive with it, for therapeutic, diagnostic and prophylactic purposes are also discussed below.

Platinated DNA Structural Motifs cis-Diamminedichloroplatinum(II) (cis-DDP or cisplatin) is a clinically important antitumor drug used mainly to combat ovarian and testicular malignancies. Loehrer, P. J. and L. H. Einhorn, *Ann. Intern, Med.,* 100:704–713 (1984). The major cellular target for cis-DDP is generally accepted to be DNA, although it is not yet certain whether antitumor efficacy is a consequence of impaired replication or transcription. Sorenson, S. M. and A. Eastman, *Cancer Res.* 48:4484–4488 and 6703–6707 (1988). Covalent coordination of the hydrolysis products of cis-DDP to the bases in DNA can lead to inhibition of DNA synthesis in vitro and in vivo and cause mutagenesis. Lee, K. W. and D. S. Martin, Jr., *Inorg. Chim. Acta,* 17:105–110 (1976); Lim, M. C. and R. B. Martini, *J. Inorg. Nucl. Chem.* 38:119–1914 (1984); Pinto, A. L., and S. J. Lippard, *Proc. Natl. Acad. Sci., USA,* 82: 4616–4619 (1985); Harder, H. C., and B. Rosenberg, *Int. J. Cancer,* 6:207–216 (1970); Howle, J. A. and G. R. Gale, *Biochem. Pharmacol,* 19:2757–2762 (1970); Burnouf, D. et al., *Proc. Natl. Acad, Sci., USA,* 84:3758–3762 (1987).

trans-Diamminedichloroplatinum(II), the geometic isomer of cis-DDP in which the amine and chloride moieties are in mutually trans positions, is ineffective as a chemotherapeutic agent. Connors, T. A. et al., *Chem.- Biol. Interact.* 5:415–424 (1972). trans-DDP will block replication at doses equitoxic to those of cis-DDP. It has been postulated that differential repair may be responsible for the chemotherapeutic effectiveness of cis-DDP compared to trans-DDP. Ciccarelli, R. B. et al., *Biochemistry* 24:7533–7540 (1985). The trans-DDP reaction products with DNA include monofunctional adducts, intrastrand cross-links, interstrand cross-links, and protein-DNA cross-links. Pinto A. L. and S. J. Lippard, *Proc. Natl. Acad. Sci. USA* 82:4616–4619 (1985); Eastman, A. and M. A. Barry, *Biochemistry* 26:3303–3307 (1987). trans-DDP cannot form intrastrand cross-links between adjacent nucleotides, and this observation has led to the suggestion that the d(GpG) and d(ApG) adducts formed uniquely by cis-DDP are responsible for its antitumor activity. Cardonna, J. P. and S. J. Lippard, *Adv. Chem. Ser.* 209:14–16 (1983); and Pinto, A. L. and S. J. Lippard, *Biochem. Biophys. Acta* 780:167–180 (1985). This hypothesis is supported by the observation that most chemotherapeutically effective platinum compounds have chloride moieties in cis positions and are believed to form a spectrum of DNA adducts similar to those of cis-DDP, i.e., 1,2-intrastrand cross-links. Lippard, S. J. et al., *Biochemistry* 22:5165–5168 (1983).

The chemical formulae for cis- and trans-DDP, and for several clinically related platinum compounds are as follows:

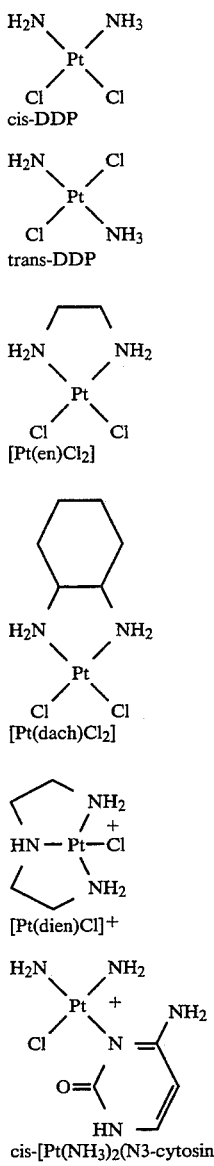

cis-DDP binds to DNA in a bidentate manner, forming mainly 1,2-intrastrand d(GpG) and d(ApG) cross-links that kink the strand of the helix bearing the platinated adduct, and possibly concurrently form a localized single stranded region of the opposite strand which would be detectable by antinucleoside antibodies. Sherman, S. E., and S. J. Lippard, *Chem. Rev.,* 87:1153–1181 (1987); Rice, J. A. et at., *Proc. Natl. Acad. Sci., USA.* 85:4158–4161 (1988); Sundquist, W. I. et al., *Biochemistry,* 25:1520–1524 (1986). The 1,2-intrastrand d(GpG) adduct of cis-DDP produces a bend in the helix of DNA by 32°–34° directed toward the major groove (Rice, J. A., Crothers, D. M., Pinto, A. L. & Lippard, S. J. (1988) *Proc. Natl, Acad, Sci. U.S.A.* 85:4158–4161; Bellon, D. F. & Lippard, S. J. (1990) *Biophys. Chem.* 35: 179–188). Initially, it was thought that either this kink or the postulated local region of ss DNA opposite to the platinum adduct could comprise a recognizable structural motif.

The 1,3-intrastrand d(GpTpG) adduct of cis-DDP also bends the helix by 34°, concurrently unwinding the DNA strand opposite to the adduct to a much greater degree than in the 1,2-intrastrand adducts produced by this compound. Moreover, it is not known if this bend is directed toward the major groove of the DNA helix. It is possible that the helix bend produced by this platinum adduct is more flexible than the helix kink produced by the 1,2-intrastrand adducts of cis-DDP. Bellon, S. F. & Lippard, S. J. (1990) *Biophys. Chem.* 35:179–188. It should be noted that cyclobutane-type pyrimidine dimers formed by UV irradiation also have been suggested to bend the DNA helix by 30°. Husain, I., Griffith, J., & Sancar, A. (1988) *Proc. Natl. Acad. Sci. U.S.A.* 85:2558–2562. This bend is probably in the direction of the major groove. Pearlman, D. A., Holbrook, S. R., Pirkle, D. H. & Kim, S. (1985) *Science* 27:1304–1308.

The other platinum compounds illustrated above form interstrand platinated DNA adducts (e.g., trans-DDP) or monofunctional adducts (e.g., {Pt(dien)Cl}Cl or {Pt(NH3)2(N3-cytosine)}).

The above-illustrated platinum compounds were employed to investigate the nature of the structural motif produced by therapeutically active platinum compounds and selectively recognized by SSRP. It was possible to determine whether the motif recognized by the cis-DDP SSRP described below comprised a particular helix kink or bend, a local region of DNA unwinding, the platinum atom itself, or a combination of these elements.

Method of Identifying SSRP in Cell Extracts

DNA modified by the antitumor drug cis-diamminedichloroplatinum(II) (cis-DDP or cisplatin) was used to identify a factor present in crude extracts of mammalian cells which binds to cisplatin-damaged DNA. This factor, referred to as cis-DDP DNA structure-specific recognition protein (cis-DDP SSRP) binds selectively to double stranded DNA fragments modified by cis-DDP, {Pt(en)Cl2} ("en" refers to ethylenediamine) or {Pt(dach)Cl2} ("dach" refers to 1,2-diaminocyclohexane), but not to DNA modified with either trans-DDP or {Pt(dien)Cl}Cl ("dien" refers to diethylenetriamine). It is important to note that the latter two platinum compounds are clinically ineffective and are unable to form 1,2-intrastrand dinucleotide adducts, whereas the first three compounds are capable of forming this type of DNA structural motif. The major DNA adducts of cis-DDP or cisplatin are d(GpG) and d(ApG) 1,2-intrastrand cross-links, which represent 65% and 25% of all such adducts, respectively. Thus, SSRP described herein binds specifically to these -intrastrand d(GpG) and d(ApG) adducts.

It is likely that SSRP (or a similar factor) also binds to DNA which has been damaged by other means, such as other genotoxic agents, which result in the formation of motifs comprising intrastrand cross-links and/or the introduction of platinum into the DNA. SSRP may recognize a structural motif common to certain platinum-DNA adducts and to other types of DNA damage. It is also possible that it recognizes sequences which form tertiary DNA structural domains or motifs comprising sites of specific protein-DNA interactions.

It is of interest to note that although prokaryotic DNA repair systems have been identified, comparatively little is known about corresponding factors that process damaged DNA in eukaryotic cells. Friedberg, E. C., *DNA Repair,* (W. H. Freeman and Co., New York (1985). From the information available, however, it appears that mammalian DNA repair enzymes possess damage-specific DNA binding properties, ibid., pp.

150-152. In other words, repair enzymes and possibly other components of the cellular DNA repair machinery bind selectively to DNA structural motifs associated with DNA damage or lesions. The studies described herein were initially designed to investigate the hypothesis that in eukaryotic cells there is a structure-specific DNA binding factor or recognition protein with sufficient generality to recognize cisplatin-modified DNA as an initial step in the DNA-lesion repair process.

These studies culminated in the discovery of a eukaryotic cellular factor (SSRP) in mammalian cells, both human and non-human, which selectively recognizes and binds a DNA structural motif associated with DNA damage. It follows that the factor described herein, alone or in conjunction with other cellular constituents, could be of general importance in the initial stages of processing of eukaryotic DNA which has been damaged by a genotoxic agent, such as cisplatin, and may belong to a wider class of cellular damage- or structure-specific recognition proteins. The cis-DDP SSRP has been shown to be present at least in human (i.e., HeLa) and non-human (i.e., hamster V79) mammalian cells and it should be emphasized that the cis-DDP binding factor occurs and produces approximately the same electrophoretic band shift in all cell lines tested. cis-DDP SSRP may be ubiquitous to all eukaryotic cells.

Thus, the existence of at least one factor which specifically recognizes and binds to a damaged DNA structural motif has been demonstrated. It is important to note that the factor selectively recognizes a DNA structural motif produced by the interaction of an antitumor drug with DNA. Little or no binding of the cellular cis-DDP SSRP to unmodified (unplatinated) DNA occurs. Cellular cis-DDP SSRP binding to DNA fragments containing the above platinum adducts could be observed using damaged DNA fragments having as few as two platinated DNA lesions per 1,000 nucleotides. Low levels of binding to singled stranded DNA modified by cis-DDP were also observed.

Although SSRP is described herein in the context of its ability to bind DNA damaged by an exogenous agent (a specific anticancer drug, cisplatin) it is likely that it, or a functional equivalent thereof, has a wider, more generalized role in DNA recognition and processing. This conclusion is based upon the fact that nature could not have evolved a system specific only for a particular drug or its adducts. That is, it is likely that the SSRP identified and described herein or a similar factor (i.e., one which has a similar specificity for and ability to bind to damaged DNA) interacts with DNA damaged by other means (e.g., spontaneous damage, environmental damage).

Turning now to the method by which SSRP was identified, cellular extracts were assessed for the presence of the cis-DDP SSRP by a method comprising two independent, mutually corroborative techniques. One of these was a modified Western blot analysis (also known as Southwestern blotting) wherein electrophoretically resolved, blotted cellular proteins were renatured in situ (i.e., on the blot surface) and assessed for the ability to bind to a $^{32}$P-labelled, damaged DNA fragment (e.g., comprising at least one cisplatin-DNA adduct). A protein identified as cellular cis-DDP SSRP by its ability to form a (damaged DNA fragment):(protein) complex on the blot surface was observed to have an apparent molecular weight of approximately 100 000 daltons; these results are described more fully in the Examples which follow.

The other technique relied upon in the present method of identifying SSRPs was electrophoretic gel mobility shift assay (EMSA, also known as bandshift analysis). Initially, cell extracts were incubated in the presence of a $^{32}$P-labelled, damaged DNA fragment (e.g., comprising at least one cisplatin-DNA adduct) and subjected to electrophoretic resolution, whereupon a (damaged DNA fragment):(protein) complex formed in solution was detectably resolved from the soluble, damaged DNA fragment alone (e.g., see FIG. 1). This analysis for the presence of SSRP was further refined by EMSA studies wherein chemically synthesized oligonucleotide probes containing predefined chemical DNA adducts were used to characterize the structural features of platinated DNA which comprise the motif recognized by the cellular SSRP (see FIG. 9). These studies demonstrated that the 1,2-intrastrand d(GpG) and d(ApG) aducts formed by cis-DDP were specifically recognized by the cis-DDP SSRP.

A competitive EMSA technique also allowed the determination of the dissociation constant (which is the reciprocal of the binding constant to platinum-damaged DNA) and other properties of the cisplatin SSRP. With this technique, it was demonstrated that the dissociation constant for in-solution formation of a (damaged DNA fragment):(protein) complex is in the range of $(1-20) \times 10^{-10}$M, and that the protein described herein as cellular cis-DDP SSRP has an apparent molecular weight of about 91 000 daltons.

It should be emphasized that the method of identifying SSRPs, while described herein with specific reference to the identification of at least one factor which selectively binds cisplatin-damaged DNA, can be used to identify and characterize other DNA structure-specific recognition proteins. For example, the present method can be used to identify other DNA SSRPs which hybridize to a particular probe, such as a cis-DDP-modified DNA restriction fragment, which has been previously shown to identify a factor which binds a particular type of damaged DNA (e.g., cisplatin-damaged DNA). If lower stringency conditions are used, for example, the probes described herein can be used to identify other DNA SSRPs (possibly also including factors which bind DNA damaged through the action of another chemical agent or radiation).

Both of the above techniques are described more fully below, particularly in the Examples. The similarity of the molecular weights of the cellular proteins identified by these two independent techniques supports the conclusion that, in each case, the same SSRP is observed. Further support is derived from the fact that the two have the same binding specificities for DNA modified with different platinum compounds. The cloning and characterization of human, *Drosophila melanogaster* and *Saccharomyces cerevisiae* cDNAs (Seq. ID Nos. 6 and 10, respectively) encoding a protein having the characteristics of the cellular SSRP is also described below.

I. Electrophoretic Mobility Shift Analysis

A gel electrophoretic mobility shift assay (EMSA) was used in conjunction with radiolabelled DNA restriction fragments or chemically synthesized oligonucleotide probes containing specific, predefined platinum-DNA adducts, to characterize the structural features of platinated DNA which are specifically recognized by the structure specific DNA recognition protein (SSRP) described herein. EMSA, also known as bandshift analysis, was originally described as useful for characterizing mammalian transcriptional control factors. Fried, M. and D. M. Crothers, *Nucleic Acids Res.* 9:6505–6525 (1981); Singh, H. et al., *Nature*, 319:154–158 (1986). Specific DNA-binding factors in a complex mixture of proteins have been identified by this technique through the use of recognition sites containing $^{32}$P-labeled DNA fragments in the presence of a large molar excess (e.g. $10^4$-fold) of competitor DNA, such as poly(dI-dC)•poly(dI-dC).

Briefly, the studies described in Examples A–K resulted in identification and characterization of a cellular protein that selectively recognizes a DNA structural motif produced by the interaction of particular platinum compounds with DNA. In particular, this work has elucidated several key properties of a cellular protein that binds selectively to DNA modified with the antitumor drug cis-DDP. The platinum damage or structure-specific recognition protein may be part of a DNA repair complex or it may be a cellular constituent that responds to structural elements that occur or arise naturally in the genome. For present purposes, it is not important to distinguish between these two possibilities. However, it should be emphasized that since it is unlikely that biological systems would evolve a protein to complex with cisplatin adducts specifically, cis-DDP SSRP probably recognizes a naturally-occurring structural motif common both to certain platinum-DNA adducts and to other types of DNA damage, or possibly to sequences which form tertiary DNA structural domains that are the sites of specific protein-DNA interactions.

The results of EMSA studies described in Example A and presented in FIG. 1 demonstrate the existence of a cellular factor that binds with selectivity to cisplatin-DNA adducts. The slower migration through the gel of platinated DNA associated with (i.e., complexed with) the DNA-binding factor allowed it to be readily visualized. The factor was identified in nuclear extracts from human HeLa and Chinese hamster V79 parental and cis-DDP-resistant (adapted to 15 μg/mL cis-DDP) cell lines. Selectivity of binding was demonstrated by the positive correlation between the extent of binding and the extent of DNA modification. A minimum modification level of 0.007 Pt/nucleotide was required to observe binding of the factor to labeled platinated DNA, whereas at a modification level of 0.06 Pt/nucleotide, nearly all labeled DNA was complexed. For probes of higher $r_b$ (ratio of bound Pt per nucleotide) values, two bands are observed in the gel. This result may indicate the binding of two equivalent cellular factors to those DNA molecules having higher numbers of damaged sites.

Cisplatin-damaged DNA fragments incubated with nuclear extracts from either V79 parental or resistant cell lines were bound to a similar extent, suggesting that its expression is not associated with an acquired resistance to cis-DDP. It will also be apparent that the results reveal the presence of a factor causing approximately the same magnitude of band shift in cell extracts obtained from two dissimilar species, supporting the postulate that a similar (e.g., highly conserved) factor was being observed in both species. The cis-DDP specific DNA-binding factor has also been found in nuclear extracts from human B cells and from cytosolic extracts prepared from HeLa cells.

Figure 2:
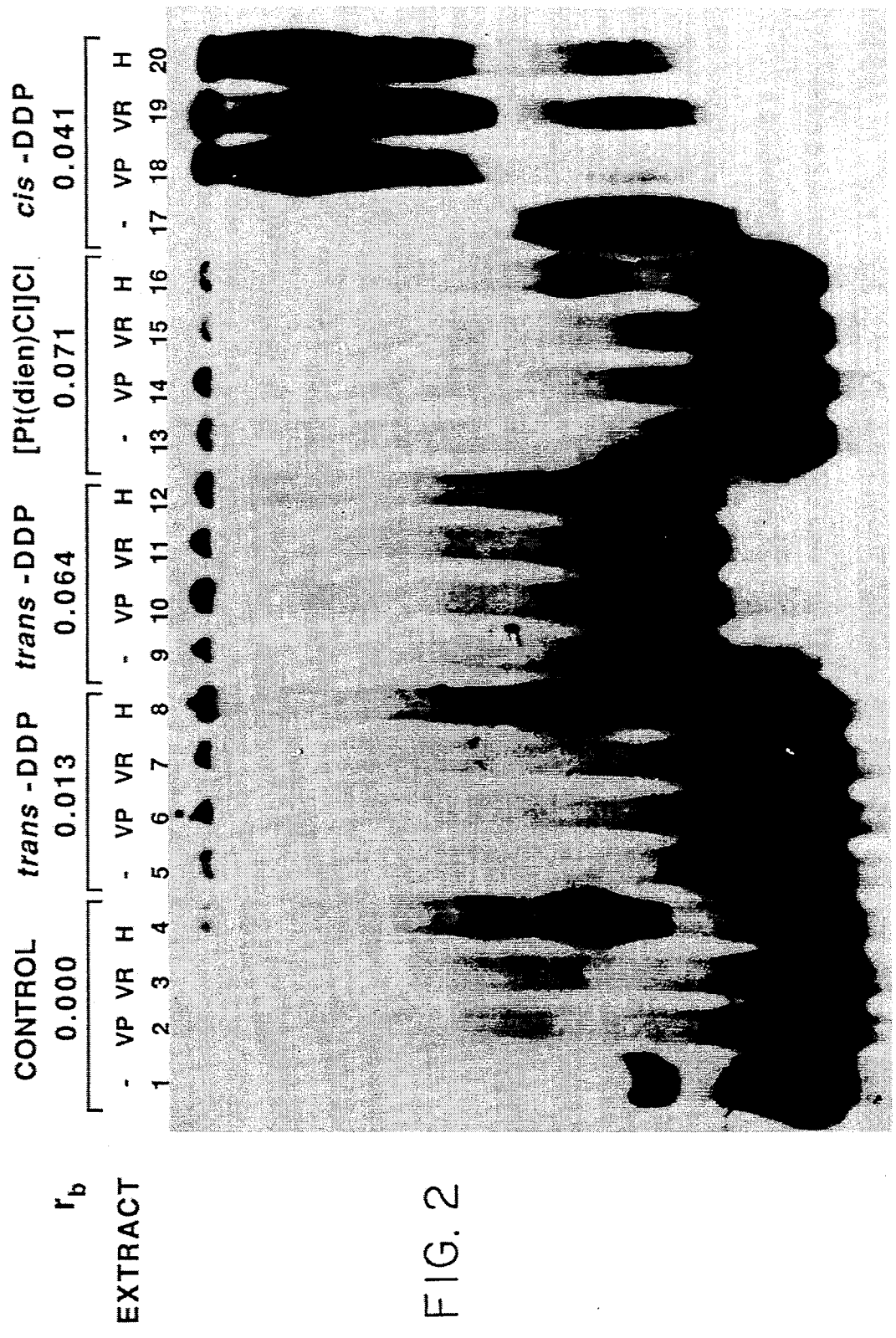
FIG. 2 is an autoradiograph of the results of an EMSA study showing the structural selectivity of the cellular factor for cisplatin modified DNA. $r_b$, —, VP, VR and H are as identified in FIG. 1.

A preliminary study of the selectivity of the cellular DNA binding factor for cis-DDP DNA adducts is described in Example B. As shown in FIG. 2, the cellular factor bound selectively to DNA modified with cis-DDP, but not to DNA modified with either trans-DDP or {Pt(dien)Cl}Cl.

The nature of the structural motif selectively recognized by SSRP was further elucidated in a more refined EMSA selectivity study, discussed in Example G. These results are presented in FIG. 6, which demonstrates that the cellular SSRP binds selectively to DNA modified with cis-DDP, {Pt(en)Cl$_2$}, and {Pt(dach)Cl$_2$}, but not to DNA modified with either trans-DDP or {Pt(dien(Cl)}Cl. It is important to note that the latter two platinum compounds are unable to link adjacent nucleotides in DNA, whereas the former three are known to form 1,2-intrastrand d(ApG) and d(GpG) adducts. These results directly support the conclusion that SSRP selectively recognizes a DNA structural motif comprising a 1,2-intrastrand dinucleotide adduct.

Figure 3:
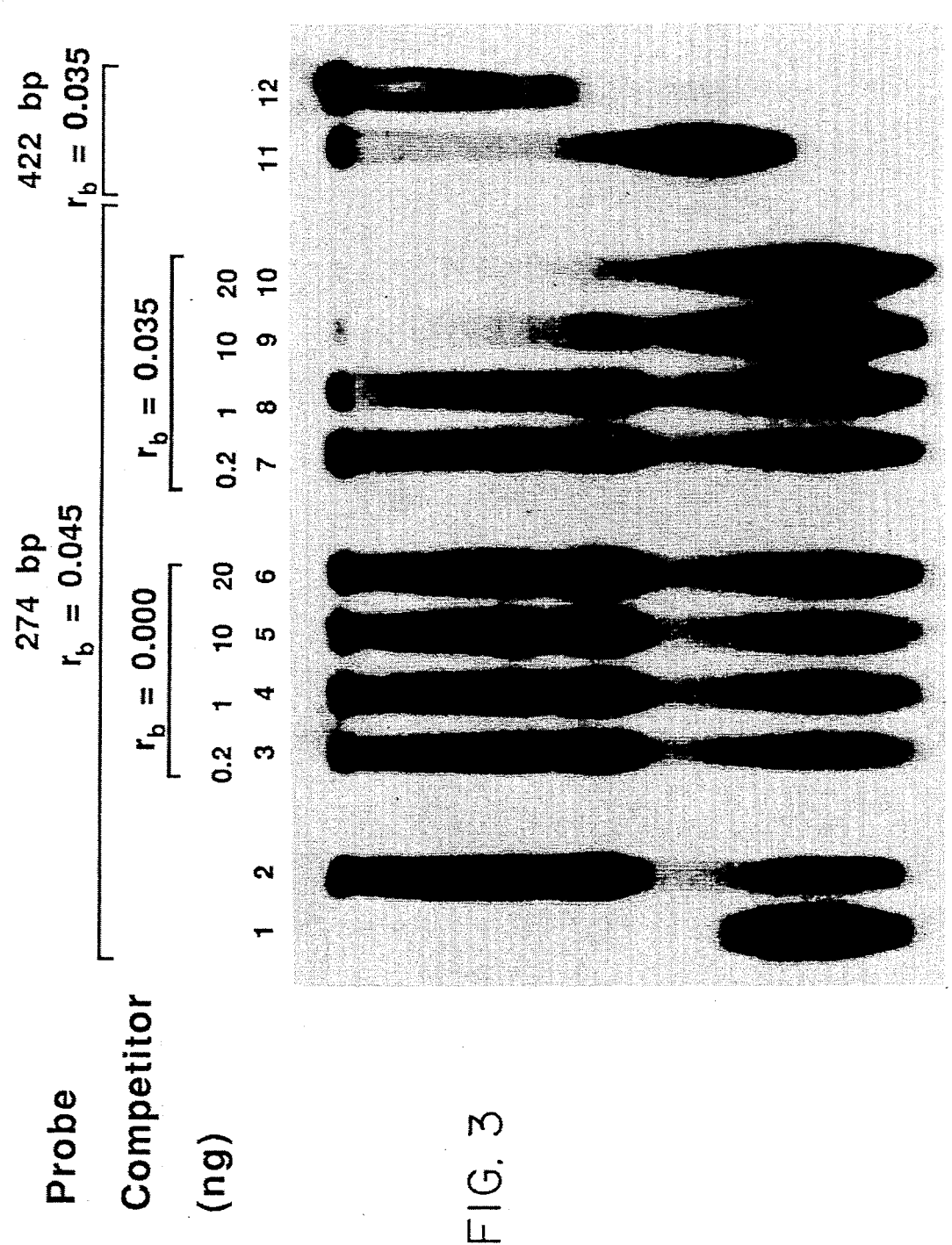
FIG. 3 is an autoradiograph of the results of an EMSA study showing that binding to labelled platinated DNA can be competed with unlabelled platinated DNA but not with unlabelled, unplatinated DNA. $r_b$ is as identified in FIG. 1.

A preliminary competitive binding experiment, described in Example C, was performed to assess the specificity and affinity of the cellular factor for cis-DDP-treated DNA. As shown in FIG. 3, binding of the cellular factor to a radiolabelled, cis-DDP-modified 274 bp restriction fragment of DNA prepared from the plasmid pSTR3 was effectively competed by increasing quantities of an unlabelled, cis-DDP-modified 422 bp restriction fragment derived from M13mp18 DNA. Binding could be completely competed with a 100-fold excess of unlabeled modified DNA; however, unmodified 274 bp fragment did not compete for binding of the cellular factor (see lane 10 of FIG. 3).

From the data in lane 8 of FIG. 3, the equilibrium constant for binding of the platinated DNA to the cellular factor was initially estimated to be $3 \times 10^8 M^{-1}$. Müller, R., *Methods in Enzymology*, 92:589–601 (1983). The same analysis provided an estimate of the concentration of the factor in crude extracts of approximately $4 \times 10^{-9}M$. Ibid. Similar results were obtained when the labeled 274 bp fragment was competed with unlabeled 274 bp fragment modified to the same extent.

Figure 5:
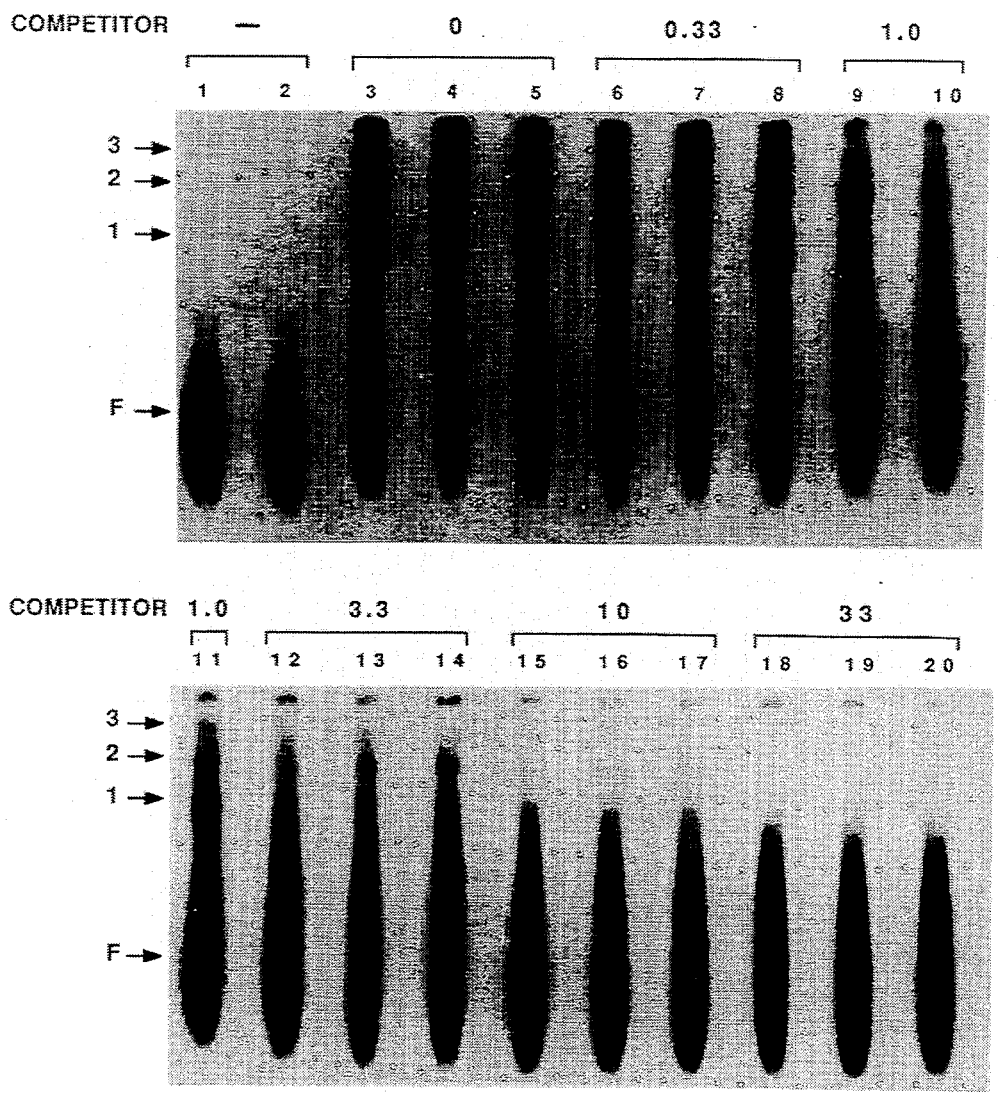
FIG. 5 is an autoradiograph of the results of an EMSA study showing that binding to labelled platinated DNA can be competed with unlabelled platinated DNA but not with unlabelled, unplatinated DNA. $r_b$ is as identified in FIG. 1.

The results of a subsequent competition study, discussed in Example F and presented in FIG. 5, demonstrated that the true value of the dissociation constant of the cellular factor identified as SSRP for its ligand, a particular DNA structural motif produced as a result of cis-DDP DNA adduct formation, lies in the range $(1-20) \times 10^{-10}M$.

A displacement assay was also performed in which 0.1 ng of radiolabelled, cis-DDP-modified DNA (0.035 Pt/nucleotide) was incubated with 7.3 μg of nuclear extract from cis-DDP-resistant cell lines at 37° C. for 15 minutes. Subsequently, varying concentrations of unlabelled, modified DNA were added to the mixtures and incubation was continued for an additional 15 minutes. In contrast to the results from the above competition assays, results of the displacement assay showed that the cellular factor remained bound to the labelled, platinated DNA even in the presence of a 1000-fold excess of unlabelled, platinated DNA.

The competitive EMSA approach was also successfully employed for a concurrent analysis of the specificity and affinity of the cellular structure-specific recognition protein for cis-DDP-treated DNA. In this study, discussed in detail in Example H, synthetic DNA fragments containing predetermined types of platinum- DNA adducts were prepared from the oligonucleotides depicted in FIG. 7 (Seq. ID Nos. 1–5). These fragments were radiolabelled and used in EMSA binding reactions in conjunction with an unlabelled competitor DNA fragment, comprising the 422 bp restriction fragment described in Example A, either untreated or treated with cis-DDP. The results of this competitive analysis, shown in FIG. 8, revealed that SSRP binds selectively to DNA modified with the antitumor drug cis-DDP and that it is specific for the 1,2-intrastrand d(GpG) and d(ApG) adducts formed by cis-DDP. In contrast, SSRP does not recognize the 1,3-intrastrand d(GpTpG) adducts formed by cis- and trans-DDP, nor does it recognize a monofunctional adduct formed by $\{Pt(NH_3)_2(N3\text{-cytosine}\}^{2+}$ at the N7 position of deoxyguanosine. As noted previously, The cis 1,3-intrastrand cis-d(GpTpG) adduct unwinds the DNA helix to a much greater extent than the 1,2-intrastrand d(GpG) and d(ApG) adducts of this drug. This 1,3-intrastrand cross-linked adduct may therefore unwind the helix too much for SSRP recognition. Furthermore, the possibility that an amino acid residue of SSRP interacts directly with the platinum atom is unlikely since the protein does not bind to DNA modified with structurally distinct (e.g., interstrand or monofunctional) DNA adducts having a platinum atom as a common element.

The above-described studies did not conclusively exclude the possibility that the cellular factor observed to bind selectively to platinated DNA might actually recognize a single-stranded domain adjacent the platinum-DNA adducts. Recognition of ss DNA was affirmatively excluded by a competitive EMSA study (Example I) in which nuclear extracts from HeLa cells were presented with unlabelled, ss M13mp18 DNA in addition to the putative platinated DNA ligand, represented by the above radiolabelled, platinated 274 bp double-stranded restriction fragment. The ss M13mp18 DNA did not compete for binding of the cellular factor, indicating the absence of ass DNA binding factor.

As noted previously, cyclobutane-type pyrimidine dimers formed by UV irradiation also have been suggested to bend the DNA helix by 30°, probably in the direction of the major groove. Recently, Chu and Chang reported the presence of a factor in nuclear extracts prepared from HeLa cells that binds specifically to DNA damage induced by UV irradiation. Chu, G. and E. Chang, Science 242:564–567 (1988). A study was initiated to test the logical hypothesis that SSRP and the factor described by Chu and Chang recognizes a common structural motif: a helical bend or kink of about 30° in the direction of the major groove.

The results of this EMSA study, which relied upon differential competition between cis-DDP modified and UV-damaged DNA fragments, are set forth in Example J. The results of this comparison, reported in Donahue, B. A. et al. (1990), Biochemistry 29:5872–5880, demonstrate that the DNA binding factor described herein as cis-DDP SSRP does not recognize DNA lesions induced by UV light. Therefore, the structural motif recognized by cis-DDP SSRP does not correspond to the type of lesion produced by the irradiation of DNA with UV light.

The conclusion can be drawn from the above EMSA studies that the cellular cis-DDP SSRP does not specifically recognize 30°–34° kinks in the helix, nor does it simply respond to the presence of ss DNA formed opposite the cisplatin lesion, as evidenced by the failure of ss DNA to compete with platinum-modified DNA for binding. The protein may, however, recognize a particular combination of directed helix axis bending and local unwinding at the site of platination in 1,2-intrastrand cis-DDP-DNA cross-links.

II. Modified Western Blotting Analysis

In an alternative approach to the EMSA technique described above, modified Western (i.e., Southwestern) blotting was used to identify a factor, present in HeLa cells, which selectively binds to DNA modified by cis-DDP or $\{Pt(en)Cl_2\}$. This technique is described more fully in Example L. Southwestern blotting analysis allowed a determination of the apparent size of the cellular protein having the ability to form (damaged DNA fragment):(protein) complexes with platinum-modified DNA fragments. SSRP was observed to have an electrophoretic mobility corresponding to a molecular mass of approximately 100 000 daltons for a globular protein (see lane 1 of FIG. 11). Only double-stranded DNA restriction fragments modified by cis-DDP or $\{Pt(en)Cl_2\}$ bound selectively to the human cellular SSRP. A low level of SSRP binding to single stranded (ss) DNA modified by cis-DDP was observed, and little or no detectable binding was seen when unmodified single or double stranded DNA restriction fragments were used as probes for the blotted proteins. No appreciable binding to the factor, using DNA modified with the clinically ineffective trans-DDP or $\{Pt(dien)Cl\}Cl$ compounds, was observed, compared with results for unplatinated control DNA.

It should also be noted that, in lane 1 of FIG. 11, a molecular species of about $M_r = 28\ 000$ daltons also bound a significant amount of the cis-DDP and $\{Pt(en)Cl_2\}$ modified DNA fragments with which the Southwestern blots were probed. Initially, it was thought that this factor arose through proteolytic degradation of the cellular SSRP. Results of subsequent investigations suggest that this factor is, or is related to, the known protein HMG-1. Southwestern blotting studies also demonstrated that extent of (damaged DNA fragment):(protein) complex formation depended upon the level of DNA modification by cis-DDP. In addition, the Southwestern blotting system described herein was found to have a detection limit for SSRP of approximately 2 platinum adducts per 1000 nucleotides, also expressed as an $r_b$ level of 0.002. This technique was also used, as described below, for screening a human cDNA expression library for the presence of transcripts corresponding to polypeptides having SSRP activity.

Further Characterization of the Cellular SSRP

Figure 4:
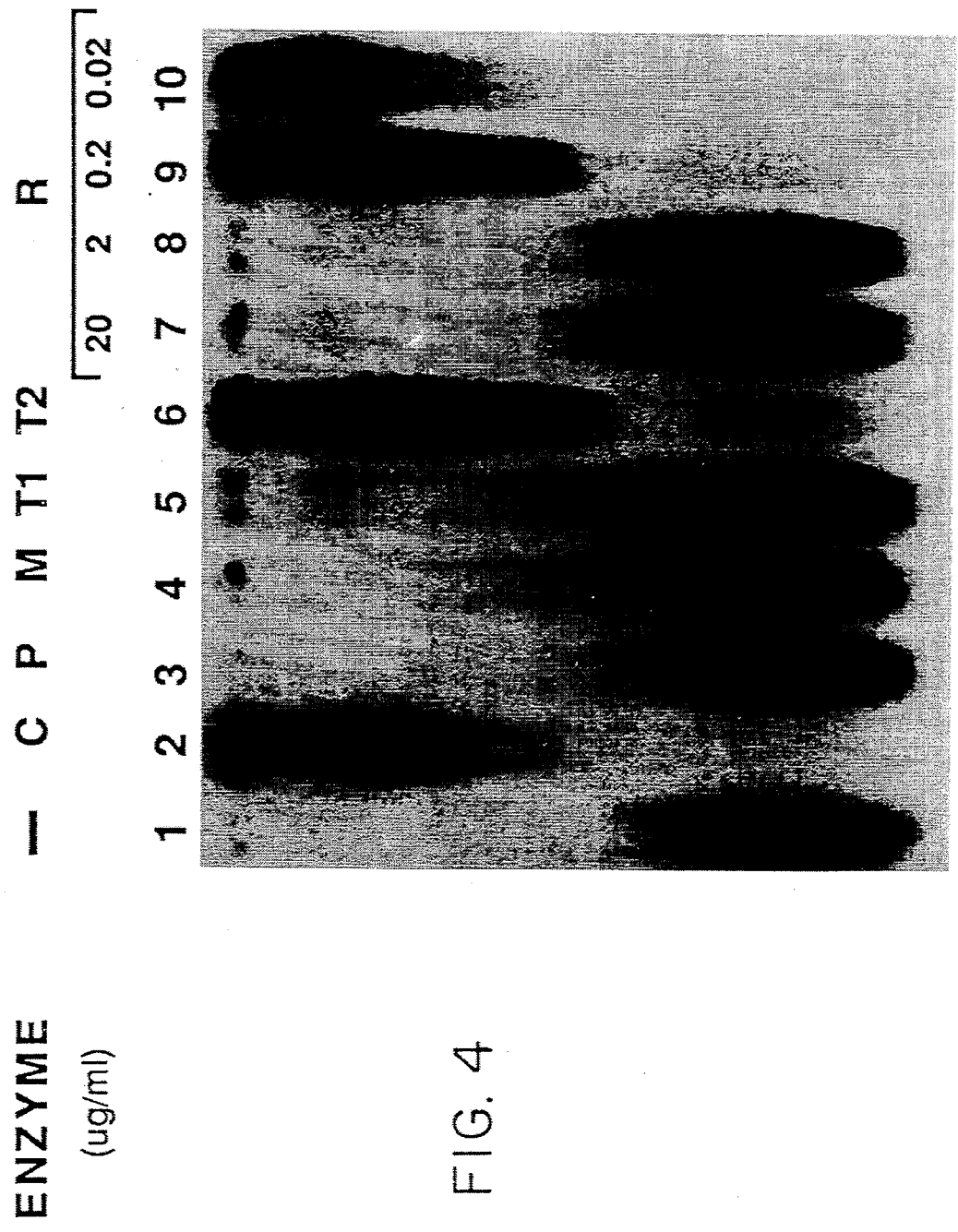
FIG. 4 is an autoradiograph of the results of an EMSA study assessing the sensitivity of the cellular factor in crude extracts to protease and ribonucleases.

The chemical nature of the cellular factor observed in HeLa cells was also assessed, by treating cytosolic extracts with either proteinase K or RNases, as described in Example D. Pretreatment of crude extracts with proteinase K resulted in loss of binding activity, confirming that the factor is a protein (this result is shown in FIG. 4). Pretreatment of crude extracts with RNase A also resulted in a loss of activity, however, this sensitivity disappeared after partial purification of the cis-DDP-DNA binding factor by ammonium sulfate fractionation and ion exchange chromatography as described below.

A study was carried out, as described in Example E, with the object of assessing the possible requirements of (damaged DNA fragment):(protein) complex formation as observed in EMSA studies with the cellular SSRP for certain metal ions or cofactors. No specific cofactor dependencies were revealed, however SSRP binding was observed to be inhibited by the presence, during the EMSA incubation step, of metal ions that have an affinity for sulfur donor ligands. This suggests that thiol moieties present in the protein may be involved at or near the site(s) of SSRP-DNA structural motif interaction.

The cellular protein identified as SSRP based upon its ability, observed in EMSA studies, to form (damaged DNA fragment):(protein) complexes with a soluble DNA fragment containing at least one 1,2-intrastrand dinucleotide adduct, was partially purified and subjected to preliminary characterization by sucrose gradient sedimentation as discussed in Example K. Fractions obtained from the sucrose gradient were assessed in parallel by SDS-PAGE and EMSA. These results, summarized in FIG. 9, indicated that the protein having SSRP activity has a sedimentation coefficient of 5.6 S, corresponding to an apparent molecular weight of 91 000 daltons for a globular protein.

Thus, as described herein, DNA structure specific recognition factor, which has been shown to be a protein, has been identified in mammalian cells, using two independent, corroborative approaches. The DNA structure specific recognition protein has been shown to bind selectively to DNA modified with cisplatin and to bind specifically to intrastrand d(GpG) and d(ApG) DNA adducts formed by cis-DDP. The protein may be involved in initial recognition of damaged DNA as part of a repair event. Alternatively, it may be part of the cellular response to stress, may be involved in maintaining the tertiary structure of DNA, or may initiate or suppress a DNA-directed function at a specific structural motif. It should be emphasized that cis-DDP SSRP occurs and produces approximately the same band shift in all cell lines tested; hence, it may be ubiquitous to all eukaryotic cells. The apparent molecular mass of SSRP as observed in the two techniques employed for identification of the factor are 91 000 daltons and 100 000 daltons (by EMSA and Southwestern blotting analysis, respectively). Further analysis, using known techniques, is expected to demonstrate conclusively whether the 100 000 dalton and the 91 000 dalton proteins identified by the two methods are, in fact, the same protein or are two members of a family of functionally related SSRPs. In either case, SSRP can be used to produce substances, as described herein, useful in the treatment (prevention, reduction) of DNA damage by genotoxic agents, such as anticancer drugs.

Figure 10A:
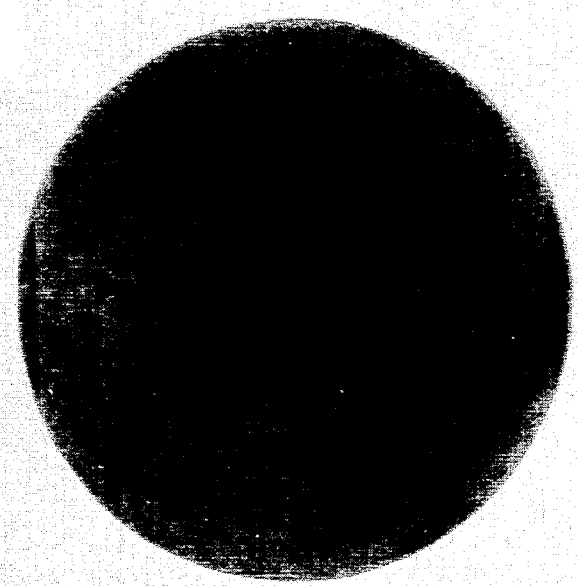
FIGS. 10A–B are an autoradiograph of protein replica filters prepared from a human B cell cDNA library constructed in the expression vector λgt11. Expression products were screened by a modified Western (or Southwestern) blotting technique for binding to a radiolabelled DNA restriction fragment. Both filters were prepared from the same tertiary screen for clone λPt 1 (Seq. ID No. 8) add: the top filter was probed with an unplatinated DNA restriction fragment, and the bottom filter was probed with the same DNA fragment, modified by cis-DDP. The filters show that clone λPt1 (Seq. ID No. 8) add has been purified to homogeneity.
Figure 10B:
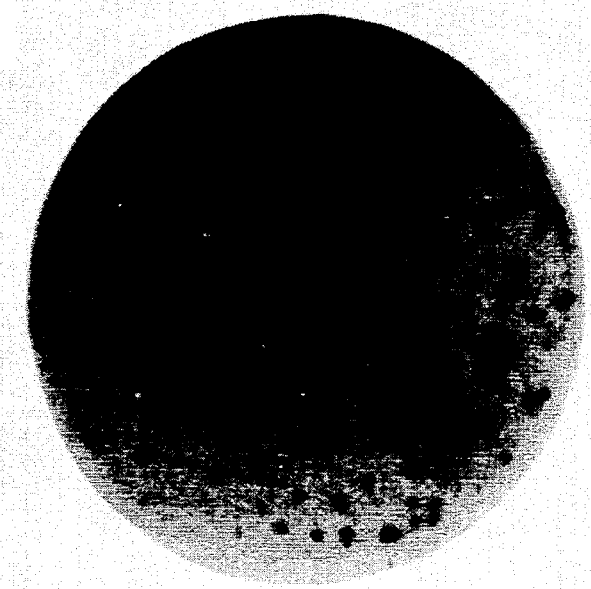

Cloning of SSRP from a cDNA Expression Library by a Modified Western Blot Screening Procedure The above-described selective binding of the HeLa cellular factor to DNA modified by cis-DDP suggested that it might be possible to isolate cDNA clones encoding the factor using cis-DDP-modified DNA as a probe. This approach proved fruitful: from a primary screen of 360,000 phage plaques, two recombinant phage, λPt1 (Seq. ID No. 8) and λPt2 (Seq. ID No. 9), were isolated from a human B cell expression library based upon the results of a Southwestern blot screening assay. FIG. 10 presents representative results from a tertiary screen which culminated in the purification of clone λPt1 (Seq. ID No. 8) to homogeneity. This Southwestern blot screening assay is described below in Example H; it was based upon the use of a radiolabelled 422 bp DNA restriction fragment modified by cis-DDP to an $r_b$ level of 0.040 (discussed in Example A).

E. coli lysogens (Y1089) containing the recombinant λPt1 gene (Seq. ID No. 8) were deposited on Sep. 22, 1988 at the American Type Tissue Culture Collection, 12301 Parklawn Drive, Rockville, Md. 20852, USA, under the terms of the Budapest Treaty and assigned accession number 40498; upon granting of a U.S. Patent all restrictions upon access to this deposit will be removed. Restriction maps of the λPt1 and λPt2 inserts (Seq. ID Nos. 8 and 9) are presented in FIG. 12. The two clones have insert sizes of 1.44 and 1.88 kb (for λPt2 and λPt1, respectively) and are aligned at their 5' ends (see also Example O). A consequence of the method by which these clones were isolated (i.e., a functional assay which depended upon the presence of polypeptides capable of binding the selected ligand, a cisplatin-damaged DNA fragment), the shorter clone, λPt2 (Seq. ID No. 9), serves to more precisely delimit the polypeptide sequence responsible for cis-DDP SSRP binding activity.

The polypeptides encoded by the recombinant phage have been assessed by Southwestern blotting analysis, described in Example N. FIG. 11 presents the results of a comparative study which demonstrated that the recombinant polypeptides exhibit DNA binding properties similar to those of the cellular factor identified by Southwestern blotting studies of crude extracts prepared from mammalian cells.

Expression of the Cellular Gene Encoding λPt2

Northern blot analysis of cytoplasmic RNA was carried out using clone λPt2 (Seq. ID No. 9) as a hybridization probe (Example P) for the presence of RNAs encoding cellular SSRP. An initial study revealed the presence of a 2.8 kb mRNA which is conserved at least between humans and rodents. The predicted molecular mass of the protein encoded by this mRNA transcript is 100 000 daltons, a size which correlates well with the results, discussed above, of modified Western blot analysis. See also, Toney, J. H., et al. (1989), *Proc. Nat. Acad. Sci, USA* 86:8328–8332.

Further studies revealed an expression pattern for the SSRP gene which is consistent with a function that is critical to a variety of tissues. Its presence does not correlate with the tissue-specific antitumor activity of cisplatin, however, nor with drug sensitivity in a series of resistant cell lines. Moreover, expression of the encoded message was not inducible in HeLa cells treated with a range of drug concentrations.

The Full-Length cDNA Sequence of Human SSRP was obtained by Screening cDNA Libraries with Clone λPt2

As noted previously, λPt2 (Seq. ID No. 9), the shorter of the two clones obtained initially by using a functional screen (based upon protein binding to cisplatin-modified DNA), served to define the region of SSRP responsible for DNA structural motif binding activity. As discussed below in Examples Q, R and S, the two clones obtained from Southwestern blot screening of a human cDNA expression library were in turn successfully employed as hybridization probes for the presence of additional SSRP sequences in several human cDNA libraries. The results of Southern blotting studies of the additional clones isolated in this manner are summarized in FIG. 13. Sequencing studies, described in Example S, allowed the construction of a predicted amino acid sequence of the human DNA structure specific recognition protein (Seq. ID No. 7), and revealed the presence of several distinct regions (shown in Seq. ID No. 7). These are shown in FIG. 14. The polypeptide encoded by λPt2 (Seq. ID No. 9) extends from residues 149-627 of the full length protein, and includes the acidic domain, Basic I, and the HMG box (see Seq. ID No. 7).

The latter domain comprises a region having interesting homologies to other proteins that recognize altered DNA structures, and thus is considered to be the domain of SSRP most likely to contain the site which selectively recognizes and binds to the 1,2-intrastrand dinucleotide structural motif produced by the interaction of cis-DDP with DNA. Proteins found to have sequence homology to SSRP include the high mobility group (HMG) proteins 1 and 2. Eink, L. and Bustin, M. (1985) *Exp. Cell Res.* 156:295-310; Bustin, M., Lehn, D. A. and Landsman, D. (1990) *Biochim. Biophys, Acta* 1049:231-243; van Holde, K. E., in *Chromatin,* Springer-Verlag, N.Y. (1988). Homology is also observed with the HMG-box domain in human upstream binding factor (hUBF), which activates transcription of RNA polymerase I. Jantzen, H. M., Admon, A., Bell, S. and Tijan, R. (1990) *Nature* 344:830-836. Other recently identified HMG-box proteins include sex-determining region Y (SRY) (Sinclair, A. H., Berta, P., Palmer, M. S., Hawkins, J. R., Griffiths, B. L., Smith, M. J., Foster, J. W., Frischauf, A. M., Lovell-Badge, R. and Goodfellow, P. N. (1990) *Nature* 346:240-244; Gubbay, J., Collignon, J., Koopman, P., Capel, B., Economou, A., Munsterberg, A., Vivian, N., Goddfellow, P. and Lovell-Badge, R. (1990) *Nature* 346:245-250), mitochondrial transcription factor II (Parisi, M. A. and Clayton, D. A. (1991) *Science* 25:965-968), lymphoid enhancer binding factor I (Lef-1) (Travis, A., Amsterdam, A., Belanger, C. and Grosschedl, R. (1991) *Genes & Dev.* 5:880-894), a T-cell specific transcription factor (TCF-1α) (Waterman, M. L., Fischer, W. H. and Jones, K. A. (1991) *Genes & Dev.* 5:656-669), and the yeast autonomously replicating sequence factor ABF2 (Diffley, J. F. X. and Stillman, B. (1991) *Proc. Nat. Acad. Sci. USA* 88:7864-7868). A particularly interesting report is that of Shirakata, M., Hüppi, K., Usuda, S., Okazaki, K., Yoshida, K. and Sakano, H. (1991) *Mol. Cell. Biol.* 11:4528-4536, wherein the cloning of a mouse cDNA encoding an expression product capable of binding to V(D)J recombination signal sequence (RSS) probes is disclosed. The sequence of the protein encoded by this murine cDNA is 95.5% homologous to that of the human SSRP; presumptively, it is the murine homolog of SSRP as described herein.

An additional factor which supports the idea that the HMG-box contains the cisplatin-DNA adduct structure specific recognition site is that we have shown that HMG-1 binds strongly and specifically to cisplatin-modified oligonucleotides. Furthermore, Scovell, W. M. (1989) *J. Macromol. Sci. -Chem.* A26:455-480 and Hayes, J. J. and Scovell, W. M. (1991) *Biochim. Biophys. Acta* 1088:413-418 have concluded that cisplatin forms covalent cross-links between DNA and the proteins HMG-1 and -2. The biological relevance of this emerging family of HMG-box proteins, and of SSRP in particular, is discussed more fully below.

Evolutionary Conservation of the Eukaryotic SSRP gene

A Southern blot study was carried out with the object of determining the extent of evolutionary conservation of the DNA structure specific recognition protein described herein. For this purpose, a "zoo" blot comprising electrophoretically resolved DNA from a large number of species (generously donated by Dr. Paula Fracasso, in the laboratory of Professor David E. Housman, MIT) was probed with the 1.44 kb human cDNA clone, λPt2 (Seq. ID No. 9). Homologous sequences were observed in DNA derived from chimpanzee, monkey, elephant, pig, dog, rabbit, mouse, opossum, chicken, fish, and the fruitfly, *Drosophila melanogaster.* Conversely, no hybridization was observed to DNA prepared from the nematode *Caenorhabditis elegans,* yeast, the parasite Giardia (which retains both prokaryotic and eukaryotic characteristics), or the prokaryotic organisms Pseudomonas and Streptomyces.

Identification and Characterization of a Full-length *Drosophila melanogaster* SSRP cDNA Sequence The studies presented herein demonstrated clearly that cis-DDP SSRP was evolutionarily conserved at least among mammalian species, such as humans and rodents (J. H. Toney, et al., *Proc. Natl. Acad. Sci. USA* 86:8328 (1989); Shirakata, M., Hüppi, K., Usuda, S., Okazaki, K., Yoshida, K. and Sakano, H. (1991) *Mol. Cell. Biol.* 11:4528-4536), and that homologs exist in several other vertebrate species (see preceeding section). The presence of an SSRP homolog in the invertebrate fruit fly, *Drosophila melanogaster,* was of particular interest. Since regions of proteins that remain intact through evolutionary distance are generally critical for functional activity, the cloning of homologs from lower species often sheds light on the cellular role of the protein. For this reason, a low stringency screen of a Drosophila head cDNA library was conducted by using the original human cDNA clone λPt2 as a probe (described below in Example T). From the pool of ten clones originally isolated, two cDNA clones were chosen for further study (see Example U). Sequence analysis of these clones, denoted DM 3002 and DM 1001, revealed a significant region of overlap. Within these cDNAs is contained all of the coding sequence of the Drosophila protein (shown in Seq. ID Nos. 10 and 11). These findings are discussed more fully below in Example V.

Figure 16:
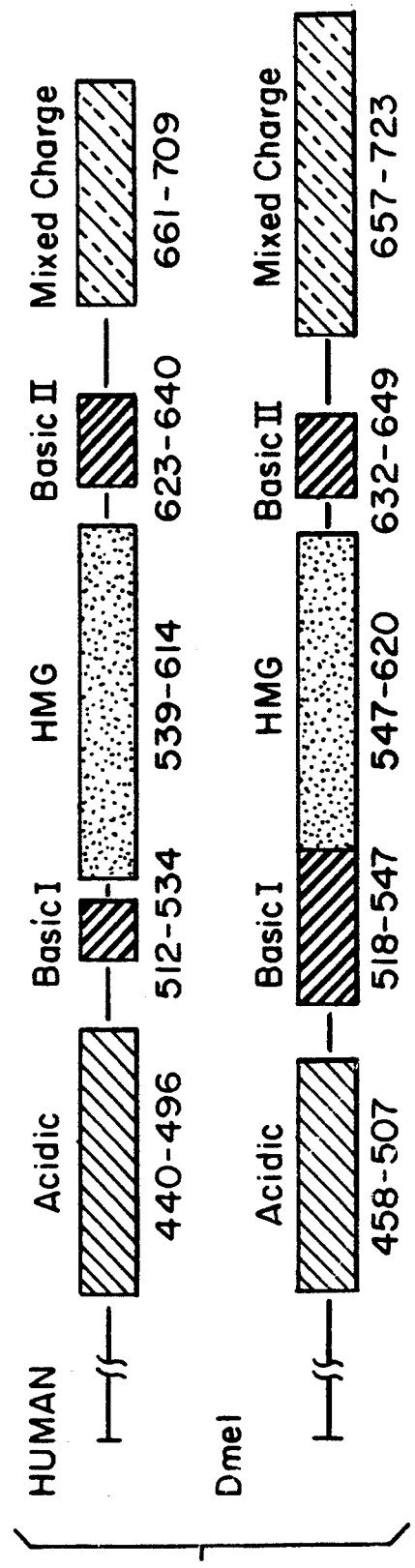
FIG. 16 is a schematic illustration, prepared from the predicted amino acid sequences of the human and the D. melanogaster (Dmel) SSRP genes (Seq. ID Nos. 7 and 11, respectively) illustrated in FIG. 15, showing various domains of the structure-specific recognition protein homologs.

The human DNA structure-specific recognition protein and its Drosophila counterpart share extensive homology at both the DNA (Seq. ID Nos. 6 and 10) and protein (Seq. ID Nos. 7 and 11) level. Both proteins contain a high percentage of charged amino acids that are concentrated within a few domains (illustrated in FIG. 16). Sequence analysis revealed that both proteins can potentially undergo a high degree of post-translational modification, with several phosphorylaton and one glycosylation site conserved between species. As noted previously in connection with the human protein, both the human and the Drosophila homologs of SSRP share homology with high mobility group proteins 1 and 2, with hUBF (a transcription factor containing an HMG-box domain) and with the transcriptional activator nucleolin. With great interest, it was observed that the structure of cis-DDP structure-specific recognition protein has also been conserved through evolution: FIG. 16 shows that all charged domains and the HMG-box are located in the same relative positions in the human and the fly. These domains in the carboxy terminal half of the protein are clearly critical for the function of this structure-recognition factor, but it is important to note that extensive homology also exists in the less well understood amino terminal portion. As discussed more fully below, the dramatically high level of evolutionary conservation of this protein strongly supports the idea that it must provide a crucial intracellular function.

Identification and Characterization of a *Saccharomyces cerevisiae* protein having cis-DDP SSRP-like Activity; Isolation of a cDNA Sequence Encoding Same The yeast, *S. cerevisiae*, provides an excellent lower eukaryotic model system, especially for studies involving molecular genetic techniques to dissect the possible in vivo functions of SSRP. As discussed briefly above, a Southern blotting approach failed to reveal the presence of a yeast gene homologous to the human SSRP gene sequence encoded by clone λPt2 (Seq. ID No. 9). However, EMSA and Southwestern blotting investigations revealed the existence of at least one yeast cellular protein having cis-DDP SSRP-like activity. As discussed in Example Y, a Pt-DNA binding factor has now been purified from yeast whole cell extracts (YWCE); this has yielded samples enriched in SSRP specific activity, as assessed by EMSA or bandshift analysis.

A Southwestern blot analysis of pooled bandshift active fractions from an S-Sepharose column corroborated that some active proteins appear to be enriched, relative to YWCE. In the first peak of bandshift activity, both a 42 000 and a 40 000 dalton protein are present. In the second peak of activity, these two proteins are also enriched, as well an 82 300 dalton protein and two smaller proteins of approximately 30 000 and 25 000 daltons.

Bandshift activity that did not bind to a DEAE-sepharose column yields a similar modified Western blot banding pattern as the second peak of bandshift-active proteins. It should be noted that, at present, it is difficult to correlate bandshift activity with Southwestern blotting results. However, it seems quite possible that several proteins are responsible for the observed bandshift activity. The small size of the known yeast proteins containing HMG-box domains, namely ABF2 (20 000 daltons) and NHP6 (11 400 daltons) has resulted in these proteins running off of the gels. (Kolodrubetz D. and A. Burgem (1990) *Journal of Biological Chemistry* 265(6):3234–3239; Diffley J. F. X. and S. B. (1991) *Proceedings National Academy of Science, USA* 88:7864–7868). Thus, the proteins that are observed in Southwestern blots may be known proteins, or may be entirely novel. It is important to note that, in studies geared toward assessing the specificity of these proteins for platinated DNA structural motifs, it has been shown that the yeast proteins possess a binding specificity pattern similar to that found in HeLa extracts (see above). Therefore, SSRPs present in yeast and humans may have similar biological relevance.

Accordingly, a yeast genomic expression library was screened for the presence of expressed polypeptides capable of binding to a radiolabelled, platinated DNA fragment in the same manner as the above-discussed screening procedure which resulted in the isolation of the human cDNA clones λPt1 (Seq. ID No. 8) and λPt2 (Seq. ID No. 9) from a human B cell expression library. This approach was successful: it resulted in the isolation of a single clone, λyPt (Seq. ID No. 12), encoding a polypeptide having cis-DDP SSRP-like activity. The cloning and sequencing of this gene are described more fully below in Example AA.

Northern blot analysis of total yeast RNA, using radiolabelled λyPt (Seq. ID No. 12) as a probe, demonstrated that the cloned DNA encodes a transcribed gene, resulting in a 2.1 kB mRNA. A translated protein of ~78 kDa might possibly result from a mRNA of this size, thus the ySSRP is presumed at present to be the 82 000 dalton protein observed in Southwestern blots. It is important to note that since the open-reading frame contained within the λyPt sequence (discussed below) is 1.63 kB, approximately 0.5 kB of sequence is missing from the 5' end of the gene.

A homology search with the partial or fractional ySSRP sequence encoded by clone λyPt (Seq. ID No. 13) resulted in the identification of regions of homology with numerous glutamine rich proteins. Interestingly, the polyglutamine region of transcription factor Sp1 is required for protein-protein interactions. Courey, A. J., D. A. Holtzman et al. (1989) *Cell* 59:827–836. A search limited to the non-glutamine rich portion of ySSRP (Seq. ID No. 13), residues 282–510, yields a much more limited set of proteins. Almost all of these proteins belong to the recently discovered and rapidly growing class of proteins which contain the HMG-box domain. The highest degree of similarity is found to the yeast protein ABF2. ABF2 is contains two HMG-boxes is highly related (37% identical, 65% similar) to ySSRP over 151 of its 183 amino acids. ABF2 binds to ARS1 domains that do not demonstrate consensus DNA sequences. Based on this fact, it has been suggested that ABF2 recognizes DNA structural features. Diffley, J. F. X. and S. B. (1991) *Proc. Nat. Acad. Sci. USA* 88:7864–7868). Thus, like ABF2, ySSRP may also be recognizing DNA structures.

Sequence homology of ySSRP (Seq. ID No. 13) to the predicted amino acid sequence of the human SSRP (Seq. ID No. 9) is rather low, with only 12.7% identity and 38% similarity found with an optimal alignment. Moreover, alignment with the *D. melangaster* SSRP reveals the same level of homology (14.5% identical, 38% similar) to the yeast protein. Yeast ySSRP, like human SSRP, does contain HMG-box domains towards its carboxy terminus. Thus, this region is probably important for DNA structural motif recognition. The high glutamine content of the remainder of the ySSRP sequence suggests that it may be important in protein-protein interactions, or in protein oligomerization. This hypothesis may be enlarged to the human SSRP.

Functional Significance of SSRP

At present, the precise nature of the in vivo role of cis-DDP SSRP is unknown; however, mounting circumstantial evidence has been presented that it may play a significant part in the initiation or control of cellular processes responsive to specific DNA structural motifs. Thus, one possible role is to recognize sites of DNA damage as a signaling event for DNA repair. A current model for recognition of DNA damage by the *E. coli* ABC excision system is that UvrA forms a complex with UvrB, either in solution or after it has bound to DNA at a site of damage. Orren, D. K. & Sancar, A. (1989) *Proc. Natl. Acad. Sci. U.S.A.* 86: 5237–5241. UvrA then dissociates from DNA, and UvrB, in conjunction with UvrC, excises an oligonucleotide encompassing the damage. The resulting gap is then filled in with the correct nucleotides by DNA polymerase. It is reasonable to surmise, then, that if this model of the *E. coli* excision repair system is valid and if it can be extrapolated to eukaryotic DNA excision repair, SSRP may function in a manner analogous to UvrA.

Regardless of whether this proposed in vivo role for SSRP is ultimately substantiated, the fact remains that cis-DDP SSRP has been demonstrated to possess the highly interesting and significant ability to bind selectively to a DNA structural motif produced by the DNA adducts of chemotherapeutically active platinum drugs, but not the adducts of two clinically ineffective platinum compounds. Moreover, the specific adducts recognized by SSRP (1,2-intrastrand dinucleotide adducts) comprise 90% of all cisplatin-DNA structures formed in vivo. These facts strongly support the conclusion that SSRP plays an important role in cellular recognition of, and response to, the presence of certain DNA structural motifs including those associated with DNA damage or lesions.

It thus is reasonable to propose that if SSRP is a component of a repair complex, it will facilitate the antitumor effectiveness of cisplatin. For example, if tumor cells were deficient, relative to nontumor cells, in their ability to repair platinum-damaged DNA, the platinum drug would be selectively lethal to tumor cells, whereas repair-proficient surrounding cells would remove platinum adducts from their DNA and hence survive. This model, however, does not account for the anticancer utility of certain platinum drugs, such as $\{Pt(NH_3)_2(N3\text{-cytosine})\}^{+2}$, although it has been proposed that the latter compound could act through a different mechanism than cis-DDP.

Alternatively, SSRP may not be involved in DNA repair at all. It may actually impede DNA repair by binding to the 1,2-intrastrand d(GpG) and d(ApG) adducts of cis-DDP, thereby shielding these adducts from the DNA repair machinery. Donahue, B. A., Augot, M., Bellon, S. F., Treiber, D. K., Toney, J. H., Lippard, S. J. and Essigmann, J. M. (1990) Biochemistry 29:5872-5880. This proposed in vivo role for SSRP is consistent with its observed pattern of gene expression in different tissues, and in several cancer cell lines, including cisplatin-resistant cell lines.

Still another possibility is that the normal role of SSRP is to regulate the function of genes implicated in the emergence of malignancies, or conversely in the maintenance of normal phenotypes. Platinum adducts, by providing DNA structural motifs which mimic those of the natural regulatory sequences of such genes, would displace SSRP from its normal DNA binding sites, thereby effectively sequestering the protein. Donahue, B. A., Augot, M., Bellon, S. F., Treiber, D. K., Toney, J. H., Lippard, S. J. and Essigmann, J. M. (1990) Biochemistry 29:5872-5880; Scovell, W. M. (1989) J. Macromol. Sci.-Chem. A26:455-480. It follows that, if tumor cells had lost the ability to compensate for this effect, cis-DDP would selectively compromise the welfare of tumor cells.

As discussed previously, SSRP as described herein is a protein that recognizes a DNA structural motif comprising the 1,2-intrastrand dinucleotide adducts which are the predominant drug-DNA adducts formed as a result of the interaction of cis-DDP with DNA. These intrastrand d(GpG) and d(ApG) cross-links unwind the DNA duplex by 13° and cause a 34° bend in the direction of the major groove. Churchill, M. E. A. and Travers, A. A. (1991) TIBS 16:92-97; Bellon, S. F. and Lippard, S. J. (1990) Biophys. Chem. 35:179-188; Rice, J. A., Crothers, D. M., Pinto, A. L. and Lippard, S. J. (1988) Proc. Nat. Acad. Sci. USA 85:4158-4161. Important clues for identifying the type of protein that might interact with such an altered structure are provided by the striking homology of the human SSRP (Seq. ID No. 7) to HMG-1, which is known to bind cruciform DNA (Bianchi, M. E., Beltrame, M. and Paonessa, G. (1989) Science 243:1056-1058), and the near identity, at the protein sequence level, of the human SSRP (Seq. I.D. No. 7) disclosed herein and a mouse protein which has been reported to bind to signal sequences for V(D)J recombination. Shirakata, M., Hüppi, K., Usuda, S., Okazaki, K., Yoshida, K. and Sakano, H. (1991) Mol. Cell. Biol. 11:4528-4536. The common DNA structural element recognized by SSRP and HMG-1, while not yet defined, most likely mimics the unwinding and bending known to occur in cisplatin-modified DNA. Taken together, the observed properties of SSRP raise the possibility that HMG-1, the family of HMG-box proteins, and recombination functions may be involved in the molecular mechanism of the effective antitumor drug, cisplatin.

Homology between SSRP as described herein and HMG-1 and -2 is particularly interesting because the latter proteins can also specifically recognize structural distortions to DNA such as B-Z junctions and cruciforms (H. Hamada and M. Bustin, Biochemistry, 24:1428 (1985); Bianchi, M. E., et al., Science 243:1056 (1989)). They too are evolutionarily conserved, with homologs known in human (L. Wen, et al., Nucl. Acids. Res., 17:1197 (1989)), bovine (B. Pentecost and G. H. Dixon, Biosci. Rep., 4:49 (1984); D. J. Kaplan and C. H. Duncan, Nucl. Acids Res., 16:.10375 (1988), porcine (K. Tsuda, et al., Biochemistry, 27:6159 (1988)), rodent (G. Paonessa, et al., Nucl. Acids Res., 15:9077 (1987); K. -L. D., Lee, et al., Nucl. Acids Res., 15:5051 (1987)), fish (B. T. Pentecost, et al., Nucl. Acids Res., 13:4871 (1985)), yeast (D. Kolodrubetz and A. Burgum, J. Biol. Chem., 265:3234 (1990), maize (K. D. Grasser and G. Feix, Nucl. Acids RES., 19:2573 (1991)), and protazoa (S. Y. Roth, et al., Nucl. Acids Res., 15:8112 (1987); T. Hayashi, et al., J. Biochem., 105:577 (1989)). Many studies support a role for HMG-1 and -2 in DNA processing, particularly in transcriptional regulation. They influence transcription of RNA polymerase II and III by altering the DNase I footprint of the major late transcription factor, presumably by conferring a structure to the binding site which optimized the process (D. J. Tremethick and P. L. Molloy, J. Bio. Chem., 261:6986 (1986); F. Watt and P. L. Molloy, Nucl. Acids Res., 16:1471 (1988)). HMG-1 has also been shown to modify DNA structures, such as B-Z junctions and cruciforms, in in vitro transcription assays, thereby permitting transcription to proceed past these structural blocks (S. Waga, et al., Biochem. and Biophys. Res. Comm., 153:334 (1988); S. Waga, et al., J. Biol. Chem., 265:19424 (1990)). Other work has suggested that HMG-1 and -2 can act as general class II transcription factors, and may be tightly associated with or identical to transcription factor IIB (J. Singh and G. H. Dixon, Biochemistry, 29:6295 (1990)).

These studies, taken together, suggest that HMG-1 and -2 act to facilitate transcription by binding to specific DNA conformations to create or preserve structures necessary for transcription initiation. A salient feature of the cDNA clones identified as encoding SSRP is that each includes the region of nucleotide sequence identified as an HMG box domain. HMG box domains are emerging as an important recognition element of proteins for DNA. Deletion analysis of HMG-box family members hUBF (Jantzen, H. M., Admon, A., Bell, S. and Tijan, R. (1990) Nature 344:830-836) and TCF-1α (Waterman, M. L., Fischer, W. H. and Jones, K. A. (1991) Genes & Dev. 5:656-669) has demonstrated that a single HMG-box domain is sufficient for the specific interactions of these proteins with DNA. It is important to note, however, that in spite of the emergence of several proteins identified as HMG-box family members, a consensus sequence has not yet emerged for the HMG box domain. Lack of a clearly defined consensus sequence among the HMG-box domains in a variety of proteins may indicate either that such proteins recognize different DNA structures, or that they do not share a common mode of DNA recognition. Whereas mutations in the sequences of target recognition sites in DNA alter binding of the HMG-box proteins, such changes could also modify the shape of the recognition site, reducing its protein affinity. The suggestion (Diffley, J. F. X. and Stillman, B. (1991) Proc. Nat. Acad. Sci. USA 88:7864-7868) that HMG-box proteins recognize DNA structure rather than sequence is strongly supported by the observations reported herein, that SSRP binds selectively to cisplatin-modified DNA fragments, but not to unmodified fragments having the same sequence.

Other properties of HMG-1 are fully consistent with its role in binding to altered DNA structures. For example, HMG-1 suppresses nucleosome core particle formation (Waga, S., Mizuno, S. and Yoshida, M. (1989) Biochim. Biophys. Acta 1007:209-214), and it can selectively unwind negatively supercoiled DNA, thereby protecting it from relaxation by E. coli topoisomerase I and preventing the formation of higher order secondary structure (Sheflin, L. G. and Spaulding, S. W. (1989) Biochem. 28:5658-5664). It binds preferentially to A-T rich regions (Reeves, R. and Nissen, M. S. (1990) J. Biol. Sciences 265:8573-8582), single stranded DNA (Isackson, P. J., Fishback, J. L., Bidney, D. L. and Reeck, G. R. (1979) J. Biol. Chem. 254:5569-5572), B-Z junctions (Hamada, H. and Bustin, M. (1985) Biochem. 24:1428-1433), and to cruciform structures (Bianchi, M. E., Beltrame, M. and Paonessa, G. (1989) Science 243:1056-1058). Moreover, studies of plasmid DNA containing a number of structural domains suggest that HMG-1 can differentiate among various DNA conformations (Hamada, H. and Bustin, M. (1985) Biochem. 24:1428-1433) .

Of particular interest are several studies which suggest that HMG-1 and -2 act by binding to specific structural elements in DNA upstream from actively transcribed genes to preserve conformations necessary for the binding of sequence-specific transcription factors. Tremethick, D. J. and Molloy, P. L. (1986) J. Biol. Chem. 261:6986-6992; Tremethick, D. J. and Molloy, P. L. (1988) Nucl. Acids Res. 16:1471-1486; Watt, F. and Molloy, P. L. (1988) Nucl. Acids Res. 16:1471-1486; Waga, S., Mizuno, S. and Yoshida, M. (1988) Biochem. Biophys. Res. Comm. 153:334-339; Singh, J. and Dixon, G. H. (1990) Biochem. 29:6295-6302. In particular, HMG-1 removes the transcriptional block caused by cruciforms in supercoiled DNA. Waga, S., Mizuno. S. and Yoshida, M. (1990) J. Biol. Chem. 265:19424-19428. Eukaryotic DNA contains palindromic sequences that form cruciform structures, which may in turn have elements in common with the 1,2-intrastrand d(ApG) and d(GpG) adducts formed by cisplatin modified DNA.

Additional insights into the possible in vivo role of cis-DDP SSRP are provided by the recent characterization of a mouse cDNA clone isolated by screening an expression library with oligonucleotides containing recombination signal sequences (RSS). Shirakata, M., Hüppi, K., Usuda, S., Okazaki, K., Yoshida, K. and Sakano, H. (1991) Mol. Cell. Biol. 11:4528-4536. RSS sequences are signals for somatic DNA recombination to generate antibody diversity through V(D)J joining. The predicted amino acid sequence of this mouse protein is 95.5% identical with that of the human SSRP (Seq. ID No. 7) described herein. Therefore, it is presumed to be encoded by the mouse homolog of the human and Drosophila SSRP genes (Seq. ID Nos. 6 and 7) as disclosed herein. Interestingly, V(D)J recombination is postulated to proceed via stem-loop structures formed by RSS sequences (Max, E. E., Seidman, J. G. and Leder, P. (1979) Proc. Nat. Acad. Sci. USA 76:3450-3454; Sakano, H., Hüppi, K., Heinrich, G., and Tonegawa, S. (1979) Nature 280:88-94; Early, P., Huang, H., Davis, M., Calame, K. and Hood, L. (1980) Cell 19:981-992; Tonegawa, S. (1983) Nature 302:575-581), although this model has been challenged (Hesse, J. E., Lieber, M. R., Mizuuchi, K. and Gellert, M. (1989) Genes & Dev. 3:1053-1061). The similarity among stem-loop DNA, cruciforms recognized by HMG-1, and the bent, unwound cisplatin-DNA 1,2-intrastrand cross-link structural motif is intriging and supports the postulate that binding of the mouse HMG-box protein reported by Shirakata et al. to RSS involves shape as well as sequence recognition.

When the present invention is viewed in the context of the foregoing remarks, it will be apparent that SSRP, and possibly other HMG-box proteins, may be diverted or sequestered from their normal regulatory intracellular roles by the presence of cisplatin-DNA adducts, and that somatic DNA recombination and transcription are specific cellular functions likely to be affected by the platinum anticancer drug family. Understanding the shape recognition elements of these proteins may provide a basis for the design of future generations of rationally designed chemotherapeutic agents.

Use of SSRP for Diagnostic, Therapeutic and Prophylactic Purposes

As a result of the discovery embodied in this invention, new diagnostic tools are available, including, for example, nucleotide probes and antibodies which are useful for detecting the presence or absence of SSRP and/or of the gene or portion thereof which encodes SSRP. Antibodies prepared against the SSRP, or DNA or RNA probes which bind to DNA encoding the SSRP, may be useful for classifying the responsiveness of humans or animals to DNA damaging agents. Antibodies against the DNA structure-specific recognition factor described herein have been generated by injecting a fusion protein (β-galactosidase-λPt2) (Seq. ID No. 9) into rabbits, in whom specific polyclonal antibodies were subsequently produced. These antibodies have been shown by Western blot analysis to bind the λPt2 fusion protein.

These diagnostic tools can be used, for example, in prenatal screening. Thus, prenatal genetic screening for known genetic defects or genetic characteristics associated with particular diseases can now include assessment of the absence of SSRP, or of its occurrence at altered (e.g., lowered) levels. Absence or abnormal (e.g., subnormal) expression of the SSRP is putatively indicative of the likelihood that the individual tested will develop cancer during life.

The invention described herein also makes possible the production of a therapeutic agent useful in protecting an individual against DNA damage, or in countering DNA damage that has already occurred. For example, a therapeutic agent protective against the DNA structural or chemical damage caused by chemotherapy or radiotherapy can be administered to an individual prior to therapy, at the time of therapy (e.g., in the course of treatment of humans with radiation or with the anticancer drug cisplatin), or after such treatment has been undergone. The agent will protect against damage to DNA by creating a DNA damage-refractory phenotype.

A further result of the present invention is that gene therapy or gene replacement will be available to individuals lacking SSRP or having less than normal expression levels of the factor. In such a case, DNA encoding SSRP can be administered to individuals by means of, for example, genetically-engineered vectors that contain the factor-encoding DNA and regulatory and expression components necessary for its expression. Such recombinant vectors can be used, for example, to infect undifferentiated cells in situ in the individual. The resultant cells express the encoded factor (SSRP), thereby overcoming the shortage or lack of natural DNA structure-specific recognition protein production in the individual.

The present invention will now be illustrated by the following examples, which are not to be considered limiting in any way.

EXAMPLE A

Electrophoretic Mobility Shift Analysis (EMSA) of the DNA binding Characteristics of the Cellular cis-DDP Structure-Specific Recognition Protein (cis-DDP SSRP)

Materials

Restriction endonucleases and polynucleotide kinase were purchased from New England Biolabs. The Klenow fragment of *E. coli* polymerase I and bacteriophage T4 DNA ligase (Boehringer Mannheim Biochemicals), proteinase K and RNase A (Sigma), (hexamethyldecyl)-trimethylammonium bromide (CTAB) (Fluka), and poly(dI-dC)•poly(dI-dC) (Pharmacia) were obtained from commercial sources as indicated. The cell lines used were HeLa (kindly provided by M. Chow, MIT), cis-DDP-resistant HeLa, Chinese hamster V79, and cis-DDP-resistant V79 cells (kindly provided by S. L. Bruhn, MIT; cis-DDP resistant V79 cells were adapted to 15 $\mu$g/mL cisplatin, making them about 30-fold more resistant than parental cells), and human B cells (RPMI 4265; kindly provided by H. Singh, MIT).

Cell Extracts

Cytosolic, nuclear and whole-cell extracts were prepared according to published procedures. Stillman, B. W. and Y. Gluzman, *Mol. Cell. Biol.* 5:2051-2060 (1985); Dignam et al., *Nucleic Acids Res.* 13:1475-1489 (1983); and Wood et al., *Cell* 53:97-106 (1983), respectively. Protein concentrations were determined by the method of Bradford. Bradford, *Anal. Biochem.* 72:248-254 (1976).

Platinum-Modified Damaged DNA Fragments cis-DDP, trans-DDP, [Pt(en)Cl$_2$], and [Pt(dien)Cl]Cl were prepared as described (Johnson, G. L. *Inorg. Synth.* 8:242-244 (1966); Dhara, S. C., *Indian J. Chem.* 8:193-194 (1970); Watt, G. W. and W. A. Cude, *Inorg. Chem.* 7:335-338 (1968); Lippard et al., *Biochemistry* 22:5165-5168 (1983). Restriction fragments, a 274 bp ClaI-SmaI fragment generated from pSTR3 (see Couto et al., *J. Bacteriol.* 171:4170-4177 (1989)) and a 422 bp AvaI fragment generated from bacteriophage M13mp18 DNA, were purified on low melting point agarose electrophoresis gels followed by phenol extraction (Maniatis et al., *Molecular Cloning, A Laboratory Manual*, Cold Spring Harbor Laboratory, Cold Spring Harbor, N.Y. (1982)) or butanol extraction in the presence of CTAB (Langridge et al., *Anal. Biochem.* 103:264-271 (1980)).

Restriction fragments were suspended in 1 mM sodium phosphate buffer, pH 7.4, containing 3 mM NaCl (buffer B) or in TE at a DNA nucleotide concentration of about 10$^{-4}$M. A portion of the DNA was allowed to react with the appropriate platinum complex at a variety of formal drug/nucleotide ratios at 37° C. for 12-24 hours. An identical volume of buffer B or TE was added to control, unmodified DNA and incubated in parallel with the modified DNA fragment. Unbound platinum was removed by ethanol precipitation of the Pt-modified DNA restriction fragments, followed by several washes of the pellet with 80% ethanol. DNA concentrations were determined by UV spectroscopy with the relation 1 OD$_{260}$=50 $\mu$g/mL. Bound levels of Pt to DNA were measured on a Varian AA-1475 atomic absorption spectrometer equipped with a GTA-95 graphite furnace. DNA fragments were radiolabelled with [$\alpha$-$^{32}$P]dCTP (>5000 Ci/mmol, New England Nuclear) by the Klenow fragment of DNA polymerase I. Labeled, damaged DNA fragments were purified on native polyacrylamide gels as described in Maniatis et al., *Molecular Cloning, A Laboratory Manual*, Cold Spring Harbor Laboratory, Cold Spring Harbor, N.Y. 1982) and resuspended in TE to 5000 cpm/$\mu$L prior to use in EMSA or other studies.

Electrophoretic Gel Mobility Shift Assay (EMSA or Bandshift Analysis)

Studies of (damaged DNA fragment):(protein) complexes formed as a result of binding of SSRP to radiolabelled, platinated DNA fragments with the use of gel electrophoresis was carried out as described by Carthew et al. *Cell* 43:439-448 (1985) with minor modifications. End-radiolabeled DNA restriction fragments [(1-5)×10$^3$ cpm; ~0.2 ng] that were either unmodified or modified with the various platinum compounds as indicated below were incubated in the presence of crude extracts, typically 5-10 $\mu$g of protein, and 6 $\mu$g of competitor poly(dI-dC)•poly(dI-dC) for 15 minutes at 37° C. in binding buffer (10 mM Tris-HCl, pH 7.5, 50 mM NaCl, 0.5 mM Na$_2$EDTA, 5% glycerol, and 1 mM DTT) in a final volume of 10-50 $\mu$L.

(Damaged DNA fragment):(protein) complexes were thereafter resolved from uncomplexed DNA fragments on a 4% polyacrylamide gel [29:1 acrylamide:N,N'-methylene-bis(acrylamide)]. Gels were preelectrophoresed in Tris-glycine buffer (50 mM Tris-HCl, pH 8.5, 380 mM glycine, 2 mM Na$_2$EDTA) for >1 hour at 25 mA. Samples were then electrophoresed for about 4 hours at 30 mA. Gels were dried and autoradiographed overnight at 20° C. with an intensifying screen.

In FIG. 1, results are shown of a study showing the binding of a cellular protein to a damaged DNA fragment comprising a radiolabelled, cis-DDP modified 422 bp AvaI restriction fragment of M13mp18 DNA. Radiolabelled DNA fragments (1-5×10$^3$ cpm; 0.2 ng) contained bound cis-DDP levels as follows: lanes 1-4, r$_b$ of 0; lanes 5-8, r$_b$ of 0.007; lanes 9-12, r$_b$ of 0.021; lanes 13-16, r$_b$ of 0.041; and lanes 17-20, r$_b$ of 0.061. These radiolabelled, platinum damaged DNA fragments were incubated in the absence (−; lanes 1, 5, 9, 13 and 17) or presence of crude nuclear extract prepared from V79 parental cells (VP; lanes 2, 6, 10, 14 and 18), cis-DDP-resistant V79 cells (VR; lanes 3, 7, 11, 15 and 19) or HeLa cells (H; lanes 4, 8, 12, 16 and 20). It can be seen from the autoradiograph presented in FIG. 1 that migration of the DNA fragment alone is retarded with increasing levels of modification (lanes 1, 5, 9, 13 and 17), owing to increased positive charge and increased structural alterations of the DNA as a result of cis-DDP binding. Sherman, S. E., and S. J. Lippard, *Chem. Rev.*, 87:1153–1181 (1987). It can also be seen that cellular factors present in HeLa nuclear extract bind to unplatinated DNA (lane 4). This binding is reproducible, independent of the oligonucleotide probe, and currently of unknown origin. A second band also appears with the unplatinated DNA probe (lane 1) and probably represents denatured probe DNA.

In pertinent part, the EMSA results shown in FIG. 1 demonstrate the presence of a cellular structure-specific DNA recognition protein (SSRP) which binds selectivity to cisplatin-modified DNA. This DNA binding protein formed a (damaged DNA fragment):(protein) complex having a retarded electrophoretic migration relative to that of the damaged DNA fragment alone (e.g., lanes 1, 5, 9, 13 and 17), allowing the complex to be visualized in nuclear extracts from human HeLa and Chinese hamster V79 parental and cis-DDP-resistant cell lines. Selectivity for platinated DNA was demonstrated by the correlation between the extent of binding and the level of DNA platination. An estimated minimum modification level of about 0.007 Pt/nucleotide was required to observe binding of the protein to labeled modified DNA, whereas, at a modification level of 0.06 Pt/nucleotide, nearly all labeled DNA was complexed. For probes of higher $r_b$, two bands were observed in the gel (lanes 18–20), possibly indicating the binding of two protein molecules to those DNA fragments having higher numbers of damaged sites. In other experiments, cis-DDP-specific SSRPs were found in cytosolic extracts and whole-cell extracts prepared from HeLa cells and in nuclear extracts from human B cells. Cytosolic and whole-cell extracts from this latter source were not examined. It has not yet been conclusively established that the protein observed in cytosolic extracts is the same as that found in nuclear extracts. However, as described below, both proteins have similar specificities of binding to DNAs modified with various platinum compounds. Furthermore, both proteins are precipitated with 40–65% ammonium sulfate.

It should also be noted that the cis-DDP SSRP appears to be present at the same levels in platinum-sensitive and platinum-resistant cell lines. FIG. 1 shows that platinated DNA fragments incubated with nuclear extracts from either V79 parental or cis-DDP-resistant cell lines were bound to similar extent. Similar results were obtained with parental and approximately 50-fold cis-DDP-resistant HeLa cell extracts (data not shown). Hence, in these cell lines the level of SSRP present does not seem to be related to acquired cellular resistance to cis-DDP.

EXAMPLE B

EMSA Study of the Selectivity Characteristics of the Cellular SSRP for cis-DDP

An EMSA study was carried out with the object of assessing the ability of the SSRP disclosed in Example A to discriminate among different platinated DNA adducts. These results are presented in FIG. 2. Here, the 422 bp AvaI DNA restriction fragment described in Example A was modified with various platinum compounds and incubated in the absence (lanes 1, 5, 9, 13 and 17) or presence of crude extracts prepared from V79 parental cells (VP; lanes 2, 6, 10, 14 and 18), V79 cis-DDP-resistant cells (VR; lanes 3, 7, 11, 15 and 19) or HeLa cells (H; lanes 4, 8, 12, 16 and 20), all as described above in Example A.

The results of incubations with the radiolabelled, undamaged DNA fragment appear in lanes 1–4 of FIG. 2. The results of incubations with a radiolabelled DNA fragment modified with trans-DDP at $r_b$ levels of 0.013 and 0.064 are shown in lanes 5–8 and 9–12, respectively. Lanes 13–16 show the results of incubations with [Pt(dien)Cl]Cl at $r_b=0.071$, and lanes 17–20 show the results of incubations with cis-DDP at an $r_b$ level of 0.041. Labelled material in the wells probably consists of aggregates of the radiolabelled, Pt-modified DNA fragments. It can be seen that SSRP forms complexes only with DNA fragments containing adducts of platinum drugs which are capable of forming 1,2-intrastrand dinucleotide adducts.

EXAMPLE C

Competitive EMSA Study of the Cellular SSRP

A competition study (presented in FIG. 3) was carried out wherein protein-DNA fragment binding reactions were incubated in the presence of escalating concentrations of unlabelled DNA fragments containing or lacking sites of platinum modification. More specifically, a preparation of end-labeled 274 bp ClaI-SmaI restriction fragment generated from pSTR3 as described above in Example A (5000 cpm; 0.2 ng) was modified with cis-DDP at $r_b=0.045$. Labelled DNA fragments were incubated in the presence of 7.3 μg nuclear extract from cis-DDP-resistant V79 cells, nonspecific competitor DNA, and competitors as follows: lanes 3–6=0.2, 1, 10 and 20 ng unlabeled, unmodified 422 bp AvaI restriction fragment of M13mp18; lanes 7–10=0.2, 1, 10 and 20 ng unlabeled 422 bp fragment modified with cis-DDP at an $r_b$ level of 0.035. The unbound 274 bp fragment modified at an $r_b$ level of 0.045 is shown in lane 1, and binding of the cellular factor to this fragment in the absence of 422 bp competitor is shown in lane 2.

For comparison, end-labeled 422 bp fragment modified with cis-DDP at an $r_b$ level of 0.035 alone is shown in lane 11, and the (damaged DNA fragment):(protein) complex formed between this restriction fragment and cellular SSRP is shown in lane 12.

EXAMPLE D

EMSA Study of the Sensitivity the Cellular SSRP to Protease and Ribonucleases

A sensitivity study was designed to investigate the effects of incubation in the presence of protease or ribonuclease on the ability of the cellular SSRP to form (damaged DNA fragment):(protein) complexes. The results of the EMSA analysis presented in FIG. 4 demonstrate that the cellular factor in crude extracts was sensitive to the activity of protease and ribonucleases. Crude nuclear extracts were pretreated at 37° C. for 60 minutes in the presence or absence of enzymes as indicated in FIG. 4. The pretreated extracts were then incubated with 5000 cpm (0.2 ng) end-labeled 422 bp AvaI restriction fragment, modified with cis-DDP at an $r_b$ level of 0.041 as described in Example A. Electrophoretically resolved samples which are shown in FIG. 4 include: lane 1, free unlabeled 422 bp platinated fragment; and lane 2, extract pretreated in the absence of lytic enzymes. The remaining lanes show results with extracts pretreated as follows: lane 3 (P), proteinase K at 100 μg/mL; lane 4 (M), micrococcal nuclease at 0.075 U/mL; lane 5 (T1), RNase T1 at 0.025 U/mL; lane 6 (T2), RNase T2 at 0.005 U/mL; lanes 7–10 (R), RNase A at 20 μg/mL, 2 μg/mL, 0.2 μg/mL, and 0.02 μg/mL.

In subsequent studies, cell extracts and partially purified SSRP (described below) were incubated in the presence of proteinase K at 100 μg/mL or RNase A at 20 μg/mL for 1 hour at 37° C. in 10 mM Tris-HCl, pH 7.4, containing 1 mM Na₂EDTA, then subjected to EMSA analysis as described in Example A. The results of this study showed that pretreatment of crude extracts with proteinase K resulted in loss of binding activity, confirming that the observed factor (SSRP) is a protein. Pretreatment of crude extracts with RNase A also resulted in loss of activity, but this sensitivity disappeared after partial purification of the cis-DDP SSRP factor by ammonium sulfate fractionation and ion exchange chromatography as hereinafter described.

EXAMPLE E

EMSA Investigation of Possible Requirements of the Cellular cis-DDP SSRP for cofactors and metal ions The gel mobility shift assay was also used to assess the possible cofactor and metal ion requirements for binding of SSRP to cis-DDP-modified DNA. The factor in crude cellular extracts required neither ATP nor divalent cations such as $Mg^{2+}$ and was insensitive to EDTA at concentrations up to 100 mM. Binding activity was sensitive, however, to some metal ions. (Damaged DNA fragment):(protein) complex formation was completely inhibited in the presence of 5 mM $ZnCl_2$, $MnCl_2$, $CoCl_2$, or $CdCl_2$ and by 1 mM $HgCl_2$. The protein bound to platinated DNA at both 37 and 0° C., but heat treatment of the extracts (42° C. for 15 minutes) prior to the EMSA incubation step (see Example A) resulted in complete loss of activity. SSRP binding activity was also inhibited at high salt concentrations, such as 500 mM KCl.

EXAMPLE F

Competitive Electrophoretic Mobility Shift Analysis of the Cellular SSRP

Competition Assays

Competition assays were performed by adding various amounts of unlabeled competitor DNA to the binding reactions of the gel mobility shift assay before the 15-min incubation step described in Example A. Competitor DNA was either a restriction fragment as described above, or M13mp18RF (replicative form) DNA that was either unmodified or modified with cis-DDP or UV light.

Determination of the Binding Constant of cis-DDP SSRP

The binding constant of the protein for platinated DNA was estimated as described by Müller, R., *Methods Enzymol.* 9:589–601 (1983). A competition assay was performed in which radiolabeled 274-bp fragment modified with cis-DDP at an $r_b$ level of 0.036 (see Example A) was incubated in the presence of increasing amounts of unlabeled 274-bp fragment modified with cis-DDP to the same extent. Binding reactions were done in triplicate for each level of competitor DNA. The amount of labeled platinated DNA bound to the protein was estimated by scintillation counting of the free and bound labeled DNA excised from dried gels.

The results of these competition studies are shown in FIG. 5. Cellular SSRP binding to the labeled 274-bp fragment platinated at 0.036 Pt/nucleotide was effectively competed by increasing quantities of unlabeled fragment modified to the same extent (see lanes 6–20). By contrast, unplatinated DNA did not compete with the labelled platinated DNA for binding of the cellular factor. Competition for binding was complete when a 100-fold excess of unlabelled platinated DNA was added to the binding reaction (lanes 18–20). Binding of SSRP to labeled, platinated DNA was inhibited by 50% in the presence of a 3-fold excess of unlabeled platinated DNA.

From these results, the affinity constant of the cis-DDP SSRP could be estimated. It was assumed that bands 1–3 observed in the autoradiograph shown in FIG. 5 represented one, two, and three bound protein molecules, respectively. DNA in the well of each lane was also assumed to contain bound protein. From these data, the extent of inhibition of binding due to the competitor DNA could be calculated. The affinity constant was determined from the equation derived by Müller, R., *Methods Enzymol.* 9:589–601 (1983):

$$K = 8/3([I_t] - [T_t])$$

where $[I_t]$ represents the concentration of unlabelled platinated DNA that results in 50% inhibition of binding and $[T_t]$ represents the concentration of labeled platinated DNA. The dissociation constant ($K_d$) is the reciprocal of the binding constant (K). From the results of this competition study, $K_d$ was estimated to be about $1 \times 10^{-10}$M. This estimate, which is a lower limit, was made by assuming one binding site for each molecule of DNA. Bands 2 and 3, however, suggest that more than one protein can bind per molecule of DNA. Both the radiolabeled and unlabelled competitor DNA fragments contained an average of 20 platinum adducts. Since the cis-DDP SSRP binds only to the 1,2-d(GpG) and -d(ApG) adducts formed by cisplatin (see Example F), comprising 90% of all platinum adducts of this drug, it was assumed that each molecule of competitor DNA contained about 18 potential binding sites. When the concentrations of unlabelled and labelled binding sites were used in the above equation, the upper limit of the dissociation constant was calculated to be $2 \times 10^{-9}$M. The true value of the dissociation constant, therefore, lies in the range of $(1-20) \times 10^{-10}$M. Of course, competition assays with purified protein and probes containing single, site-specific platinum adducts can be used to determine the dissociation constant more accurately.

EXAMPLE G

EMSA Study of the Selectivity Characteristics of the Cellular SSRP for cis-DDP DNA Adducts A more refined EMSA study (presented in FIG. 6) was carried out to follow up on the results discussed in Example B and presented in FIG. 2. The 422 bp AvaI DNA restriction fragment of M13mp18 described in Example A was modified with various therapeutically active platinum compounds. HeLa extracts were prepared as described in Example A. Labelled, damaged DNA fragments were incubated in the absence of cell extract (—; lanes 1, 4, 7, 10, 13 and 16 of FIG. 6), in the presence of HeLa cytosolic extract (S; lanes 2, 5, 8, 11, 14 and 17), or in the presence of HeLa nuclear extract (N; lanes 3, 6, 9, 12, 15 and 18). Samples were incubated and electrophoretically resolved as described previously.

EMSA results are shown for incubations in the presence of unmodified 422 bp AvaI restriction fragment of M13mp18 (lanes 1-3), and for incubations in the presence of this 422 bp DNA fragment modified with the following platinum adducts: lanes 4-6, cis-DDP at an $r_b$ level of 0.038; lanes 7-9, trans-DDP at an $r_b$ level of 0.034; lanes 10-12, [Pt(en)Cl]Cl at an $r_b$ level of 0.047; lanes 13-15, [Pt(dach)Cl$_2$] at an $r_b$ level of 0.017; lanes 16-18, [Pt(dien)Cl]Cl at an $r_b$ level of 0.047.

Figure 6:
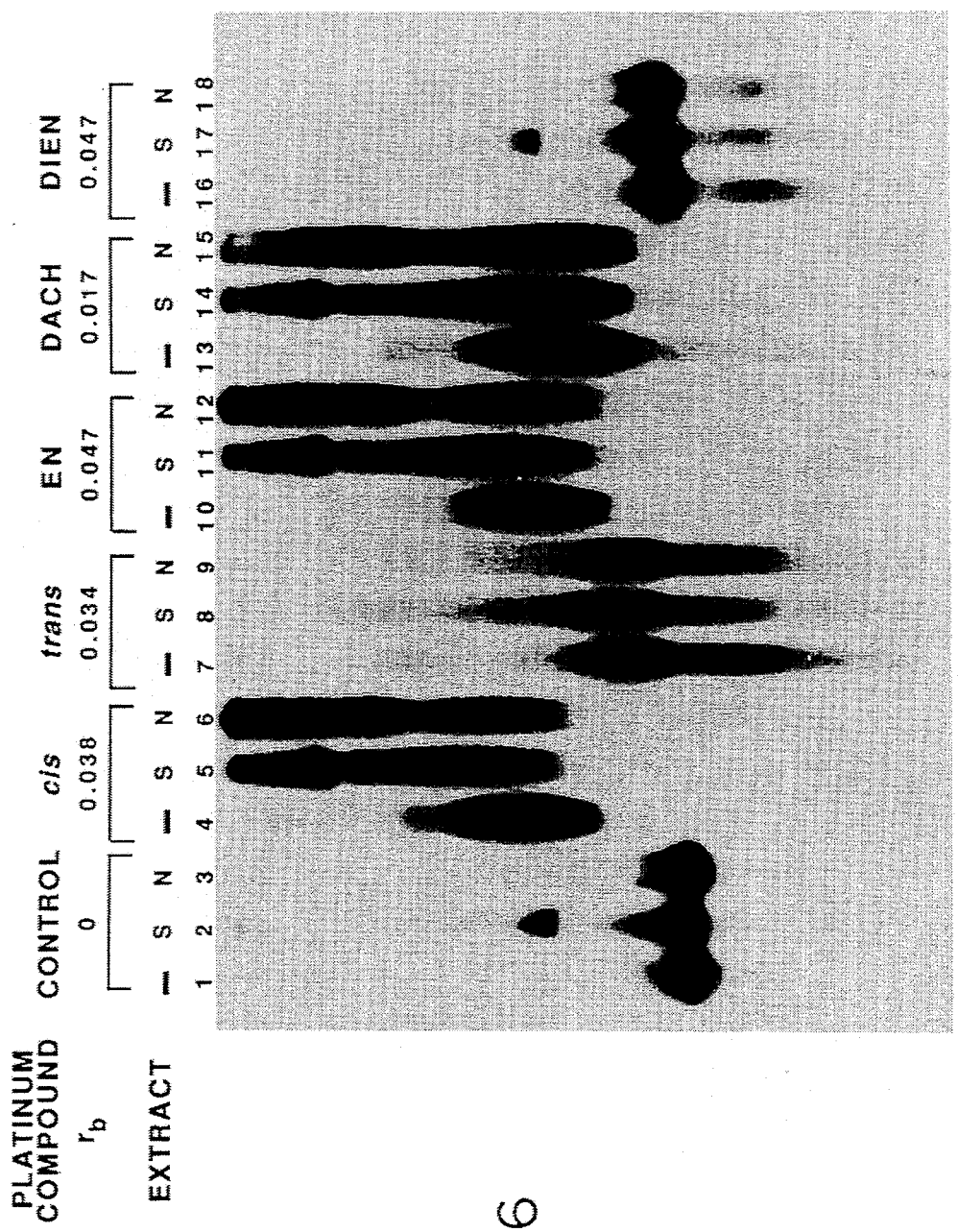
FIG. 6 is an autoradiograph of the results of an EMSA study showing the selectivity of the cellular cis-DDP SSRP for DNA structurally modified with therapeutically active platinum compounds.

FIG. 6 demonstrates that the cellular SSRP binds selectively to DNA modified with cis-DDP, [Pt(en)Cl$_2$], and [Pt(dach)Cl$_2$], but not to DNA modified with either trans-DDP or [Pt(dien(Cl)]Cl. The latter two platinum compounds are unable to link adjacent nucleotides in DNA, whereas the former three are known to form 1,2-intrastrand d(ApG) and d(GpG) adducts.

EXAMPLE H

Further EMSA Study of the Platinated DNA Structural Motif Recognized by the Cellular cis-DDP SSRP Construction of Oligonucleotides Containing Specific Platinum-DNA Adducts Oligonucleotides 22 bases in length containing single 1,2-intrastrand d(GpG) or d(ApG) or 1,3-intrastrand d(GpTpG) adducts of cis-DDP, the 1,3-intrastrand d(GpTpG) adduct of trans-DDP, or the monofunctional N7-d(G) adduct of [Pt(NH$_3$)$_2$(N3-cytosine)]$^{2+}$ were prepared as previously reported. Rice et al., *Proc. Natl. Acad. Sci. USA* 85:4158-4161 (1988). These oligonucleotides are designated as "Top" strands. Unmodified Top strands were also constructed as controls. Complementary oligonucleotides designated as "Bottom" strands were constructed such that, when annealed to the adducted single-stranded fragments, they formed duplexes containing two-base 3'-overhangs at both ends. These synthetic, double-stranded oligonucleotides containing predefined types of platinum adducts are shown in FIG. 7 and in Seq. ID Nos. 1-5.

The Bottom oligonucleotides were 5'-end labeled with [$\gamma$-$^{32}$P]ATP (<3000 Ci/mmol, New England Nuclear) by polynucleotide kinase and purified from unincorporated ATP on a Nensorb-20 column (New England Nuclear). Adducted and control Top oligonucleotides were 5'-end phosphorylated with nonradioactive ATP and also purified on Nensorb-20 columns.

Top and Bottom strands were mixed at a mole ratio of 4:3, heated at 90° C., and then cooled slowly to 4° C. to allow the two strands to anneal. High-concentration T4 DNA ligase (10,000 units/mL) was added, and the samples were incubated overnight at 13° C. Double-stranded oligonucleotides of 44, 66, 88 and 110 bp in length were then purified from native polyacrylamide gels according to the method of Maniatis (supra). These synthetic duplex oligonucleotides containing predefined, specifically placed platinated DNA structural motifs (shown in FIG. 7 and in Seq. ID Nos. 1-5) were used as damaged DNA fragments to investigate SSRP binding specificity in the competitive EMSA studies presented in FIGS. 8A-C.

Figure 8A:
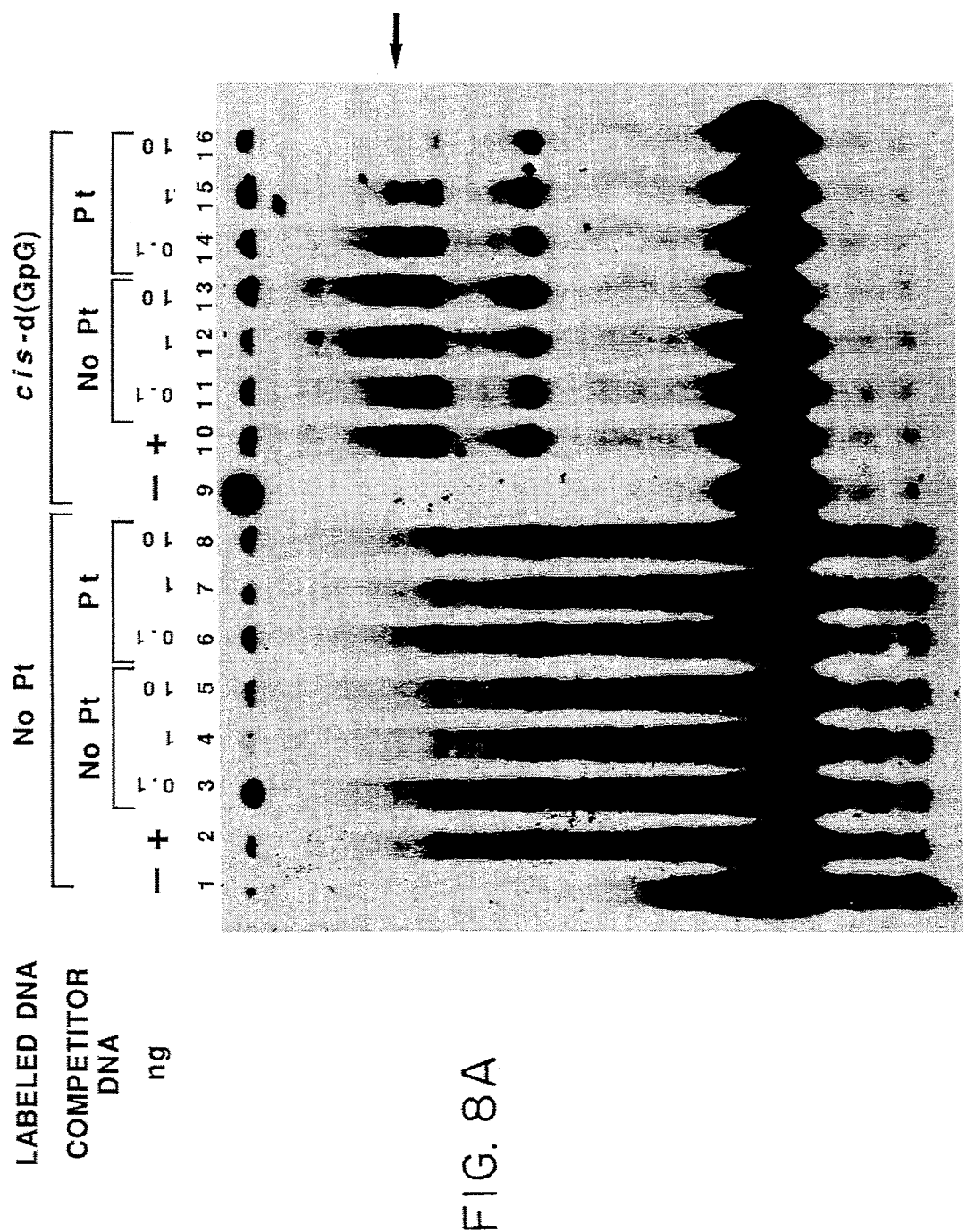
FIGS. 8A–C present the results of an EMSA study showing the selectivity of the cellular cis-DDP SSRP for binding to the d(GpG) and d(ApG) 1,2-intrastrand dinucleotide adducts formed by cisplatin. In this study, the oligonucleotides shown in FIG. 7 (containing defined structural motifs produced by the interaction of platinum compounds with DNA) were used.

FIG. 8A shows the results of an analysis of SSRP specific recognition of the d(GpG) structural motif, wherein DNA fragments, 110 bp in length, were prepared as described above from 22 bp oligonucleotides that were either unmodified (see lanes 1-8 of FIG. 8A) or modified to contain the cis-DDP d(GpG) adduct (lanes 9-16). These oligonucleotides were incubated in the absence (−; lanes 1 and 9) or the presence (lanes 2-8 and 10-16) of 20 μg of HeLa cytosolic extract prepared as described in Example A. Unmodified, unlabelled M13mp18 DNA was used as a nonspecific competitor at 0.1, 1, and 10 ng per binding reaction ("No Pt"; lanes 3, 4, 5, 11, 12, and 13 of FIG. 8A). Unlabelled M13mp18 DNA modified with cis-DDP at an $r_b$ level of 0.041 was used as a specific competitor at 0.1, 1 and 10 ng per reaction ("Pt"; lanes 6, 7, 8, 14, 15 and 16). SSRP binding in the absence of competitor DNA is also shown (+; lanes 2 and 10).

Figure 8B:
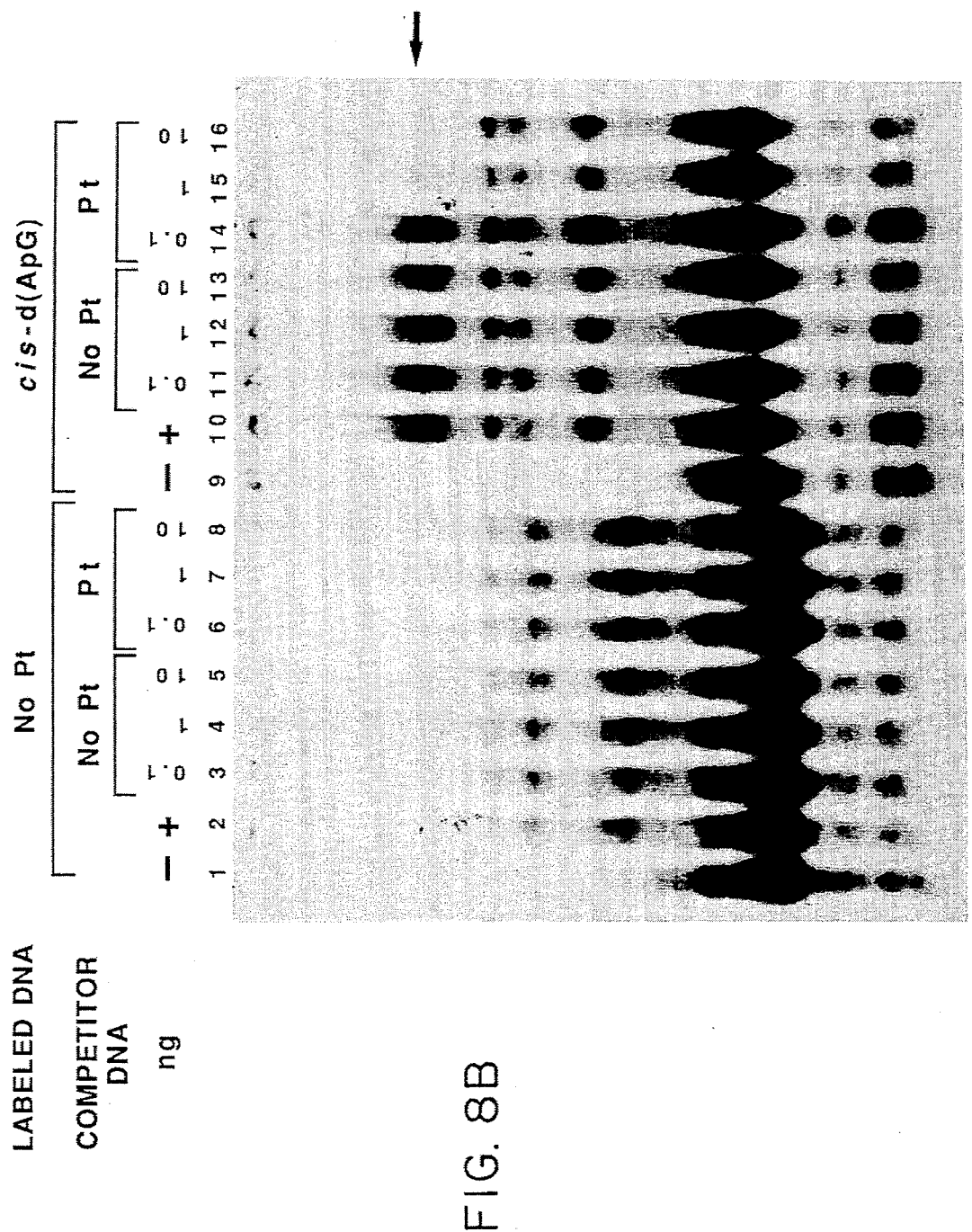

FIG. 8B shows the results of an analysis of SSRP specific recognition of the d(ApG) structural motif. This study was designed in a similar manner to that shown in FIG. 8A (i.e., lane designations are analogous).

Figure 8C:
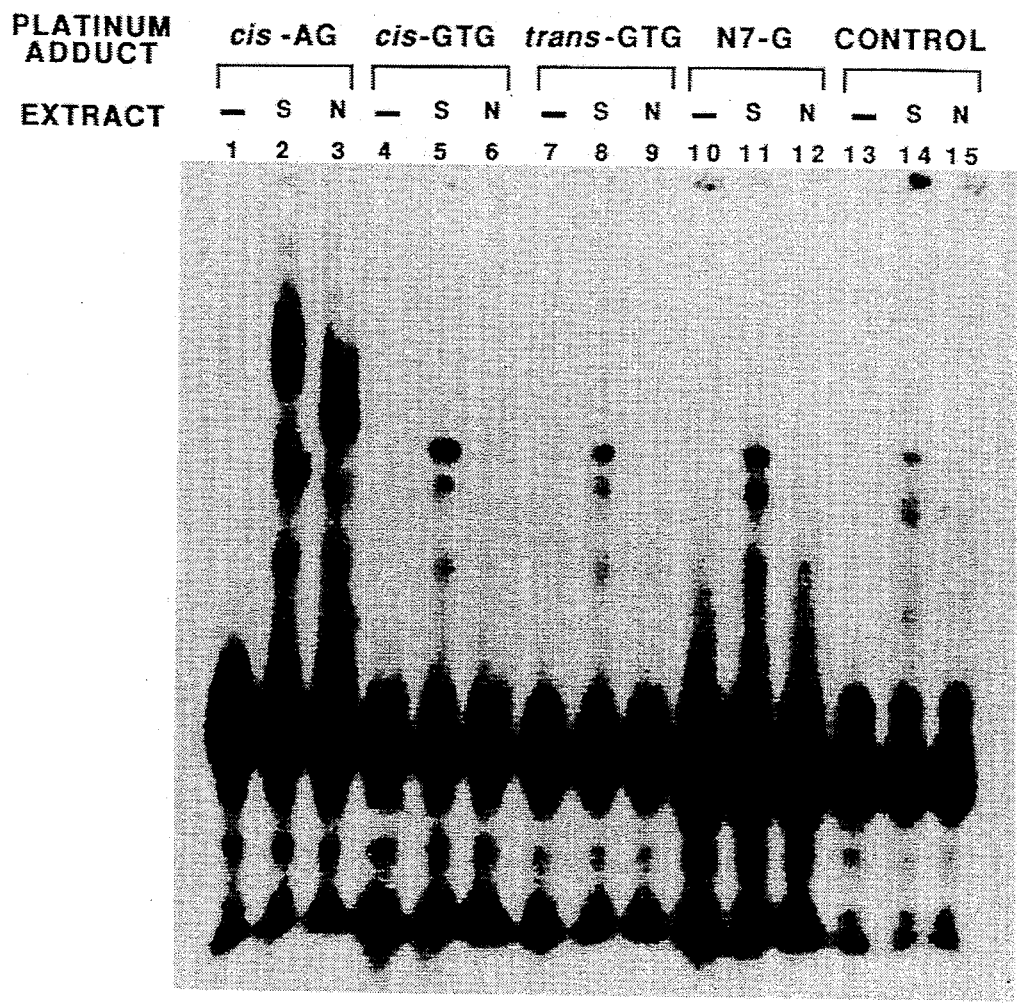

FIG. 8C shows the results of an EMSA study investigating the ability of SSRP to recognize other Pt-DNA structural motifs. It shows that SSRP does not bind to the d(GpTpG) 1,3-intrastrand crosslinks formed by cis- or trans-DDP, or a monofunctional DNA adduct formed by [Pt(NH$_3$)$_2$(N3-cytosine)]$_{2+}$. DNA fragments 110 bp long were constructed as described above. These fragments contained platinated structural motifs as follows: lanes 4-6, the d(GpTpG) cis 1,3-diadduct; lanes 7-9, the d(GpTpG) trans 1,3-diadduct; lanes 10-12, the N7-dG monofunctional adduct of [Pt(NH$_3$)$_2$(N3-cytosine)]$_{2+}$. Each type of predefined, damaged DNA fragment was incubated in the absence (−; lanes 4, 7 and 10), or the presence of 20 μg HeLa cytosolic extract (S; lanes 5, 8 and 11) or 10 μg HeLa nuclear extract (N; lanes 6, 9 and 12). FIG. 8C also shows nonspecific binding to an unmodified 110 bp fragment (llanes 13-15), and specific binding to the cis 1,2-d(ApG) adduct (lanes 1-3).

It can be seen that there is substantial nonspecific binding to these oligonucleotides, as evidenced by the presence of slower migrating bands seen in the cases where the oligonucleotides were not modified with platinum (e.g., FIG. 8A, B, lanes 2-8). Specific binding was observed, however, to DNA fragments containing the 1,2-intrastand d(GpG) and d(ApG) cross-linked adducts of cis-DDP (FIG. 8A, B, lane 10). SSRP bound to oligonucleotides 88 or 110 bp in length, but not to those that were 44 or 66 bp long. This probe size limitation presumably reflects a minimum requirement for a flanking nucleic acid domain in order for protein binding to occur. Binding was not observed with randomly modified DNA fragments at $r_b$ values of less than 0.007, suggesting that a minimum level of modification is required for binding of the DRP in crude extracts. The band representing specific binding to platinated oligonucleotides of 110 bp could be competed away with an about 340-fold excess of unlabeled M13mp18 RF DNA modified with cis-DDP at a bound drug to nucleotide level of 0.041 (FIGS. 8A and B, lane 16) but not with unlabeled unplatinated M13mp18 DNA (lane 13) at the same approximately 340-fold excess. No specific binding occurred in cases where the DNA probes contained the d(GpTpG) 1,3-intrastrand cross-linked adducts of cis-DDP and trans-DDP or the monofunctional d(G)-N7 adduct of {Pt(NH$_3$)$_2$(N3-cytosine)}Cl (FIG. 8C).

Thus, the results of this study further support the postulate that SSRP recognizes a structural motif comprising a 1,2-intrastrand dinucleotide adduct.

EXAMPLE I

EMSA Studies Revealed that the Cellular cis-DDP SSRP does not simply respond to ss DNA As noted previously in the Detailed Description, the 1,2-intrastrand d(GpG) and d(ApG) DNA adducts of cis-DDP bend the helix in the direction of the major groove, and are thought to produce a local region of ss DNA opposite to the site of the platinum lesion. In fact, such ass motif could be detected by antinucleoside antibodies (reported by Sundquist et al., *Biochemistry* 25;1520–1524 (1986)). This observation suggested that SSRP might recognize a single-stranded domain, rather than a structural motif (e.g., a helix kink) produced by the platinated DNA adduct itself.

This possibility was excluded by a competitive EMSA study in which nuclear extracts from HeLa cells were incubated in the presence of 5000 cpm (0.2 ng) of the 274 bp ds restriction fragment described in Example A, modified with cis-DDP at 0,040 Pt/nucleotide. Single stranded DNA was prepared by boiling the unplatinated, radiolabeled 422 bp restriction fragment disclosed in Example A, and then allowing the DNA to reanneal in the presence of a 10-fold molar excess of M13mp18 circular ss DNA (+) strand. The 422 nucleotide (+) strand was then resolved on, and isolated from, a native polyacrylamide gel and platinated as described for the double stranded DNA fragments. Escalating concentrations (0.2–100 ng) of this unlabeled ss M12mp18 DNA was added to EMSA samples as a competitor. Single-stranded DNA was not observed to compete with the cis-DDP modified ds DNA fragment for binding to SSRP, a result which bolsters the suggestion that SSRP does not simply respond to ss domains.

EXAMPLE J

EMSA Studies Also Showed that the Cellular cis-DDP SSRP does not bind to UV-induced DNA lesions A factor has been reported in nuclear extracts prepared from HeLa cells that binds specifically to DNA damage induced by UV irradiation. Chu, G. and E. Chang, *Science* 242:564–567 (1988). Accordingly, UV-damaged DNA fragments were prepared and employed in a competitive EMSA study to determine whether the factor reported by Chu and Chang is related to SSRP (see also Example F). The 422-bp DNA fragment derived from AvaI digestion of M13mp18 (Example A) was purified by electrophoresis through a low-melting agarose gel followed by butanol extraction in the presence of CTAB. DNA fragments were labeled with [$\alpha$-$^{32}$P]dCTP and purified as described above. The labeled DNA fragments were then irradiated with a General Electric 15-W germicidal lamp (maximum output at 254 nm) calibrated with a UVX digital radiometer at a flux of 5 J/(m$^2$-s) and a final dose of 1500 J/m$^2$.

Competition reactions included the end-labeled, Pt-modified ($r_b$ of 0.038) 422 bp fragment, 10 µg of HeLa nuclear extract, and escalating levels (0.1–10 ng) of unlabelled competitor M13mp18 DNA modified with either cis-DDP at an $r_b$ of 0.041, or with UV light as described in the preceeding paragraph. In a second series of competition reactions, end-labelled, UV-modified 422 bp fragment was used.

The results of this study revealed that SSRP binding was not competed by a 1000-fold excess of M13mp18RF DNA treated with UV at 1500 J/m$^2$, which corresponds to a calculated level (Spivak et al., *Mutat. Res.* 193:97–108 (1988)) of about 5.7 cyclobutane dimers per kilobase. Conversely, the binding of a factor found only in nuclear extracts to labelled DNA modified with UV light at 1500 J/m$^2$ could be competed with a 1000-fold excess of unlabeled, UV-irradiated M13mp18 DNA, but not with a 1000-fold excess of DNA platinated with cis-DDP. These results bolster the conclusion that cis-DDP SSRP is not the factor described by Chu and Chang as capable of recognizing UV-induced DNA lesions.

EXAMPLE K

Partial Purification and Characterization of the Cellular cis-DDP SSRP

Purification of Cellular cis-DDP SSRP

Saturated ammonium sulfate was added dropwise to HeLa crude cytosolic extracts to a final concentration of 40%. The mixture was stirred on ice for 30 minutes and centrifuged at 11,000 rpm in a Sorvall SM24 rotor for 30 minutes. Proteins present in the supernatant were precipitated with ammonium sulfate added as above to a final concentration of 65%. The 40–65% fraction (i.e., the second precipitate) was resuspended in buffer H (25 mM HEPES, pH 7.5, 150 mM KCl, 0.1 mM Na$_2$EDTA, 1 mM DTT, and 10% glycerol) and dialyzed extensively against the same buffer.

Sucrose Gradient Ultracentrifugation

Essentially, the method of Johns, P. and D. R. Stanworth, *J. Immunol. Methods* 10:231–252 (1976) was followed. A portion of the 40–65% fraction representing 1 mg of protein was centrifuged through a 0–15% linear sucrose gradient for 18 hours at 43,600 rpm ($\omega t^2 = 1.34 \times 10^{12}$, 170 000 g) in a Beckman SW 50.1 rotor. Fractions were removed from the top of the gradient and dialyzed extensively against buffer H. Each fraction was subsequently assayed for cis-DDP-DNA binding activity by EMSA, in the manner described in Example A (i.e., using the end-labelled, cis-DDP modified 422 bp AvaI restriction fragment of M13mp18). Protein standards were centrifuged in parallel as molecular weight markers. Fractions from this gradient were precipitated with methanol/chloroform (3:1 and resuspended in SDS loading dye (0.3M Tris base, pH 9.0, 50% glycerol, 5% SDS, 5% 2-mercaptoethanol, 0.0025% brophenol blue). The fractions were then electrophoresed through a 12% SDS-polyacrylamide gel, and the gel was stained with Coomassie blue R-250 to detect protein.

Figure 9:
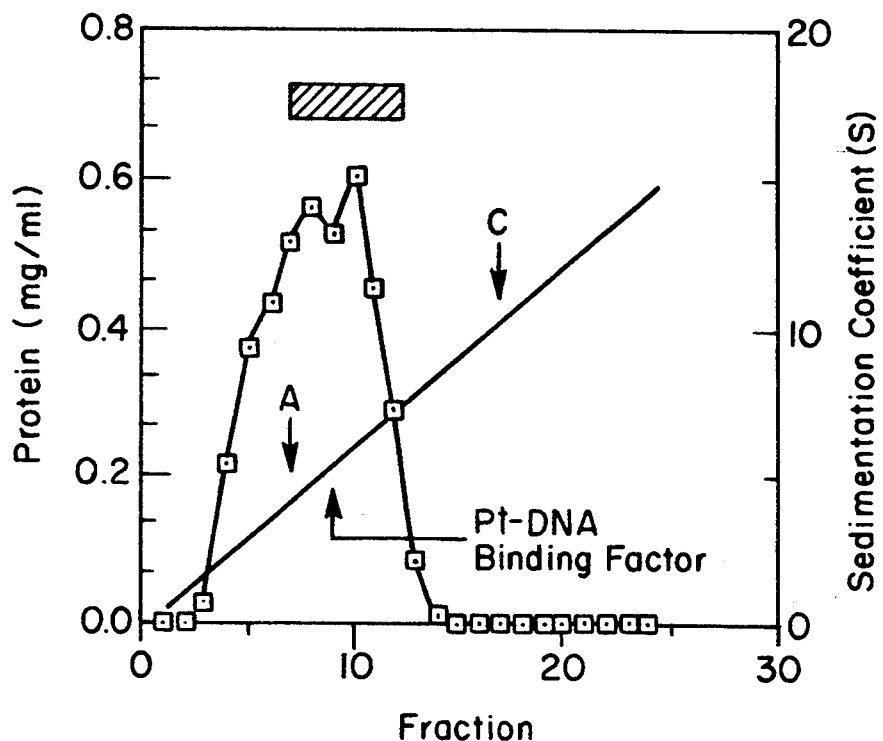
FIG. 9 is a graphic illustration of the sedimentation of the cellular SSRP through a sucrose density gradient. □, protein concentration (mg/mL); A, C, and —, sedimentation coefficient size markers (A, albumin ($M_r$ of 67 000 daltons); C, catalase ($M_r$ of 232 000 daltons)). The hatched box indicates the sedimentation region corresponding to cis-DDP-DNA binding activity (as determined by EMSA study of the fractions).

FIG. 9 presents the results of this study to determine the size of the cellular cis-DDP SSRP by sucrose gradient sedimentation. The profile of the gradient is shown; EMSA study of the fractions revealed that SSRP was located in fractions 7–12, with the peak of activity in fraction 9. From these data, the sedimentation coefficient of SSRP was calculated to be 5.6 S, which corresponds to an apparent molecular weight of 91 000 daltons for a globular protein. It will be seen from the Examples which follow that this result is in agreement with assessments of the molecular weight of SSRP based upon modified Western blot analysis.

EXAMPLE L

Modified Western (Southwestern) Blotting Technique for Detecting the Presence of SSRP Preparation of Crude Extracts Eukaryotic nuclear and cytosolic extracts of HeLa cells were prepared as described in Example A. *Escherichia coli* strain SG1161 (lon) lysogens were prepared as described in the literature. Singh, H. et al., *Cell*, 52:415–423 (1988). This strain of *E. coli* was chosen to reduce proteolytic degradation of the expressed fusion protein (comprising β-galactosidase and at least a portion of SSRP).

Radiolabelled and platinum-modified DNA fragments used for modified Western Blotting studies were prepared as described in Example A.

Southwestern Blot Procedure

Extracts were prepared from either IPTG-induced (IPTG refers to isopropyl-β-D-thiogalactopyranoside) lysogens or HeLa cells. Typically, 50 μg total protein per lane were separated by sodium doedecyl sulfate-polyacrylamide gel electrophoresis (SDS-PAGE) on an 8% separating gel and transferred onto nitrocellulose (Schleicher & Schuell, BA85, 0.45 μm) according to conventional techniques. Following transfer, filters were processed as described in the literature. Laemmli, U.K., *Nature*, 227:680–685 (1970); H. Towbin et al., *Proc. Natl. Acad. Sci., USA*, 76:4350–4354 (1979); H. Singh et al., *Cell*, 52:415–423 (1988). To assay for DNA binding, nitrocellulose filter-bound proteins were incubated in binding buffer (30 mM HEPES [N-2-hydroxyethyl-piperazine-N-2-ethane-sulfonic acid NaOH] pH 7.5, 10 mM $MgCl_2$, 2 mM $MnCl_2$, 0.25% nonfat dry milk), using 20 mL per 20×20 cm filter, with $^{32}$P-labeled DNA fragment (0.25–2.0×$10^4$ cpm/mL, $10^{-10}$ to $10^{-11}$M). Poly(dI-dC)•poly(dI-dC) was added as competitor for non-specific DNA binding proteins at 10 μg/mL or 4×$10^{-5}$M. The incubations were run for 60 minutes at room temperature with gentle agitation. In an experiment using single stranded DNA as a probe, a mixture of 5 μg/mL each of poly(dI-dC)•poly(dI-dC) and M13mp18 single stranded (+ strand) DNA was used as competitor. Unbound DNA was then removed by washing the filters twice at 4° C. with binding buffer lacking $MgCl_2$ and $MnCl_2$. Thereafter, (damaged DNA fragment):(protein) complexes present on the blot surface were detected by autoradiography with the use of an intensifying screen at −80° C.

This procedure was used successfully to visualize HeLa cellular SSRP and recombinant fusion proteins having SSRP activity. The cellular protein was observed to have electrophoretic migration properties consistent with a globular protein of about 100 000 daltons. These studies are more fully described below.

EXAMPLE M

Southwestern Blot Screening Procedures for Detection of Recombinant Expression Products having SSRP Activity FIG. 10 shows representative protein replica filters prepared from an unamplified human B cell (RPMI 4265) cDNA library (Clontech Laboratories, Inc.) constructed in the expression vector λgt11. The cDNA library was originally prepared by oligo(dT) priming of poly(A)+ RNA, S. J. Chan et al., *Proc. Natl. Acad. Sci., USA*, 76:5036–5040 (1979). The library contains approximately 9×$10^5$ independent clones with insert sizes in the range of 0.73 to 4.1 kb and a titer of 3.6×$10^9$ plaque forming units (PFU)/mL. Screening of the μgt11 recombinants plated on *E. coli* host strain Y1090 was carried out as described in H. Singh, et al., *Cell*, 52:415–423 (1988), using cisplatin-modified, $^{32}$P-labeled DNA to screen clones for platinated DNA binding. Each filter was incubated for 60 minutes at room temperature in 10 or 25 mL TNE (10 mM Tris-HCl pH 7.5, 50 mM NaCl, 1 mM $Na_2$EDTA, 1 mM DTT) for 100 and 150 mm plates, respectively. The buffer contained $^{32}$P-labeled platinated DNA at a final concentration of approximately 3×$10^4$ cpm/mL (approximately $10^{-11}$M) as well as both sonicated native and denatured calf thymus DNA with an average length of approximately 1 kb at 1.0 and 5.0 μg/mL, respectively. The filters were then washed at room temperature three times for ten minutes per wash using TNE, air dried, and autoradiographed at −80° C. with the use of an intensifying screen for 24–48 hours. Putatively positive clones were rescreened for binding to cis-DDP-modified DNA. Secondary screens were carried out on 100 mm plates with plating mixtures of approximately 5×$10^3$ PFU of phage, while tertiary screens used plating mixtures of about 100 PFU. This protocol was employed successfully to purify two recombinant phage, λPt1 and λPt2 (Seq. ID Nos. 8 and 9), to homogeneity.

EXAMPLE N

Southwestern Blot Study of Cellular and Recombinant Proteins having SSRP Activity In order to demonstrate that the clones isolated in Example M encode proteins which specifically bind to DNA modified by cis-DDP, *E. coli* lysogens were prepared for each clone, as well as for the cloning vector lacking the insert. As a control, HeLa extract was also prepared and included in the analysis. The results of this study are presented in FIG. 11.

Crude extracts obtained from induced lysogens were subjected to SDS-PAGE and the resolved proteins were transferred to nitrocellulose filters. Four filters were prepared, comprising the following samples: lane 1, HeLa cytosolic extract; lane 2, bacterial lysogen crude extract from the λgt11 vector (lacking insert); lane 3, bacterial lysogen crude extract from λPt2 (Seq. ID No. 9); and lane 4, bacterial lysogen crude extract from λPt1 (Seq. ID No. 8). Following denaturation and renaturation according to the method of Celenza, J. L. and M. Carlson, *Science*, 233:1175–1180 (1986), the four filters were probed and developed as follows (referring to the panels of FIG. 11): A, India Ink stain to visualize total proteins; B, a monoclonal antibody raised against β-galactosidase, followed by immunoglobulin-specific detection according to the Western Blotting method of F. M. Ausubel et al., *Current Protocols in Molecular Biology*, Green Publishing Associates and Wiley Interscience, New York, Section 10.7.1.; C, $^{32}$P-labeled, unmodified 422 bp AvaI restriction fragment of M13mp18 (Example A); and D, the same DNA fragment modified with cis-DDP.

Thus, panels C and D depict the results of Southwestern blotting studies. These investigations showed the presence of two predominant polypeptides having β-galactosidase immunoreactivity, which selectively bind to DNA fragments modified by cis-DDP, separated by approximately 4 kDa, in λPt1 (Seq. ID No. 8) lysogens. The slower migrating band corresponds to a molecular weight of approximately 172 kDa. The faster migrating band can be attributed to proteolysis of the phage encoded protein.

In subsequent studies, filter-bound, electrophoretically resolved proteins were also probed with DNA fragments modified with [Pt(en)Cl$_2$], trans-DDP, or [Pt(dien)Cl ]$^+$. These studies revealed that bacterial induced lysogens from λPt2 (Seq. ID No. 9) and λPt1 (Seq. ID No. 8) bound only to DNA modified by cis-DDP or [Pt(en)Cl$_2$], in accord with results obtained with the HeLa cellular SSRP. The detection limit of this modified Western (Southwestern) Blot technique for binding of the phage-encoded proteins to cis-DDP-modified DNA was found to be approximately 2 platinum adducts per 100 nucleotides, corresponding to an $r_b$ level of 0.02.

EXAMPLE O

Restriction Enzyme Mapping of the Isolated cDNA Clones, λPt1 and λPt2

Amplified phage stocks prepared from λPt1 and λPt2 (Seq. ID Nos. 8 and 9) were used to isolate recombinant DNA. T. Maniatis et al., *Molecular Cloning: A Laboratory Manual*, Cold Spring Harbor Laboratory, Cold Spring Harbor, N.Y., pp. 76–85 (1982). Each clone was digested with a variety of restriction enzymes (obtained from International Biotechnologies and Bethesda Research Laboratories). After electrophoretic separation, DNA fragments were transferred to a nitrocellulose filter. *Id.*, pp. 383–386. To determine any homologies between the two cDNA clones, the filter was probed with λPt2 (Seq. ID No. 9) cDNA insert labelled with [α-$^{32}$P] deoxy-cytidine triphosphate by the Klenow fragment of DNA polymerase I. *Id.*, pp. 113, 178. Hybridization was carried out with 10% dextran sulfate in 50% formamide for 3 hours at 45° C., and the filters were washed twice with 1×SSC/0.1% SDS (wherein SSC is 0.15 M NaCl, 15 mM trisodium citrate pH 7.0, and SDS is sodium doedecyl sulfate) at room temperature followed by two additional washes with 0.1×SSC/0.1% SDS at room temperature. Autoradiography was carried out at −80° C. with use of an intensifying screen.

Figure 12:
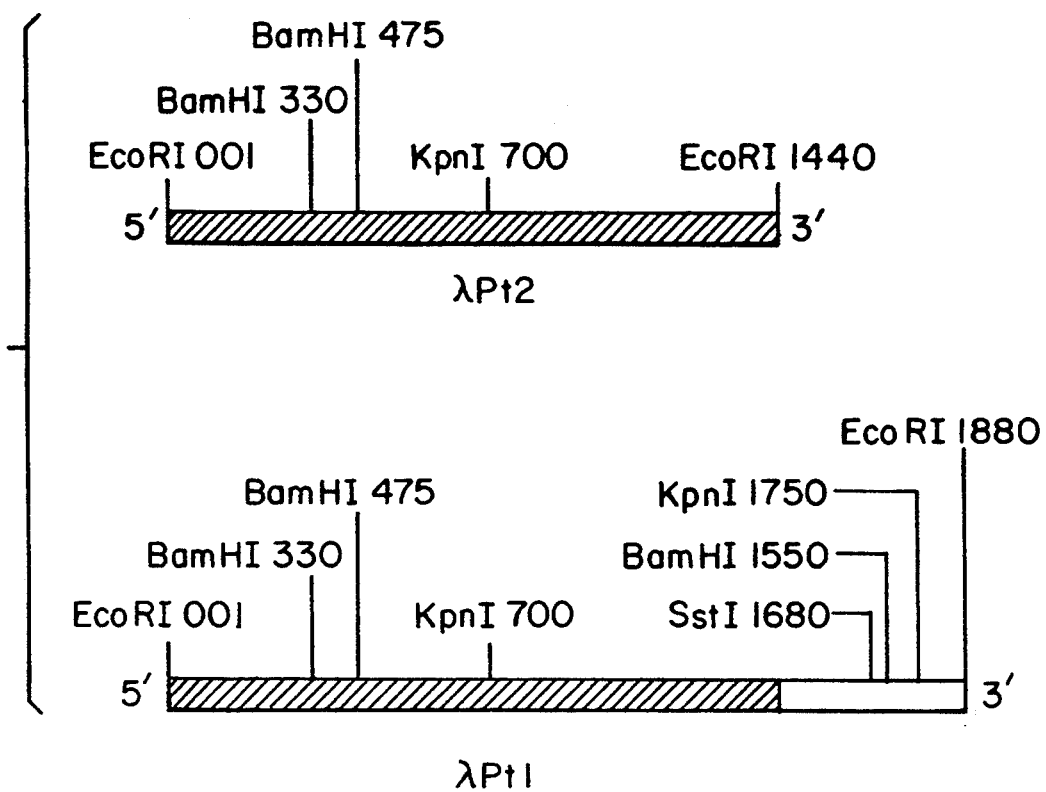
FIG. 12 is a schematic representation of the restriction endonuclease maps of phages λPt1 (Seq. ID No. 8) and λPt2 (Seq. ID No. 9) showing the 5' alignment of their cDNA inserts.

The results of these studies are summarized in FIG. 12. Enzyme mapping analysis of the two recombinant phage λPt1 (Seq. ID No. 8) and λPt2 (Seq. ID No. 9) indicated that they contain nucleotide sequences aligned at their 5' ends, with insert sizes of 1.44 and 1.88 kb, respectively. Southern blotting analysis confirmed homology between the two clones. The apparent molecular weight of the portion of the fusion protein encoded by λPt2 (Seq. ID No. 9) which represents the cloned human B cell polypeptide is estimated to be approximately 50 kDa. This polypeptide represents at least a portion of a cellular protein having cis-DDP SSRP activity.

EXAMPLE P

Expression Studies of the Cellular Protein encoded by the λPt1 and λPt2 Sequences Northern Blotting Technique Cytoplasmic RNA from human HeLa, hamster V79, and murine leukemia L1210 cells were isolated by using a published procedure. G. Sonenshein et al., *J. Exp. Med.*, 148:301–312 (1978). Twelve micrograms of RNA were loaded in each lane and resolved on a 1% agarose gel containing 6% formaldehyde, 20 mM 3-[N-morpholino] propanesulfonic acid, 5 mM sodium acetate and 1 mM Na$_2$EDTA. RNA was transferred in 20×SSC by capillary action to Gene Screen Plus TM brand blotting paper (New England Nuclear). The λPt2 (Seq. ID No. 9) DNA insert was labeled with [α-$^{32}$P] deoxycytidine triphosphate according to a known technique. Feinberg, A. P. and B. Vogelstein, *Anal. Biochem.*, 132:6–13 (1983). The filter was probed with 10$^6$ cpm/mL of this probe in hybridization mixture (45% formamide, 10% dextran sulfate, 0.1% sodium phosphate, 50 mM Tris-HCl pH 7.5, 5× Denhardt's solution, 100 μg/mL sheared, denatured salmon sperm DNA and 0.5% sodium doedecyl sulfate) at 42° C. Thereafter, filters were washed twice using 2×SSC at 65° C. followed by two additional washings with 1×SSC/0.1% SDS at 65° C. Autoradiography was carried out at −80° C. with use of an intensifying screen.

Preliminary Northern analysis of the expression of the λPt2 (Seq. ID No. 9) gene demonstrated the presence of a conserved cytoplasmic RNA species of 2.8 kb in HeLa, murine leukemia L1210 and Chinese hamster V79 cells. The predicted molecular weight of the full length cellular protein encoded by this mRNA is 100 000 daltons. It will be noted that this mass is similar to that of the binding factor identified as SSRP, as observed by Southwestern blot analysis of HeLa cytosolic extracts. This correlation supports the inference that the clone λPt2 (Seq. ID No. 9) encodes a portion of this same factor.

In a subsequent study, the following Northern blotting technique was employed to further characterize expression patterns of the SSRP gene:

Northern Analysis

RNA was isolated by using standard procedures (J. Sambrook et al.) *Molecular Cloning: A Laboratory Manual* (1989). Typically, 12 μg of RNA were used for electrophoretic analysis in 1% agarose gels containing 6% formaldehyde, 20 mM MOPS, 5 mM NaOAc, and 1 mM EDTA. Gels were denatured for 15 minutes in 50 mM NaOH, 100 mM NaCl, neutralized in 100 mM Tris (pH 7.5), and transferred to GeneScreenPlus TM (New England Nuclear) by capillary action in 10X SSC. Filters were rinsed in 2X SSC and baked in a vacuum oven for two hours at 80° C. Pre-hybridization for four hours and hybridization for 16 hours with 1×10$^6$ cpm of labelled λPt2 (Seq. ID No. 9) DNA per ml of hybridization fluid was carried out at 42° C. in 30–40% formamide, 10% dextran sulfate, 0.1% NaPP$_i$, 50 mM Tris (pH 7.5), 5X Denhardt's, 0.5% SDS, and 100 μg/ml denatured salmon sperm DNA. Filters were washed at 55° C. with 2X SSC, 0.1% SDS twice, and in 1X SSC, 0.1% SDS twice for 30 minutes each and exposed to X-ray film.

In order to determine the tissue specificity of SSRP gene expression, total RNA was isolated from baboon brain, heart, ileum, jejunum, kidney, liver, muscle, and spleen tissue and subjected to Northern analysis. The results of this survey revealed that the 2.8 kb SSRP message is expressed in all tissues examined. Rehybridization probing of the filter with a fragment of human β-actin allowed normalization for RNA loading levels, and showed that the relative levels of SSRP expression were similar each of the tissues analyzed, except for brain tissue, in which it is higher.

Because of the exceptional success of cisplatin in treating testicular cancer, a more detailed analysis of expression was carried out in a series of testicular carcinoma cell lines. Several bladder cancer cell lines (Masters, J. R. W. *Cancer Res.* 46:3630–3636 (1986)) were studied concurrently because cisplatin is less active against this type of cancer. SSRP is expressed in all of the bladder and testicular cell lines examined; no general trends were apparent. These data indicate that the intracellular level of SSRP mRNA does not correlate with the antitumor activity of cisplatin for a particular tissue type.

Since the protein described herein specifically recognizes DNA adducts of active antitumor platinum complexes, its possible role in acquired resistance of cells to cisplatin was also investigated. A Northern blot analysis in which the λPt2 (Seq. ID No. 9) clone was used to probe cytoplasmic RNA levels in a series of cisplatin resistant human, mouse, and hamster cell lines was carried out. Data obtained from this study indicate that the level of SSRP expression does not correlate with resistance in these cell lines.

In order to study whether expression of the cisplatin-DNA SSRP could be induced in cells treated with the drug, cytoplasmic RNA was isolated from HeLa cells which had been exposed to a range of concentrations of cisplatin. The 2.8 kb mRNA SSRP gene transcript was not inducible by a wide range of cisplatin concentrations over the course of 48 hours.

EXAMPLE Q

Use of Clones λPt1 and λPt2 to Obtain the Full Length human cDNA Sequence Encoding SSRP Labelling of Probes for Hybridization The λPt2 (Seq. ID No. 9) clone (reported in J. H. Toney et al. *Proc. Natl. Acad. Sci., USA* 86:8328–8332 (1989)) was used as a probe for hybridization and library screening. λPt2 (Seq. ID No. 9) was radiolabelled by random oligonucleotide priming as described in Feinberg, A. P. and Vogelstein, B. *Anal. Biochem* 132:6–13 (1983). Typically, 50–100 ng of DNA in low melting point agarose was boiled, primed with pd(N)$_6$ oligonucleotides (Pharmacia), and labelled with α-[$^{32}$P]dCTP by *Escherichia coli* DNA polymerase I (Klenow fragment). Labelled fragments were purified by spin dialysis over Sephadex G-50 columns and the extent of incorporation of radioactivity was monitored by scintillation counting.

Library Screening

For the primary screen of each cDNA library, $5 \times 10^6$ recombinant phage were plated on *E. coli* host strain Y1088. Duplicate replica nitrocellulose filters were prepared and then denatured (0.5M NaOH, 1.5M NaCl), neutralized (1M Tris (pH 7.4), 1.5M NaCl), and rinsed with 2X SSC (20X SSC:3M NaCl, 0.3M Na$_3$C$_6$H$_5$O$_7$). After baking for two hours at 80° C. in a vacuum oven the filters were pre-incubated at 42° C. for four hours with hybridization fluid (50% formamide, 1M NaCl, 50 mM Tris (pH 7.5), 0.5% SDS, 10% dextran sulfate, 1X Denhardt's solution, and 1 mg/ml denatured salmon sperm DNA). Probe was then added at a concentration of $1 \times 10^6$ cpm of labeled DNA per ml of hybridization fluid and the incubation was continued for an additional 16 hours. The filters were washed once at room temperature in 2X SSC/0.1% SDS, twice at 65° C. in 2X SSC/0.1% SDS, and twice at 65° C. in 0.1X SSC/0.1% SDS for fifteen minutes each. The filters were air dried briefly and analyzed by autoradiography. Multiple rounds of screening were used to isolate plaque pure bacteriophage clones. Single plaques were amplified in liquid culture for DNA preparation and further analysis.

In this manner, overlapping cDNA clones spanning the entire coding sequence of the human SSRP gene (Seq. ID No. 6) were identified and isolated from human embryonic kidney (HEK) fetal muscle (M), and basal ganglia (BG) cDNA libraries. These clones were subjected to Southern blot and sequencing analyses as described below.

EXAMPLE R

Southern Blotting Studies of Overlapping cDNAs Encoding Human SSRP

Southern Analysis

High molecular weight genomic DNA was prepared by slowly dripping cells into lysis buffer (10 mM Tris (pH 8.0), 100 mM NaCl, 1 mM EDTA, 1% SDS), followed by overnight digestion with proteinase K (100 μg/ml), multiple phenol and chloroform extractions, and resuspension in TE (50 mM Tris (pH 7.5), 10 mM EDTA). For each sample, 10 μg of DNA was digested to completion and the fragments separated by electrophoresis in 0.8% agarose gels. Gels were denatured for 45 minutes (0.5M NaOH, 1.5M NaCl), neutralized for 60 minutes (1M Tris (pH 7.4), 1.5M NaCl) and the DNA immobilized on Zetabind ™ membrane (Cuno) by capillary transfer for 16 hours in 10X SSC. After rinsing the filter with 2X SSC, it was baked in a vacuum oven at 80° C. for two hours. Following pretreatment at 65° C. for one hour (0.5X SSC, 0.5% SDS) the filters were hybridized and washed as described above for library screening, and then analyzed by autoradiography.

Figure 13:
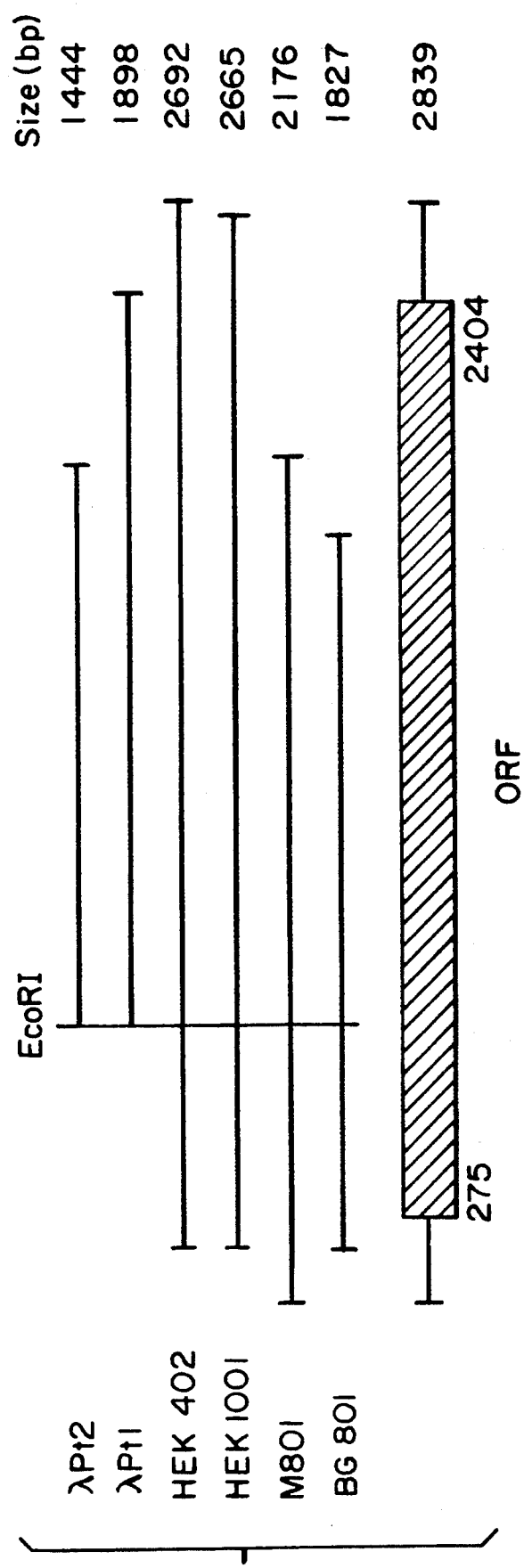
FIG. 13 is a schematic illustration showing the relationship among human cDNA clones encoding SSRP (Seq. ID No. 6).
Figure 14:
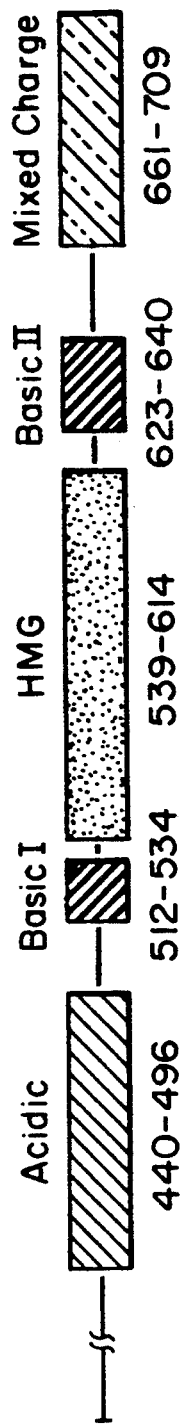
FIG. 14 is a schematic illustration, prepared from the predicted amino acid sequence of the human SSRP gene illustrated in FIG. 13, showing various domains of the human structure-specific recognition protein (Seq. ID No. 7). HMG or HMG-box; domain having a high degree of sequence homology to high mobility group 1 protein.

A schematic representation showing the relationship between human cDNA clones encoding SSRP (Seq.ID No. 6) is presented in FIG. 13. Clones λPt1 (Seq.ID No. 8) and λPt2 (Seq.ID No. 9) were isolated from a human B cell library as discussed previously. Clone HEK 402 was isolated from a human embryonic kidney library, and contains the complete SSRP cDNA sequence and polyadenylation signal. Clone M 801 was isolated from a fetal muscle library, and lacks the 3' end of the gene but contains 147 bases of additional 5' untranslated sequence. Clone BG 801 was isolated from a basal ganglia cDNA library and also lacks the 3' end of the gene, but served to confirm the sequence of its 5' end. All cDNA clones were completely sequenced in both directions as described in the following Example, and were found to be identical in overlapping regions.

EXAMPLE S

Sequencing of Human cDNAs Encoding SSRP and Characterization Thereof

Subcloning

Purified phage DNA was digested with EcoRI to release the cDNA inserts. The EcoRI fragments were isolated from low melting point agarose gels using GENECLEAN ™ (Bio 101) and ligated into the EcoRI site of plasmid pBluescript SKII+. After transformation of competent *E. coli* XL-1 cells, single colonies were isolated and amplified in liquid culture. DNA was purified by using Qiagen affinity chromatography.

Sequence Determination and Analysis

Sequence determination was performed on double-stranded plasmid DNA by using the chain termination method (F. Sanger et al. *Proc. Natl. Acad. Sci., USA* 74:5463–5467 (1977)) and Sequenase T7 DNA polymerase (United States Biochemical). Sequence analysis employed software from Genetics Computer Group (GCG) at the University of Wisconsin (J. Devereaux et al. *Nucl. Acids. Res.* 12:387-395 (1984)). Homology searches were made by using the BLAST Network Service at the National Center for Biotechnology Information (S. F. Altschul et al. *J. Mol. Biol.* 215:403-410 (1990)).

By using the sequence information from these clones, a composite human sequence representing 2839 bases of DNA was generated (Seq. ID No. 6). There is a continuous open reading frame of 2130 bases beginning at position 275. The sequence surrounding the methionine start codon conforms well with the initiation sites of other vertebrate cDNAs (Kozak, M. *Nucl. Acids. Res.* 15:8125-8132 (1987)) and is conserved in homologs isolated from mouse (M. Shirakata et al., *Molecular and Cellular Biology* 11:4528-4536 (1991)) and *Drosophila melanogaster* (Bruhn, S., et al., *Prog. Inorg. Chem.* 38:477-516 (1990)). A consensus polyadenylation signal AATAAA is present within the 435 bases of 3' untranslated sequence beginning at position 2800.

The sequence predicts a 710 amino acid protein of molecular weight 81,068 Daltons (Seq. ID No. 7). The amino acid composition reveals a strikingly high percentage of charged residues (36%). Further analysis of the protein sequence indicated the presence of several highly charged domains, illustrated in FIG. 14. There is an acidic domain, aa 440-496, which contains 26 negatively charged and 4 positively charged amino acids. Two basic domains, denoted Basic I and Basic II, are located at aa 512-534 and aa 623-640, respectively. At the carboxyl terminus of the protein, aa 661-709, there is another highly charged series of amino acids containing 14 negative and 9 positive residues. Analysis of the hydropathy profile shows the entire region from aa 400 to the carboxyl terminus of the protein to be highly hydrophilic (not shown).

A search of protein data bases with the predicted amino acid sequence (Seq. ID No. 7) revealed some interesting homologies. SSRP showed the greatest homology to high mobility group (HMG) 1 and 2 proteins from several species, (Eink, L. and Bustin, M. *Exp. Cell Res.* 156:295-310 (1985); M. Bustin et al., *Biochim. Biophys. Acta* 1049:231-243 (1990)) and to a transcription factor containing HMG-box domains, hUBF (H. M. Jantzen et al., *Nature* 344:830-836 (1990)). The location of the HMG box is indicated in FIG. 14. Optimal alignment of human cisplatin-DNA SSRP (Seq. ID No. 7) with human HMG1 revealing 47% identity in the regions compared. Homology was also found between SSRP and other HMG-box proteins which have been recently reported. See H. M. Jantzen et al., *Nature* 344:830-836 (1990); A. H. Sinclair et al., *Nature* 346:240-244 (1990); J. Gubbay et al., *Nature* 346:245-250 (1990); Parisi, M. A. & Clayton, D. A. *Science* 25:965-968 (1991); A. Travis et al., *Genes & Dev.* 5:880-894 (1991); M. L. Waterman et al., *Genes & Dev.* 5:656-669 (1991); J. F. Diffley et al., 88:7864-7868 (1991). It is important to note, however, that no obvious consensus HMG-box sequence emerges from such a comparison. In addition, the acidic region of SSRP (Seq. ID No. 7) has limited homology to nucleolin, (M. Srivastava et al., *FEBS Lett.* 250:99-105 (1989)) which is involved in transcriptional control of rRNA genes.

The human map position of the SSRP (Seq. ID No. 6) was also determined, using a panel of human chromosome-specific human-rodent hybrids. Initial experiments placed the gene on chromosome 11. Further refinement with a series of hybrid cell lines containing only small defined segments of human chromosome 11 on a rodent genomic background (Glaser, T. Ph.D. dissertation, Massachusetts Institute of Technology (1989)) localized the position of the clone to 11q12. Placement of the sequence on the long arm of human chromosome 11 is particularly interesting because the murine homolog to SSRP has been mapped to mouse chromosome 2 (M. Shirakata et al., *Molecular and Cellular Biology* 11:4528-4536 (1991)). Previously, a syntonic relationship had been demonstrated only for mouse chromosome 2 and human chromosome 11p (J. H. Nadeau et al., *Mamm. Genome* 1:S461-S515 (1991)).

EXAMPLE T

Use of the human cDNA Clone λPt2 to Obtain the Full Length *Drosophila melanogaster* homolog of human SSRP In view of the expression pattern and evolutionary conservation of the SSRP gene, indicating a protein with an in vivo role important for normal biological functions, at least one SSRP homolog from a lower species was desired in order to further delineate conserved domains likely to be critical for SSRP function. Accordingly, a *D. melanogaster* head cDNA library was screened using the human cDNA clone λPt2 (Seq. ID No. 9) (radiolabelled as described in Example O), under low stringency conditions according to the following procedure:

Library Screening

For the primary screen of the Drosophila head cDNA library (N. Itoh, et al., *Proc. Natl. Acad. Sci. USA* 83:4081 (1986)), $5 \times 10^6$ recombinant phage were plated on *E. coli* host strain Y1088. Duplicate replica nitrocellulose filters were prepared and subsequently denatured (0.5M NaOH, 1.5M NaCl), neutralized (1M Tris (pH 7.4), 1.5M NaCl), and rinsed with 2X SSC (20 X SSC: 3M NaCl, 0.3M $Na_3C_6H_5O_7$). Baking for two hours at 80° C. in a vacuum oven was followed by pre-incubation at 42° C. for 4 hours with hybridization fluid (30% formamide, 1M NaCl, 50 mM Tris (pH 7.5), 0.5% SDS, 10% Dextran Sulfate, 1X Denhardt's, and 1 mg/ml denatured salmon sperm DNA). Labelled λPt2 (Seq. ID No. 9) probe was added to a final concentration of $1 \times 10^6$ cpm of labelled DNA per ml of hybridization fluid and incubation continued for 16 hours. The filters were washed once at room temperature in 2X SSC/0.1% SDS, twice at 55° C. in 2X SSC/0.1% SDS, and twice at 55° C. in 1X SSC/0.1% SDS for fifteen minutes each. After the washing was completed the filters were air dried briefly and analyzed by autoradiography. Plaque pure bacteriophage clones were isolated by multiple rounds of screening. Single plaques were amplified in liquid culture for DNA preparation and further analysis.

Ten Drosophila cDNA clones were identified, with varying degrees of hybridization to the human cDNA. These bacteriophage clones were isolated and purified through successive rounds of screening. Two of these, denoted DM 3002 and DM 1001, were chosen for further study based on their strong hybridization to the human clone and their large size relative to other clones. Restriction and sequence analyses of these clones is described in the Examples which follow.

EXAMPLE U

Southern Blotting Analysis of Overlapping cDNAs Encoding Drosophila SSRP

Southern Analysis

DNA from each species (human and fly) was digested to completion with EcoRI and the fragments were separated by electrophoresis in 0.8% agarose gels. The gel was then denatured for 45 minutes (0.5M NaOH, 1.5M NaCl), neutralized for 60 minutes (1M Tris (pH 7.4), 1.5M NaCl) and the DNA transferred to Zetabind TM membrane (Cuno) by capillary action for 16 hours in 10X SSC. After rinsing the filter with 2X SSC, it was baked in a vacuum oven at 80° C. for 2 hours. Following pretreatment at 65° C. for one hour (0.5X SSC, 0.5% SDS), the filters were hybridized and washed as described above for library screening.

Figure 15:
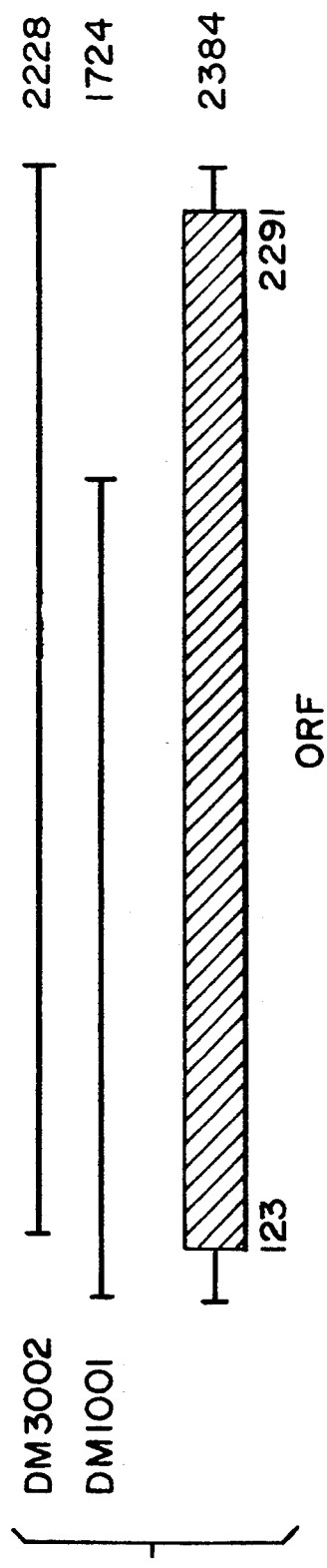
FIG. 15 is a schematic illustration showing the relationship between Drosophila melanogaster cDNA clones DM 3002 and DM 1001.

EcoRI digestion of the bacteriophage clones, DM 3002 and DM 1001, with EcoRI released a 2.3 kb insert from DM 3002, and two fragments of size 1.4 and 1.8 kb from clone DM 1001. These three fragments were gel purified, subcloned individually and subjected to sequence analysis (described below), as well as restriction endonuclease mapping. Sequence analysis of the three subcloned fragments confirmed that there was significant overlap between DM 3002 and the 1.8 kb EcoRI fragment of DM 1001. Northern analysis of the two EcoRI fragments of DM 1001 indicated that the 1.4 kb fragment recognized two head-specific RNA species of 3.5 and 1.6 kb. However, rehybridization of this blot with the 1.8 kb EcoRI fragment revealed that these RNA species were not recognized by this portion of the clone, indicating that clone DM 1001 was a chimera. Therefore, the 1.4 kb EcoRI fragment was not considered further. FIG. 15 shows the alignment of clones DM 3002 and the 1.8 kb EcoRI fragment of DM 1001.

EXAMPLE V

Sequencing of Drosophila cDNAs Encoding SSRP and Characterization Thereof

Subcloning and sequencing of the D. melanogaster cDNA sequences was carried out essentially as described above in Example S. Clones DM 3002 and 1001 were sequenced completely in both directions; as noted above, significant overlap between DM 3002 and the 1.8 kb EcoRI fragment of DM 1001 was observed.

The sequences of clones DM 3002 and the 1.8 kb fragment of DM 1001 were combined to create a composite sequence of 2384 bases (Seq. ID No. 10). Interestingly, there are large open reading frames in both directions from bases 123–2291 and from bases 2300–600. The larger of the two open reading frames predicts a 723 amino acid protein of molecular weight 81 524 daltons (Seq. ID No. 11) which shows extensive homology to the human structure specific recognition protein (Seq. ID No. 7), the cDNA of which was used as a probe. For this reason, the 81 kD protein was assumed to be the correct reading frame. The AUG codon at position 123 of this open reading frame is believed to be the true start site, both because there is an inframe stop codon upstream from this site and because the start site is the same as for the human protein. No consensus polyadenylation signal is seen within the 93 bases of 5' untranslated sequence. It seems clear, however, that the complete coding sequence of the Drosophila homolog (Seq. ID No. 10) of human cis-DDP SSRP is contained within the clones sequenced.

The homology at the nucleotide level between the human (Seq. ID No. 6) and Drosophila (Seq. ID No. 10) cDNAs is 54%, and this similarity is confined mainly to the coding regions of the sequences. The homology in the 5' and 3' untranslated regions is 32% and 37%, respectively, whereas the predicted amino acid sequences of the two species' SSRPs share 53% identity and 72% similarity at the amino acid level over their entire length. Moreover, the sizes of the two SSRPs are quite comparable, and both contain a large number of charged amino acids (36% for the human protein and 38% for the Drosophila protein). However, the Drosophila protein is more acidic than the human protein with an isoelectric point of 5.40. Both proteins have their charged residues concentrated within small discrete regions, and these domains are conserved, depicted schematically in FIG. 16.

A search of the PROSITE database revealed one potential glycosylation site and several potential phosphorylation sites which are conserved between these proteins. An asparagine residue which fits the consensus for glycosylation (R. D. Marshall, *Ann. Rev. Biochem.,* 41:673 (1972)) is at position 567 in the Drosophila protein and at position 559 in the human protein (Seq. ID No. 7). At position 324 in both proteins there is a conserved threonine residue with the two required amino terminal basic residues which is potentially phosphorylated by cyclic AMP-dependent protein kinase (J. R. Feramisco, et al., *J. Bio. Chem.,* 255:4240 (1980); D. B. Glass, et al., *Bio. Chem.,* 261:2987 (1986)). Also conserved are five sites consisting of a serine residue with an amino acid at the +3 position which fit the consensus sequence for phophorylation by casein kinase II (O. Marin et al., *Eur. J. Biochem.,* 160:230 (1986); E. A. Kuenzel et al., *J. Bio. Chem.,* 262:9136 (1987)). These serines are at positions 80 and 399 in both proteins, and at positions 443, 472 and 670 in the Drosophila protein (Seq. ID No. 11), equivalent to positions 444, 474, and 672 in the human protein (Seq. ID No. 7). Protein kinase C requires a basic amino acid two positions away from the phosphorylated serine or threonine residue on the carboxy terminal side of the protein (A. Kishimoto et al., *J. Bio. Chem.,* 260:12492 (1985); J. R. Woodgett et al., *Eur. J. Biochem.,* 161:177 (1986)). There are seven such sites conserved between these proteins at positions 37, 111, 141, 209, 344, and 385 in both proteins and at position 636 in the Drosophila protein (Seq. ID No. 11), equivalent to position 627 in the human protein (Seq. ID No. 7).

Using the BLAST Network Service at the National Center for Biotechnology Information (S. F. Altschul, *J. Mol. Biol.,* 215:403 (1990)), a nonredundant search of protein databases with the predicted Drosophila amino acid sequence (Seq. ID No. 11) revealed homologies consistent with the human protein (Seq. ID No. 7). The DNA structure-specific recognition protein showed homology to HMG-1 and -2 proteins from several species, and to a transcription factor protein (hUBF) which contains an HMG box. As was found for the human protein sequence, the highly charged domains of the protein proved to be homologous to highly charged domains of other proteins, especially the transcriptional regulator nucleolin.

Computer analysis for the presence of potential structural domains was also carried out. For both the human protein (Seq. ID No. 7) and its Drosophila homolog (Seq. ID No. 11), Chou and Fasman analysis of hydropathy (P. Y. Chou and G. D. Fasman, *Biochem.,* 13:211

(1974); (P. Y. Chou, and G. D. Fasman, *Ann. Rev. Biochem.*, 47:251 (1978) predicts the entire carboxy terminal half of the proteins, from aa 400 to the end, to be highly hydrophilic. No major regions of amphiphilicity are apparent in either protein. Comparison of secondary structural predictions for the human protein and its Drosophila homolog reveal a number of regions that appear to be helical in both proteins when analyzed either with the method of Chou and Fasman (P. Y. Chou and G. D. Fasman, *Biochem.*, 13:211 (1974); (P. Y. Chou and G. D. Fasman, *Ann. Rev. Biochem.*, 47:251 (1978) or with the method of Robson and Garnier (B. Robson and E. Suzuki, *J. Mol. Biol.* 107:327 (1976); (J. Garnier, et al., *J. Mol. Biol.* 120:97 (1978)). Specifically, these regions surround approximately aa75–105, 150–165, 290–300, 405–425, 450–465, 480–495, 525–540, 580–620, and 675–690.

EXAMPLE W

In situ Hybridization Studies of the Drosophila SSRP Gene

In situ Hybridization to Polytene Chromosomes

Polytene chromosomes were prepared from the salivary glands of third instar larvae as described previously (M. Ashburner, *Drosophila: A Laboratory Manual* pp. 37–47 (1989)). Nick translation of plasmid DNA containing clone DM 3002 with biotinylated-16-dUTP (ENZO Diagnostics), detection with Streptavidin-biotinylated peroxidase (Detek-1-HRP, ENZO Diagnostics), and hybridization steps were all performed with standard techniques (M. Ashburner, *Drosophila: A Laboratory. Manual* pp. 37–47 (1989)).

The results of this study placed the Drosophila clone (Seq. ID No. 10) on the right arm of chromosome 2, in band 60A 1–4. Deficiencies in this region, specifically from 59D4–5; 50A1-2 and 59D8–11; 60A7 produce maternal effect mutations that are female steriles (T. Schupbach and E. Weischaus, *Genetics*, 121:101 (1989)). Interestingly, the egalitarian gene which also maps to the region, is required for oocyte differentiation (P. F. Lasko and M. Ashburner, *Genes and Dev.*, 4:905 (1990)). Other mutants which map to the region include abbreviated and forkoid, which affect bristle formation, and lanceloated, which elongates the wing (Diaz-Benjumea and A. Garcia-Bellido, *Roux's Arch. Dev. Biol.*, 198:336 (1990)). The Drosophila guanine nucleotide-binding protein $G_s\alpha$, also maps to position 60A on polytene chromosomes (F. Quan, et al., *Proc. Natl. Acad. Sci. USA* 86:4321 (1989)). Recently, a member of the transforming growth factor-$\beta$ family, denoted the 60A gene, has also been mapped to this region. K. A. Wharton, et al., submitted for publication.

EXAMPLE Y

EMSA and Modified Western Blotting Studies of Yeast Cell Extracts

Purification of Pt-DNA mobility shift activity

Yeast cells (BJ 296) were grown to late log phase (O.D. 0.8) in 6 L YPD and harvested by centrifugation for 15 minutes at 5000 g. The yield was 60 G wet cells. The pellet was washed once with water and resuspended in 180 mL TM (50 mM Tris-HCl (pH 8) 12.5 mM $MgCl_2$, 1 mM EDTA, 1 mM DTT and 20% glycerol) buffer containing 0.1M KCl, 100 mM PMSF, 10mg/ml leupeptin and 1 mg/mL pepstatin. After two passages through a french press at 24,000 psi the lysate was cleared of debris by centrifugation at 14,000 g for 5 minutes. Ammonium sulfate (15.2 g, 25% saturation) was added to the supernatant (190 mL) and the solution was stirred for 30 minutes on ice. Following centrifugation at 14,000 g for 10 minutes, ammonium sulfate (34.2 g, 55% saturation) was added. The precipitated proteins were collected by centrifugation, dissolved in TM buffer 0.1M KCl, 1 mM PMSF and desalted on a Biorad P-6 size-exclusion column. The resulting solution was loaded onto either a DEAE-sepharose or a S-sepharose column. The columns were washed with TM buffer, 0.1M KCl and eluted with a TM buffer 0.1 to 1.0M KCl gradient. Bandshift active fractions from these columns were diluted to 0.1 MKCl with TM buffer, loaded onto a heparin fast-flow column (BioRad) and eluted with a 0.1–1.0M KCl gradient.

Bandshift assay (EMSA)

15 $\mu$L aliquots of selected fractions from the column chromatography were mixed in solutions containing 10 mM Tris-HCl 10 mM NaCl, 0.5 mM EDTA, 1 mM DTT and 20% glycerol, 0.2 $\mu$g/mL poly(dIdC) and 1000 cpm of a [$^{32}$P] end-labeled 123 bp DNA fragment. For platinated samples, the ratio of cis-DDP/nucleotide was 0.021. The reactions were incubated at 25° C. for 15 minutes, loaded onto 8% TBE polyacrylamide gels and electrophoresed at 4° C. Dried gels were exposed to Kodax X-AR film. Bandshift activity was quantified using a Molecular Dynamics phosphor-imager.

Modified Western Analysis

Proteins were resolved on SDS-polyacrylamide gels and electroblotted to nitrocellulose filters. The filters were treated with blotto (50 mM Tris HCl pH 7.5, 50 mM NaCl, 1 mM EDTA, 5% nonfat dry milk powder) for 1 hour, washed twice for 10 minutes with TNE 50 (10 mM Tris pH 7.5, 50 mM NaCl, mM EDTA, 1 mM DTT) and denatured (50 mM Tris HCl pH 8.0, 7M guanidine HCl, 1 mM EDTA, 50 mM DTT, and 5% (v/v) blotto) for 1 hour. Following overnight renaturation (50 mM Tris HCl pH 8.0, 50 mM NaCl, 1 mM EDTA, 2 mM DTT, 0.1% Nonidet P-40 and 5% (v/v) blotto) the filters were washed with 5% dry milk in 20 mM HEPES pH 7.5. The filters were incubated for two hours in 30 mM HEPES, 10 mM $MgCl_2$, 0.25% dry milk, 20 $\mu$g/mL poly(dIdC).poly(dIdC) and $1 \times 10^6$ cpm/mL [$^{32}$P] endlabeled probe. Excess probe was removed by washing the filters twice for 10 minutes at 4° C. with a 30 mM HEPES, 0.25% dry milk solution.

In an initial experiment to determine conditions required to purify the yeast SSRP protein(s), $(NH_4)_2SO_4$ was added to 25%, 40% and 60% saturation. The proteins precipitating at the various $(NH_4)_2SO_4$ concentrations were analyzed by modified Western (i.e., Southwestern) blotting, and corroborated by EMSA. As assessed by Southwestern blot, an 82 000 dalton protein is present in the yeast whole cell extract, was well as in the 0–25%, 25–40% and 40–60% $(NH_4)_2SO_4$ saturation fractions. This band is apparently absent from the supernatant. In addition, a rather large protein, ~190 kDa, came down in the clearing spin, preceding the $(NH_4)_2SO_4$ precipitations. A parallel blot was probed with unmodified DNA; no DNA binding was observed on it. EMSA analysis of the same samples showed that the 40–60% fraction apparently contains the highest mobility-shift activity, but activity is also present in the 25–40% fraction and the supernatant.

Further purification of the bandshift activity was achieved with S-sepharose chromatography. In one preparation, the 25–60% proteins were redissolved, desalted by dialysis or gel filtration, loaded onto a S- sepharose column, and eluted with a 0.1-1.0M KCl gradient. It was found that bandshift activity elutes in two peaks with a complex pattern of shifted probe. Samples of the fractions representing the peaks of activity by EMSA were pooled and subjected to modified Western blotting. This study showed an enrichment of two proteins having electrophoretic mobilities consistent with masses of 42 000 and 40 000 daltons.

EXAMPLE Z

EMSA and Modified Western Blotting Studies of the Polypeptide Encoded by Yeast SSRP Clone λyPt Fusion Protein Preparation Stable lysogens of λyPt (Seq. ID No. 12) and μgt11 were prepared in Y1090 E. coli cells. Lysogens were grown in LB at 32° C. to OD 0.5 when the temperature was shifted to 42° C. for 20 minutes. The β-galactosidase fusion protein was induced by adding to IPTG (10 mM). Two methods were used to harvest total protein: Method A, cells were harvested 1 hour after IPTG induction, by centrifugation and resuspended in 0.01 volumes of TM buffer containing 100 mM PMSF and flash frozen in liquid nitrogen; Method B, 2.0 mL aliquots were harvested by centrifugation at 10 minutes intervals following the IPTG treatment, resuspended in SDS-PAGE loading buffer, placed in boiling water for 5 minutes and stored at −80° C. Cell debris was removed by centrifugation from samples prepared by either method immediately prior to SDS-polyacrylamide gel electrophoresis.

The fusion protein produced by the lysogen of λyPt (Seq. ID No. 12) in Y1090 is capable of binding cis-DDP modified DNA on a modified Western blot (using essentially the same procedure as discussed in the preceeding Example). The fusion protein was observed to have an electrophoretic mobility consistent with a protein of 180 000 daltons. Since the β-galactosidase portion of this polypeptide accounts for 113 000 daltons, the remaining 63 000 daltons is the expression product of the cloned gene. It should be noted that this fusion protein has proven to have uncertain stability (i.e., Southwestern blotting reveals the presence of multiple reactive bands, presumably arising from proteolysis).

EXAMPLE AA

Subcloning, Sequencing and Sequence Characterization of Yeast SSRP Clone λyPt

Subcloning and DNA Sequencing

The 1.7, 1.1 and 0.6 kB EcoRI fragments from λyPt (Seq. ID No. 12) were ligated into the EcoRI site of pBluescript IISK+ yielding plasmids pSB1, pSB2 and pSB3, respectively. Plasmid DNA was alkaline denatured for the sequencing reactions. Double-stranded λyPt (Seq. ID No. 12) DNA was prepared for sequencing by SacI digestion and treatment with T7 gene 6 exonuclease to produce a single-stranded DNA template. Sequencing was performed by the dideoxy chain termination method using sequenase T7 DNA polymerase (US Biochemical Corp.). Sequence fragments were assembled using the GCG program. (Devereux, Haberli, et al. (1984) *Nucleic Acids Research* 12(1):387-395. Nonredundant searches or protein and DNA sequence databases were performed with the BLAST network service provided by the National Center for Biotechnology Information (NCBI).

Complete sequencing of λyPt (Seq. ID No. 12) was achieved by sequencing the three subcloned EcoRI fragments identified above. Since EcoRI digestions of λyPt DNA releases three fragments, the cloned DNA apparently contains two internal EcoRI sites (further details are given below). The yeast genomic DNA contained in λyPt was found to total 3292 bases (Seq. ID No. 13). An open reading frame, contiguous with the reading frame for the α-galactosidase gene of lamda phage, is found in the λyPt DNA sequence. This reading frame extends from bases 1 to 1626. The hexanucleotide polyadenylation signal, AATAAA, found at nucleotides 1632-1637, is present in approximately 50% of S. cerevisiae genes (Hyman, L., S. H. Seiler et al. (1991) *Mol. Cell. Biol.* 11(4):2004-2012).

Translation of the open reading frame found in clone λyPt yields an amino acid sequence of 534 residues (Seq. ID No. 13). This peptide sequence is herein referred to as fySSRP(Seq. ID No. 13), for fractional yeast structure specific recognition protein. Examination of the amino acid sequence of fySSRP reveals a striking feature: there are eight runs of five or more glutamines, of which the longest is fifteen. In all, there are 110 glutamine residues, or one fifth of the total. Fifty asparagine residues account for another 9.2% of the amino acids.

EXAMPLE BB

Expression of the Yeast SSRP Gene

Probe Preparation

The 0.6, 1.1 or 1.7 EcoRI fragments from pSB1, pSB2 or pSB3 were used as templates for probe preparation. Approximately 0.2 μg of DNA in low melting point agarose was boiled with 0.1 μg d(N)$_6$ oligonucleotides (New England Biolabs), and labeled with α-[$^{32}$P]dCTP by E. coli DNA polymerase I (Klenow fragment). Reactions were stopped by extraction with phenol/chloroform.

Northern Analysis

Total yeast RNA was prepared by the published procedure. (Kohrer, K. and H. Domdey (1991) *Guide to Yeast Genetics* San Diego, Academic Press Inc. 398–405). RNA MW markers (BRL Inc.) and 10 μg total yeast RNA were subjected to electrophoretic analysis in 0.8% agarose gels containing 6% formaldehyde, 20 mM MOPS, 5 mM NaOAc, and 1 mM EDTA. Gels were denatured for 15 mins. in 50 mM NaOH, 100 mM NaCl, neutralized in 100 mM Tris (pH 7.5), and transferred to nitrocellulose by capillary action in 20X SSC. Filters were baked for two hrs. at 80° C. The filter was prehybridized (50% formamide, 0.1% NaPO$_4$, 50 mM Tris (pH 7.5), 5X Denhardt's solution, 0.5% SDS, and 100 μg/ml denatured salmon sperm DNA) for four hours at 42° C. and hybridized overnight in prehybridization solution containing 10% dextran sulfate and with 1×10$^6$ cpm/mL of labeled DNA probe. Filters were washed at 55° C. twice for 30 mins. with 2X SSC, 0.1% SDS twice, and in 1X SSC, 0.1% SDS and exposed to X-ray film.

Northern blotting analysis established that ySSRP (Seq. ID No. 13) is encoded by a 2.1 kb mRNA species.

EXAMPLE CC

Southern Blotting Studies of Clone λyPt

Southern Analysis

Typically, 10 μg of genomic yeast DNA or lamda DNA were treated with restriction enzymes and the fragments resolved by electrophoresis on 0.8% agarose gels. Gels were treated with 0.2N HCl for 10 min., denatured for 20 minutes (0.5M NaOH, 1.5M NaCl), and neutralized for 40 minutes with two changes of 1M Tris pH 7.5, 1.5M NaCl. The DNA was transferred to nitrocellulose filters (Schleicher and Schuell) by capillary transfer overnight with 20X SSC (i.e., 3M NaCl, 0.3M sodium citrate). The filters were baked for 2 hours at 80° C., prehybridized (50% formamide, 5X SSC, 1X Denhardt's solution 1 mg/mL denatured calf thymus DNA) for 8 hours at 42° C. and hybridized (50% formamide, 5X SSC, 1X Denhardt's solution 1 mg/mL denatured calf thymus DNA, 10% dextran sulfate, $1 \times 10^6$ cpm/mL probe (see the preceeding Example)) overnight. Thereafter, filters were washed twice for 15 minutes with 2X SSC, 0.1% SDS and twice for 15 minutes with 0.5X SSC, 0.1% SDS. Results were visualized by autoradiography.

Southern analysis of λyPt (Seq. ID No. 12) and yeast genomic DNA digested with EcoRI and probed with the 0.6 kB fragment revealed that a 0.6 kB piece is present in both digests. Therefore, the 0.6 kB piece is located in the middle of the cloned DNA. The 0.6 and 1.1 kB EcoRI fragments were oriented to each other by sequencing λyPt DNA. The orientation of the 1.7 kB EcoRI fragment was determined by Southern analysis of yeast genomic DNA digested with PstI and EcoRV, probed with the 0.6 kB EcoRI fragment. A 2.3 kB piece hybridized on this blot, locating the EcoRV restriction site in the 1.7 kB fragment towards the 3' end of the clone. In the other possible orientation, with the EcoRV site closer to the 5' end, a 1.2 kB fragment would have been released by DNA digested with PstI and EcoRV.

EQUIVALENTS

Those skilled in the art will recognize, or be able to ascertain using no more than routine experimentation, many equivalents to the specific embodiments of the invention described herein. Such equivalents are intended to be encompassed by the following claims.

---

We claim:

1. Isolated DNA or RNA encoding a eukaryotic DNA structure specific recognition protein having the following properties:
   (a) selective binding to a double-stranded DNA fragment having at least one region of DNA damage comprising a 1,2-intrastrand d(ApG) or d(GpG) dinucleotide adduct, to form a (damaged DNA fragment):(protein) complex which has a retarded electrophoretic mobility relative to the mobility of the damaged DNA fragment alone; and
   (b) when affixed to a solid support, said protein binds selectively to a double-stranded DNA fragment having at least one region of DNA damage comprising a 1,2-intrastrand d(ApG) or d(GpG) dinucleotide adduct, and not to a double-stranded DNA fragment lacking said region of DNA damage.

2. Isolated DNA of claim 1, the nucleotide sequence of which comprises a sequence selected from the group consisting of:
   (a) SEQ ID No. 6;
   (b) a sequence that encodes the amino acid sequence of SEQ ID No. 7;
   (c) a sequence that specifically hybridizes to SEQ ID No. 6;
   (c) SEQ ID No. 8;
   (e) SEQ ID No. 9;
   (f) a sequence that specifically hybridizes to SEQ ID No. 8;
   (g) a sequence that specifically hybridizes to SEQ ID No. 9
   (h) the HMG box domain of SEQ ID No. 6;

(i) a sequence that encodes the amino acid sequence of the HMG box domain of SEQ ID No. 7; and (j) a sequence that specifically hybridizes to the HMG box domain of SEQ ID No. 6.

3. Isolated RNA transcribed from the DNA of claim 2.

4. Isolated DNA or RNA of claim 1 encoding a human DNA structure specific recognition protein, wherein the sequence of said DNA or RNA predicts a 710 amino acid protein, further wherein said protein comprises an HMG box domain.

5. An expression vector comprising the DNA of claim 1 or 2.

6. A host cell transfected with the expression vector of claim 5.

7. A nucleotide probe that specifically hybridizes to a nucleotide sequence selected from the group consisting of:

(a) cDNA encoding a human DNA structure specific recognition protein having the following properties:
  (i) selective binding to a double-stranded DNA fragment having at least one region of DNA damage comprising a 1,2-intrastrand d(ApG) or d(GpG) dinucleotide adduct, to form a (damaged DNA fragment):(protein) complex which has a retarded electrophoretic mobility relative to the mobility of the damaged DNA fragment alone; and
  (ii) when affixed to a solid support, said protein binds selectively to a double-stranded DNA fragment having at least one region of DNA damage comprising a 1,2-intrastrand d(ApG) or d(GpG) dinucleotide adduct, and not to a double-stranded DNA fragment lacking said region of DNA damage;

(b) SEQ ID No. 6;

(c) SEQ ID No. 8;

(d) SEQ ID No. 9 and (e) the HMG box domain of SEQ ID No. 6.

8. A method of detecting, in eukaryotic cells, nucleic acid encoding a DNA structure specific recognition protein having the following properties:

(i) selective binding to a double-stranded DNA fragment having at least one region of DNA damage comprising a 1,2-intrastrand d(ApG) or d(GpG) dinucleotide adduct, to form a (damaged DNA fragment):(protein) complex which has a retarded electrophoretic mobility relative to the mobility of the damaged DNA fragment alone; and (ii) when affixed to a solid support, said protein binds selectively to a double-stranded DNA fragment having at least one region of DNA damage comprising a 1,2-intrastrand d(ApG) or d(GpG) dinucleotide adduct, and not to a double-stranded DNA fragment lacking said region of DNA damage, said method comprising the steps of:
  (a) treating eukaryotic cells in such a manner as to produce an extract containing nucleic acid from the cells;
  (b) contacting the extract with a nucleotide probe that specifically hybridizes to cellular DNA encoding said DNA structure specific recognition protein; and
  (c) detecting hybridization.

9. A method of claim 8 wherein the nucleotide probe specifically hybridizes to a nucleotide sequence selected from the group consisting of:
  (a) human cDNA encoding said DNA structure specific recognition protein;
  (b) SEQ ID No. 6;
  (c) SEQ ID No. 8;
  (d) SEQ ID No. 9 and
  (e) the HMG box domain of SEQ ID No. 6.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( C ) INDIVIDUAL ISOLATE: Synthetic oligonucleotide ( i x ) FEATURE:
        ( A ) NAME/KEY: miscdifference
        ( B ) LOCATION: replace(11..12)
        ( D ) OTHER INFORMATION: /label=Pt- DNA
            / note="cis-{Pt(NH3)3}1,2-d(GpG) intrastrand Platinated DNA Structural Motif"

( x i ) SEQUENCE DESCRIPTION: SEQ ID NO:1:

TCTCCTTCTT GGTTCTCTTC TC                      2 2

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( C ) INDIVIDUAL ISOLATE: Synthetic oligonucleotide ( i x ) FEATURE:
        ( A ) NAME/KEY: miscdifference
        ( B ) LOCATION: replace(11..12)
        ( D ) OTHER INFORMATION: /label=Pt- DNA
            / note="cis-{Pt(NH3)2}1,2-d(ApG) intrastrand Platinated DNA Structural Motif"

( x i ) SEQUENCE DESCRIPTION: SEQ ID NO:2:

TCTCCTTCTT AGTTCTCTTC TC                      2 2

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( C ) INDIVIDUAL ISOLATE: Synthetic oligonucleotide ( i x ) FEATURE:
        ( A ) NAME/KEY: miscdifference
        ( B ) LOCATION: replace(11..13)
        ( D ) OTHER INFORMATION: /label=Pt- DNA
               / note="cis-{Pt(NH3)2}1,3-d(GpTpG) intrastrand
               Platinated DNA Structural Motif"

( x i ) SEQUENCE DESCRIPTION: SEQ ID NO:3:

TCTCCTTCTT GTGTCTCTTC TC                                        22

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( C ) INDIVIDUAL ISOLATE: Synthetic oligonucleotide ( i x ) FEATURE:
        ( A ) NAME/KEY: miscdifference
        ( B ) LOCATION: replace(11..13)
        ( D ) OTHER INFORMATION: /label=Pt- DNA
               / note="trans-{Pt(NH3)2}1,3-d(GpTpG) intrastrand
               Platinated DNA Structural Motif"

( x i ) SEQUENCE DESCRIPTION: SEQ ID NO:4:

TCTCCTTCTT GTGTCTCTTC TC                                        22

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( C ) INDIVIDUAL ISOLATE: Synthetic oligonucleotide ( i x ) FEATURE:
        ( A ) NAME/KEY: miscdifference
        ( B ) LOCATION: replace(12)
        ( D ) OTHER INFORMATION: /label=Pt- DNA
               / note="cis-{Pt(NH3)2(N3-cytosine)}dG
               monofunctional Platinated DNA Structural Motif"

( x i ) SEQUENCE DESCRIPTION: SEQ ID NO:5:

TCTCCTTCTT CGTTCTCTTC TC                                        22

( 2 ) INFORMATION FOR SEQ ID NO:6:

( i ) SEQUENCE CHARACTERISTICS:
        ( A ) LENGTH: 2839 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
    ( A ) ORGANISM: Homo sapiens ( v i i ) IMMEDIATE SOURCE:
    ( B ) CLONE: human SSRP - composite of six overlapping cDNA clones ( v i i i ) POSITION IN GENOME:
    ( A ) CHROMOSOME/SEGMENT: 11q12

( i x ) FEATURE:
    ( A ) NAME/KEY: CDS
    ( B ) LOCATION: 275..2404

( x i ) SEQUENCE DESCRIPTION: SEQ ID NO:6:

```
GAATTCCGTA CGGCTTCCGG TGGCGGGACG CGGGGCCGCG CACGCGGGAA AAGCTTCCCC    60

GGTGTCCCCC CATCCCCCTC CCCGCGCCCC CCCCGCGTCC CCCCAGCGCG CCCACCTCTC   120

GCGCCGGGGC CCTCGCGAGG CCGCAGCCTG AGGAGATTCC CAACCTGCTG AGCATCCGCA   180

CACCCACTCA GGAGTTGGGG CCCAGCTCCC AGTTTACTTG GTTTCCCTTG TGCAGCCTGG   240

GGCTCTGCCC AGGCCACCAC AGGCAGGGGT CGAC ATG GCA GAG ACA CTG GAG       292
                                       Met Ala Glu Thr Leu Glu
                                        1               5

TTC AAC GAC GTC TAT CAG GAG GTG AAA GGT TCC ATG AAT GAT GGT CGA    340
Phe Asn Asp Val Tyr Gln Glu Val Lys Gly Ser Met Asn Asp Gly Arg
            10                  15                  20

CTG AGG TTG AGC CGT CAG GGC ATC ATC TTC AAG AAT AGC AAG ACA GGC    388
Leu Arg Leu Ser Arg Gln Gly Ile Ile Phe Lys Asn Ser Lys Thr Gly
        25                  30                  35

AAA GTG GAC AAC ATC CAG GCT GGG GAG TTA ACA GAA GGT ATC TGG CGC    436
Lys Val Asp Asn Ile Gln Ala Gly Glu Leu Thr Glu Gly Ile Trp Arg
    40                  45                  50

CGT GTT GCT CTG GGC CAT GGA CTT AAA CTG CTT ACA AAG AAT GGC CAT    484
Arg Val Ala Leu Gly His Gly Leu Lys Leu Leu Thr Lys Asn Gly His
 55                  60                  65                  70

GTC TAC AAG TAT GAT GGC TTC CGA GAA TCG GAG TTT GAG AAA CTC TCT    532
Val Tyr Lys Tyr Asp Gly Phe Arg Glu Ser Glu Phe Glu Lys Leu Ser
                75                  80                  85

GAT TTC TTC AAA ACT CAC TAT CGC CTT GAG CTA ATG GAG AAG GAC CTT    580
Asp Phe Phe Lys Thr His Tyr Arg Leu Glu Leu Met Glu Lys Asp Leu
            90                  95                 100

TGT GTG AAG GGC TGG AAC TGG GGG ACA GTG AAA TTT GGT GGG CAG CTG    628
Cys Val Lys Gly Trp Asn Trp Gly Thr Val Lys Phe Gly Gly Gln Leu
        105                 110                 115

CTT TCC TTT GAC ATT GGT GAC CAG CCA GTC TTT GAG ATA CCC CTC AGC    676
Leu Ser Phe Asp Ile Gly Asp Gln Pro Val Phe Glu Ile Pro Leu Ser
    120                 125                 130

AAT GTG TCC CAG TGC ACC ACA GGC AAG AAT GAG GTG ACA CTG GAA TTC    724
Asn Val Ser Gln Cys Thr Thr Gly Lys Asn Glu Val Thr Leu Glu Phe
135                 140                 145                 150

CAC CAA AAC GAT GAC GCA GAG GTG TCT CTC ATG GAG GTG CGC TTC TAC    772
His Gln Asn Asp Asp Ala Glu Val Ser Leu Met Glu Val Arg Phe Tyr
                155                 160                 165

GTC CCA CCC ACC CAG GAG GAT GGT GTG GAC CCT GTT GAG GCC TTT GCC    820
Val Pro Pro Thr Gln Glu Asp Gly Val Asp Pro Val Glu Ala Phe Ala
            170                 175                 180

CAG AAT GTG TTG TCA AAG GCG GAT GTA ATC CAG GCC ACG GGA GAT GCC    868
Gln Asn Val Leu Ser Lys Ala Asp Val Ile Gln Ala Thr Gly Asp Ala
        185                 190                 195

ATC TGC ATC TTC CGG GAG CTG CAG TGT CTG ACT CCT CGT GGT CGT TAT    916
Ile Cys Ile Phe Arg Glu Leu Gln Cys Leu Thr Pro Arg Gly Arg Tyr
```

-continued

|  |  |  |  | 200 |  |  |  |  | 205 |  |  |  |  | 210 |  |  |  |
|---|---|---|---|---|---|---|---|---|---|---|---|---|---|---|---|---|---|
| GAC | ATT | CGG | ATC | TAC | CCC | ACC | TTT | CTG | CAC | CTG | CAT | GGC | AAG | ACC | TTT |  | 964 |
| Asp | Ile | Arg | Ile | Tyr | Pro | Thr | Phe | Leu | His | Leu | His | Gly | Lys | Thr | Phe |  |  |
| 215 |  |  |  | 220 |  |  |  |  | 225 |  |  |  |  | 230 |  |  |  |
| GAC | TAC | AAG | ATC | CCC | TAC | ACC | ACA | GTA | CTG | CGT | CTG | TTT | TTG | TTA | CCC |  | 1012 |
| Asp | Tyr | Lys | Ile | Pro | Tyr | Thr | Thr | Val | Leu | Arg | Leu | Phe | Leu | Leu | Pro |  |  |
|  |  |  |  | 235 |  |  |  |  | 240 |  |  |  |  | 245 |  |  |  |
| CAC | AAG | GAC | CAG | CGC | CAG | ATG | TTC | TTT | GTG | ATC | AGC | CTG | GAT | CCC | CCA |  | 1060 |
| His | Lys | Asp | Gln | Arg | Gln | Met | Phe | Phe | Val | Ile | Ser | Leu | Asp | Pro | Pro |  |  |
|  |  |  | 250 |  |  |  |  | 255 |  |  |  |  | 260 |  |  |  |  |
| ATC | AAG | CAA | GGC | CAA | ACT | CGC | TAC | CAC | TTC | CTG | ATC | CTC | CTC | TTC | TCC |  | 1108 |
| Ile | Lys | Gln | Gly | Gln | Thr | Arg | Tyr | His | Phe | Leu | Ile | Leu | Leu | Phe | Ser |  |  |
|  |  | 265 |  |  |  |  | 270 |  |  |  |  | 275 |  |  |  |  |  |
| AAG | GAC | GAG | GAC | ATT | TCG | TTG | ACT | CTG | AAC | ATG | AAC | GAG | GAA | GAA | GTG |  | 1156 |
| Lys | Asp | Glu | Asp | Ile | Ser | Leu | Thr | Leu | Asn | Met | Asn | Glu | Glu | Glu | Val |  |  |
|  | 280 |  |  |  |  | 285 |  |  |  |  | 290 |  |  |  |  |  |  |
| GAG | AAG | CGC | TTT | GAG | GGT | CGG | CTC | ACC | AAG | AAC | ATG | TCA | GGA | TCC | CTC |  | 1204 |
| Glu | Lys | Arg | Phe | Glu | Gly | Arg | Leu | Thr | Lys | Asn | Met | Ser | Gly | Ser | Leu |  |  |
| 295 |  |  |  |  | 300 |  |  |  |  | 305 |  |  |  |  | 310 |  |  |
| TAT | GAG | ATG | GTC | AGC | CGG | GTC | ATG | AAA | GCA | CTG | GTA | AAC | CGC | AAG | ATC |  | 1252 |
| Tyr | Glu | Met | Val | Ser | Arg | Val | Met | Lys | Ala | Leu | Val | Asn | Arg | Lys | Ile |  |  |
|  |  |  |  | 315 |  |  |  |  | 320 |  |  |  |  | 325 |  |  |  |
| ACA | GTG | CCA | GGC | AAC | TTC | CAA | GGG | CAC | TCA | GGG | GCC | CAG | TGC | ATT | ACC |  | 1300 |
| Thr | Val | Pro | Gly | Asn | Phe | Gln | Gly | His | Ser | Gly | Ala | Gln | Cys | Ile | Thr |  |  |
|  |  |  | 330 |  |  |  |  | 335 |  |  |  |  | 340 |  |  |  |  |
| TGT | TCC | TAC | AAG | GCA | AGC | TCA | GGA | CTG | CTC | TAC | CCG | CTG | GAG | CGG | GGC |  | 1348 |
| Cys | Ser | Tyr | Lys | Ala | Ser | Ser | Gly | Leu | Leu | Tyr | Pro | Leu | Glu | Arg | Gly |  |  |
|  |  | 345 |  |  |  |  | 350 |  |  |  |  | 355 |  |  |  |  |  |
| TTC | ATC | TAC | GTC | CAC | AAG | CCA | CCT | GTG | CAC | ATC | CGC | TTC | GAT | GAG | ATC |  | 1396 |
| Phe | Ile | Tyr | Val | His | Lys | Pro | Pro | Val | His | Ile | Arg | Phe | Asp | Glu | Ile |  |  |
|  | 360 |  |  |  |  | 365 |  |  |  |  | 370 |  |  |  |  |  |  |
| TCC | TTT | GTC | AAC | TTT | GCT | CGT | GGT | ACC | ACT | ACT | ACT | CGT | TCC | TTT | GAC |  | 1444 |
| Ser | Phe | Val | Asn | Phe | Ala | Arg | Gly | Thr | Thr | Thr | Thr | Arg | Ser | Phe | Asp |  |  |
| 375 |  |  |  |  | 380 |  |  |  |  | 385 |  |  |  |  | 390 |  |  |
| TTT | GAA | ATT | GAG | ACC | AAG | CAG | GGC | ACT | CAG | TAT | ACC | TTC | AGC | AGC | ATT |  | 1492 |
| Phe | Glu | Ile | Glu | Thr | Lys | Gln | Gly | Thr | Gln | Tyr | Thr | Phe | Ser | Ser | Ile |  |  |
|  |  |  |  | 395 |  |  |  |  | 400 |  |  |  |  | 405 |  |  |  |
| GAG | AGG | GAG | GAG | TAC | GGG | AAA | CTG | TTT | GAT | TTT | GTC | AAC | GCG | AAA | AAG |  | 1540 |
| Glu | Arg | Glu | Glu | Tyr | Gly | Lys | Leu | Phe | Asp | Phe | Val | Asn | Ala | Lys | Lys |  |  |
|  |  |  | 410 |  |  |  |  | 415 |  |  |  |  | 420 |  |  |  |  |
| CTC | AAC | ATC | AAA | AAC | CGA | GGA | TTG | AAA | GAG | GGC | ATG | AAC | CCA | AGC | TAC |  | 1588 |
| Leu | Asn | Ile | Lys | Asn | Arg | Gly | Leu | Lys | Glu | Gly | Met | Asn | Pro | Ser | Tyr |  |  |
|  |  | 425 |  |  |  |  | 430 |  |  |  |  | 435 |  |  |  |  |  |
| GAT | GAA | TAT | GCT | GAC | TCT | GAT | GAG | GAC | CAG | CAT | GAT | GCC | TAC | TTG | GAG |  | 1636 |
| Asp | Glu | Tyr | Ala | Asp | Ser | Asp | Glu | Asp | Gln | His | Asp | Ala | Tyr | Leu | Glu |  |  |
|  | 440 |  |  |  |  | 445 |  |  |  |  | 450 |  |  |  |  |  |  |
| AGG | ATG | AAG | GAG | GAA | GGC | AAG | ATC | CGG | GAG | GAG | AAT | GCC | AAT | GAC | AGC |  | 1684 |
| Arg | Met | Lys | Glu | Glu | Gly | Lys | Ile | Arg | Glu | Glu | Asn | Ala | Asn | Asp | Ser |  |  |
| 455 |  |  |  |  | 460 |  |  |  |  | 465 |  |  |  |  | 470 |  |  |
| AGC | GAT | GAC | TCA | GGA | GAA | GAA | ACC | GAT | GAG | TCA | TTC | AAC | CCA | GGT | GAA |  | 1732 |
| Ser | Asp | Asp | Ser | Gly | Glu | Glu | Thr | Asp | Glu | Ser | Phe | Asn | Pro | Gly | Glu |  |  |
|  |  |  |  | 475 |  |  |  |  | 480 |  |  |  |  | 485 |  |  |  |
| GAG | GAG | GAA | GAT | GTG | GCA | GAG | GAG | TTT | GAC | AGC | AAC | GCC | TCT | GCC | AGC |  | 1780 |
| Glu | Glu | Glu | Asp | Val | Ala | Glu | Glu | Phe | Asp | Ser | Asn | Ala | Ser | Ala | Ser |  |  |
|  |  |  | 490 |  |  |  |  | 495 |  |  |  |  | 500 |  |  |  |  |
| TCC | TCC | AGT | AAT | GAG | GGT | GAC | AGT | GAC | CGG | GAT | GAG | AAG | AAG | CGG | AAA |  | 1828 |
| Ser | Ser | Ser | Asn | Glu | Gly | Asp | Ser | Asp | Arg | Asp | Glu | Lys | Lys | Arg | Lys |  |  |
|  |  | 505 |  |  |  |  | 510 |  |  |  |  | 515 |  |  |  |  |  |
| CAG | CTC | AAA | AAG | GCC | AAG | ATG | GCC | AAG | GAC | CGC | AAG | AGC | CGC | AAG | AAG |  | 1876 |
| Gln | Leu | Lys | Lys | Ala | Lys | Met | Ala | Lys | Asp | Arg | Lys | Ser | Arg | Lys | Lys |  |  |
|  | 520 |  |  |  |  | 525 |  |  |  |  | 530 |  |  |  |  |  |  |

| | | | | | | | | | | | | | | | | |
|---|---|---|---|---|---|---|---|---|---|---|---|---|---|---|---|---|
| CCT | GTG | GAG | GTG | AAG | AAG | GGC | AAA | GAC | CCC | AAT | GCC | CCC | AAG | AGG | CCC | 1924 |
| Pro 535 | Val | Glu | Val | Lys | Lys 540 | Gly | Lys | Asp | Pro | Asn 545 | Ala | Pro | Lys | Arg | Pro 550 | |
| ATG | TCT | GCA | TAC | ATG | CTG | TGG | CTC | AAT | GCC | AGC | CGA | GAG | AAG | ATC | AAG | 1972 |
| Met | Ser | Ala | Tyr | Met 555 | Leu | Trp | Leu | Asn | Ala 560 | Ser | Arg | Glu | Lys | Ile 565 | Lys | |
| TCA | GAC | CAT | CCT | GGC | ATC | AGC | ATC | ACG | GAT | CTT | TCC | AAG | AAG | GCA | GGC | 2020 |
| Ser | Asp | His | Pro 570 | Gly | Ile | Ser | Ile | Thr 575 | Asp | Leu | Ser | Lys | Lys 580 | Ala | Gly | |
| GAG | ATC | TGG | AAG | GGA | ATG | TCC | AAA | GAG | AAG | AAA | GAG | GAG | TGG | GAT | CGC | 2068 |
| Glu | Ile | Trp 585 | Lys | Gly | Met | Ser | Lys 590 | Glu | Lys | Lys | Glu | Glu 595 | Trp | Asp | Arg | |
| AAG | GCT | GAG | GAT | GCC | AGG | AGG | GAC | TAT | GAA | AAA | GCC | ATG | AAA | GAA | TAT | 2116 |
| Lys | Ala 600 | Glu | Asp | Ala | Arg | Arg 605 | Asp | Tyr | Glu | Lys | Ala 610 | Met | Lys | Glu | Tyr | |
| GAA | GGG | GGC | CGA | GGC | GAG | TCT | TCT | AAG | AGG | GAC | AAG | TCA | AAG | AAG | AAG | 2164 |
| Glu 615 | Gly | Gly | Arg | Gly | Glu 620 | Ser | Ser | Lys | Arg | Asp 625 | Lys | Ser | Lys | Lys | Lys 630 | |
| AAG | AAA | GTA | AAG | GTA | AAG | ATG | GAA | AAG | AAA | TCC | ACG | CCC | TCT | AGG | GGC | 2212 |
| Lys | Lys | Val | Lys | Val 635 | Lys | Met | Glu | Lys | Lys 640 | Ser | Thr | Pro | Ser | Arg 645 | Gly | |
| TCA | TCA | TCC | AAG | TCG | TCC | TCA | AGG | CAG | CTA | AGC | GAG | AGC | TTC | AAG | AGC | 2260 |
| Ser | Ser | Ser | Lys 650 | Ser | Ser | Ser | Arg | Gln 655 | Leu | Ser | Glu | Ser | Phe 660 | Lys | Ser | |
| AAA | GAG | TTT | GTG | TCT | AGT | GAT | GAG | AGC | TCT | TCG | GGA | GAG | AAC | AAG | AGC | 2308 |
| Lys | Glu | Phe 665 | Val | Ser | Ser | Asp | Glu | Ser 670 | Ser | Ser | Gly | Glu | Asn 675 | Lys | Ser | |
| AAA | AAG | AAG | AGG | AGG | AGG | AGC | GAG | GAC | TCT | GAA | GAA | GAA | GAA | CTA | GCC | 2356 |
| Lys | Lys 680 | Lys | Arg | Arg | Arg | Ser | Glu | Asp 685 | Ser | Glu | Glu | Glu 690 | Glu | Leu | Ala | |
| AGT | ACT | CCC | CCC | AGC | TCA | GAG | GAC | TCA | GCG | TCA | GGA | TCC | GAT | GAG | TAGAAACG | 2411 |
| Ser 695 | Thr | Pro | Pro | Ser 700 | Ser | Glu | Asp | Ser | Ala 705 | Ser | Gly | Ser | Asp | Glu 710 | | |

```
GGAAGGTTCT CTTTGCGCTT GCCTTCTCAC ACCCCCCGAC TCCCCACCCA TATTTTGGTA    2471
CCAGTTTCTC CTCATGAAAT GCAGTCCCTG GATTCTGTGC CATCTGAACA TGCTCTCCTG    2531
TTGGTGTGTA TGTCACTAGG GCAGTGGGGA GACGTCTTAA CTCTGCTGCT TCCCAAGGAT    2591
GGCTGTTTAT AATTTGGGGA GAGATAGGGT GGGAGGCAGG GCAATGCAGG ATCCAAATCC    2651
TCATCTTACT TTCCCGACCT TAAGGATGTA GCTGCTGCTT GTCCTGTTCA AGTTGCTGGA    2711
GCAGGGGTCA TGTGAGGCCA GGCCTGTAGC TCCTACCTGG GGCCTATTTC TACTTTCATT    2771
TTGTATTTCT GGTCTGTGAA AATGATTTAA TAAAGGGAAC TGACTTTGGA AACCAAAAAA    2831
AGGAATTC                                                              2839
```

(2) INFORMATION FOR SEQ ID NO:7:

(i) SEQUENCE CHARACTERISTICS:
        (A) LENGTH: 709 amino acids
        (B) TYPE: amino acid
        (D) TOPOLOGY: linear (ii) MOLECULE TYPE: protein (vi) ORIGINAL SOURCE:
        (A) ORGANISM: Homo sapiens (vii) IMMEDIATE SOURCE:
        (B) CLONE: human SSRP (predicted)

(ix) FEATURE:
        (A) NAME/KEY: Domain
        (B) LOCATION: 440..496
        (D) OTHER INFORMATION: /label=Acidic (ix) FEATURE:

(A) NAME/KEY: Domain
(B) LOCATION: 512..534
(D) OTHER INFORMATION: /label=Basic I (ix) FEATURE:
(A) NAME/KEY: Domain
(B) LOCATION: 539..614
(D) OTHER INFORMATION: /label=HMG-box (ix) FEATURE:
(A) NAME/KEY: Domain
(B) LOCATION: 623..640
(D) OTHER INFORMATION: /label=Basic II (ix) FEATURE:
(A) NAME/KEY: Domain
(B) LOCATION: 661..709
(D) OTHER INFORMATION: /label=Mixed Charge (xi) SEQUENCE DESCRIPTION: SEQ ID NO:7:

```
Met Ala Glu Thr Leu Glu Phe Asn Asp Val Tyr Gln Glu Val Lys Gly
  1               5                  10                  15

Ser Met Asn Asp Gly Arg Leu Arg Leu Ser Arg Gln Gly Ile Ile Phe
             20                  25                  30

Lys Asn Ser Lys Thr Gly Lys Val Asp Asn Ile Gln Ala Gly Glu Leu
         35                  40                  45

Thr Glu Gly Ile Trp Arg Arg Val Ala Leu Gly His Gly Leu Lys Leu
     50                  55                  60

Leu Thr Lys Asn Gly His Val Tyr Lys Tyr Asp Gly Phe Arg Glu Ser
 65                  70                  75                  80

Glu Phe Glu Lys Leu Ser Asp Phe Phe Lys Thr His Tyr Arg Leu Glu
                 85                  90                  95

Leu Met Glu Lys Asp Leu Cys Val Lys Gly Trp Asn Trp Gly Thr Val
             100                 105                 110

Lys Phe Gly Gly Gln Leu Leu Ser Phe Asp Ile Gly Asp Gln Pro Val
         115                 120                 125

Phe Glu Ile Pro Leu Ser Asn Val Ser Gln Cys Thr Thr Gly Lys Asn
 130                 135                 140

Glu Val Thr Leu Glu Phe His Gln Asn Asp Asp Ala Glu Val Ser Leu
145                 150                 155                 160

Met Glu Val Arg Phe Tyr Val Pro Pro Thr Gln Glu Asp Gly Val Asp
             165                 170                 175

Pro Val Glu Ala Phe Ala Gln Asn Val Leu Ser Lys Ala Asp Val Ile
         180                 185                 190

Gln Ala Thr Gly Asp Ala Ile Cys Ile Phe Arg Glu Leu Gln Cys Leu
     195                 200                 205

Thr Pro Arg Gly Arg Tyr Asp Ile Arg Ile Tyr Pro Thr Phe Leu His
 210                 215                 220

Leu His Gly Lys Thr Phe Asp Tyr Lys Ile Pro Tyr Thr Thr Val Leu
225                 230                 235                 240

Arg Leu Phe Leu Leu Pro His Lys Asp Gln Arg Gln Met Phe Phe Val
             245                 250                 255

Ile Ser Leu Asp Pro Pro Ile Lys Gln Gly Gln Thr Arg Tyr His Phe
         260                 265                 270

Leu Ile Leu Leu Phe Ser Lys Asp Glu Asp Ile Ser Leu Thr Leu Asn
     275                 280                 285

Met Asn Glu Glu Glu Val Glu Lys Arg Phe Glu Gly Arg Leu Thr Lys
 290                 295                 300

Asn Met Ser Gly Ser Leu Tyr Glu Met Val Ser Arg Val Met Lys Ala
305                 310                 315                 320

Leu Val Asn Arg Lys Ile Thr Val Pro Gly Asn Phe Gln Gly His Ser
```

```
                              325                          330                          335
        Gly  Ala  Gln  Cys  Ile  Thr  Cys  Ser  Tyr  Lys  Ala  Ser  Ser  Gly  Leu  Leu
                       340                       345                      350

Tyr  Pro  Leu  Glu  Arg  Gly  Phe  Ile  Tyr  Val  His  Lys  Pro  Pro  Val  His
                       355                       360                      365

Ile  Arg  Phe  Asp  Glu  Ile  Ser  Phe  Val  Asn  Phe  Ala  Arg  Gly  Thr  Thr
                       370                       375                      380

Thr  Thr  Arg  Ser  Phe  Asp  Phe  Glu  Ile  Glu  Thr  Lys  Gln  Gly  Thr  Gln
        385                       390                       395                      400

Tyr  Thr  Phe  Ser  Ser  Ile  Glu  Arg  Glu  Glu  Tyr  Gly  Lys  Leu  Phe  Asp
                            405                      410                      415

Phe  Val  Asn  Ala  Lys  Lys  Leu  Asn  Ile  Lys  Asn  Arg  Gly  Leu  Lys  Glu
                            420                      425                      430

Gly  Met  Asn  Pro  Ser  Tyr  Asp  Glu  Tyr  Ala  Asp  Ser  Asp  Glu  Asp  Gln
                       435                      440                       445

His  Asp  Ala  Tyr  Leu  Glu  Arg  Met  Lys  Glu  Glu  Gly  Lys  Ile  Arg  Glu
                       450                      455                       460

Glu  Asn  Ala  Asn  Asp  Ser  Ser  Asp  Asp  Ser  Gly  Glu  Glu  Thr  Asp  Glu
        465                      470                       475                      480

Ser  Phe  Asn  Pro  Gly  Glu  Glu  Glu  Glu  Asp  Val  Ala  Glu  Glu  Phe  Asp
                            485                      490                      495

Ser  Asn  Ala  Ser  Ala  Ser  Ser  Ser  Asn  Glu  Gly  Asp  Ser  Asp  Arg
                       500                      505                       510

Asp  Glu  Lys  Lys  Arg  Lys  Gln  Leu  Lys  Lys  Ala  Lys  Met  Ala  Lys  Asp
                       515                      520                       525

Arg  Lys  Ser  Arg  Lys  Lys  Pro  Val  Glu  Val  Lys  Lys  Gly  Lys  Asp  Pro
                       530                      535                       540

Asn  Ala  Pro  Lys  Arg  Pro  Met  Ser  Ala  Tyr  Met  Leu  Trp  Leu  Asn  Ala
        545                      550                       555                      560

Ser  Arg  Glu  Lys  Ile  Lys  Ser  Asp  His  Pro  Gly  Ile  Ser  Ile  Thr  Asp
                            565                      570                      575

Leu  Ser  Lys  Lys  Ala  Gly  Glu  Ile  Trp  Lys  Gly  Met  Ser  Lys  Glu  Lys
                       580                      585                       590

Lys  Glu  Glu  Trp  Asp  Arg  Lys  Ala  Glu  Asp  Ala  Arg  Arg  Asp  Tyr  Glu
                       595                      600                       605

Lys  Ala  Met  Lys  Glu  Tyr  Glu  Gly  Gly  Arg  Gly  Glu  Ser  Ser  Lys  Arg
                 610                      615                       620

Asp  Lys  Ser  Lys  Lys  Lys  Lys  Val  Lys  Val  Lys  Met  Glu  Lys  Lys
        625                      630                       635                      640

Ser  Thr  Pro  Ser  Arg  Gly  Ser  Ser  Lys  Ser  Ser  Arg  Gln  Leu
                            645                      650                      655

Ser  Glu  Ser  Phe  Lys  Ser  Lys  Glu  Phe  Val  Ser  Ser  Asp  Glu  Ser  Ser
                       660                      665                       670

Ser  Gly  Glu  Asn  Lys  Ser  Lys  Lys  Lys  Arg  Arg  Arg  Ser  Glu  Asp  Ser
                       675                      680                       685

Glu  Glu  Glu  Glu  Leu  Ala  Ser  Thr  Pro  Pro  Ser  Ser  Glu  Asp  Ser  Ala
                 690                      695                       700

Ser  Gly  Ser  Asp  Glu
        705
```

(2) INFORMATION FOR SEQ ID NO:8:

( i ) SEQUENCE CHARACTERISTICS:
        ( A ) LENGTH: 1898 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
    ( A ) ORGANISM: Homo sapiens ( v i i ) IMMEDIATE SOURCE:
    ( A ) LIBRARY: Human B cell
    ( B ) CLONE: lambda-Pt1

( x i ) SEQUENCE DESCRIPTION: SEQ ID NO:8:

| | | | | | | |
|---|---|---|---|---|---|---|
| GAATTCCACC | AAAACGATGA | CGCAGAGGTG | TCTCTCATGG | AGGTGCGCTT | CTACGTCCCA | 60 |
| CCCACCCAGG | AGGATGGTGT | GGACCCTGTT | GAGGCCTTTG | CCCAGAATGT | GTTGTCAAAG | 120 |
| GCGGATGTAA | TCCAGGCCAC | GGGAGATGCC | ATCTGCATCT | TCCGGGAGCT | GCAGTGTCTG | 180 |
| ACTCCTCGTG | GTCGTTATGA | CATTCGGATC | TACCCCACCT | TTCTGCACCT | GCATGGCAAG | 240 |
| ACCTTTGACT | ACAAGATCCC | CTACACCACA | GTACTGCGTC | TGTTTTTGTT | ACCCCACAAG | 300 |
| GACCAGCGCC | AGATGTTCTT | TGTGATCAGC | CTGGATCCCC | CAATCAAGCA | AGGCCAAACT | 360 |
| CGCTACCACT | TCCTGATCCT | CCTCTTCTCC | AAGGACGAGG | ACATTTCGTT | GACTCTGAAC | 420 |
| ATGAACGAGG | AAGAAGTGGA | GAAGCGCTTT | GAGGGTCGGC | TCACCAAGAA | CATGTCAGGA | 480 |
| TCCCTCTATG | AGATGGTCAG | CCGGGTCATG | AAAGCACTGG | TAAACCGCAA | GATCACAGTG | 540 |
| CCAGGCAACT | TCCAAGGGCA | CTCAGGGCC | CAGTGCATTA | CCTGTTCCTA | CAAGGCAAGC | 600 |
| TCAGGACTGC | TCTACCCGCT | GGAGCGGGGC | TTCATCTACG | TCCACAAGCC | ACCTGTGCAC | 660 |
| ATCCGCTTCG | ATGAGATCTC | CTTTGTCAAC | TTTGCTCGTG | GTACCACTAC | TACTCGTTCC | 720 |
| TTTGACTTTG | AAATTGAGAC | CAAGCAGGGC | ACTCAGTATA | CCTTCAGCAG | CATTGAGAGG | 780 |
| GAGGAGTACG | GGAAACTGTT | TGATTTGTC | AACGCGAAAA | AGCTCAACAT | CAAAAACCGA | 840 |
| GGATTGAAAG | AGGGCATGAA | CCCAAGCTAC | GATGAATATG | CTGACTCTGA | TGAGGACCAG | 900 |
| CATGATGCCT | ACTTGGAGAG | GATGAAGGAG | GAAGGCAAGA | TCCGGGAGGA | GAATGCCAAT | 960 |
| GACAGCAGCG | ATGACTCAGG | AGAAGAAACC | GATGAGTCAT | TCAACCCAGG | TGAAGAGGAG | 1020 |
| GAAGATGTGG | CAGAGGAGTT | TGACAGCAAC | GCCTCTGCCA | GCTCCTCCAG | TAATGAGGGT | 1080 |
| GACAGTGACC | GGGATGAGAA | GAAGCGGAAA | CAGCTCAAAA | AGGCCAAGAT | GGCCAAGGAC | 1140 |
| CGCAAGAGCC | GCAAGAAGCC | TGTGGAGGTG | AAGAAGGGCA | AAGACCCCAA | TGCCCCCAAG | 1200 |
| AGGCCCATGT | CTGCATACAT | GCTGTGGCTC | AATGCCAGCC | GAGAGAAGAT | CAAGTCAGAC | 1260 |
| CATCCTGGCA | TCAGCATCAC | GGATCTTTCC | AAGAAGGCAG | GCGAGATCTG | GAAGGGAATG | 1320 |
| TCCAAAGAGA | AGAAAGAGGA | GTGGGATCGC | AAGGCTGAGG | ATGCCAGGAG | GGACTATGAA | 1380 |
| AAAGCCATGA | AAGAATATGA | AGGGGGCCGA | GGCGAGTCTT | CTAAGAGGGA | CAAGTCAAAG | 1440 |
| AAGAAGAAGA | AAGTAAAGGT | AAAGATGGAA | AAGAAATCCA | CGCCCTCTAG | GGGCTCATCA | 1500 |
| TCCAAGTCGT | CCTCAAGGCA | GCTAAGCGAG | AGCTTCAAGA | GCAAAGAGTT | TGTGTCTAGT | 1560 |
| GATGAGAGCT | CTTCGGGAGA | GAACAAGAGC | AAAAAGAAGA | GGAGGAGGAG | CGAGGACTCT | 1620 |
| GAAGAAGAAG | AACTAGCCAG | TACTCCCCCC | AGCTCAGAGG | ACTCAGCGTC | AGGATCCGAT | 1680 |
| GAGTAGAAAC | GGAGGAAGGT | TCTCTTTGCG | CTTGCCTTCT | CACACCCCC | GACTCCCCAC | 1740 |
| CCATATTTTG | GTACCAGTTT | CTCCTCATGA | AATGCAGTCC | CTGGATTCTG | TGCCATCTGA | 1800 |
| ACATGCTCTC | CTGTTGGTGT | GTATGTCACT | AGGGCAGTGG | GGAGACGTCT | TAACTCTGCT | 1860 |
| GCTTCCCAAG | GATGGCTGTT | TATAATTTGG | GGAGAGAT | | | 1898 |

( 2 ) INFORMATION FOR SEQ ID NO:9:

( i ) SEQUENCE CHARACTERISTICS:
        ( A ) LENGTH: 1444 base pairs
        ( B ) TYPE: nucleic acid (C) STRANDEDNESS: double
(D) TOPOLOGY: linear (ii) MOLECULE TYPE: cDNA (vi) ORIGINAL SOURCE:
 (A) ORGANISM: Homo sapiens (vii) IMMEDIATE SOURCE:
 (A) LIBRARY: Human B cell
 (B) CLONE: lambda Pt2

(xi) SEQUENCE DESCRIPTION: SEQ ID NO:9:

| | | | | | | |
|---|---|---|---|---|---|---|
| GAATTCCACC | AAAACGATGA | CGCAGAGGTG | TCTCTCATGG | AGGTGCGCTT | CTACGTCCCA | 60 |
| CCCACCCAGG | AGGATGGTGT | GGACCCTGTT | GAGGCCTTTG | CCCAGAATGT | GTTGTCAAAG | 120 |
| GCGGATGTAA | TCCAGGCCAC | GGGAGATGCC | ATCTGCATCT | TCCGGGAGCT | GCAGTGTCTG | 180 |
| ACTCCTCGTG | GTCGTTATGA | CATTCGGATC | TACCCCACCT | TTCTGCACCT | GCATGGCAAG | 240 |
| ACCTTTGACT | ACAAGATCCC | CTACACCACA | GTACTGCGTC | TGTTTTTGTT | ACCCCACAAG | 300 |
| GACCAGCGCC | AGATGTTCTT | TGTGATCAGC | CTGGATCCCC | CAATCAAGCA | AGGCCAAACT | 360 |
| CGCTACCACT | TCCTGATCCT | CCTCTTCTCC | AAGGACGAGG | ACATTTCGTT | GACTCTGAAC | 420 |
| ATGAACGAGG | AAGAAGTGGA | GAAGCGCTTT | GAGGGTCGGC | TCACCAAGAA | CATGTCAGGA | 480 |
| TCCCTCTATG | AGATGGTCAG | CCGGGTCATG | AAAGCACTGG | TAAACCGCAA | GATCACAGTG | 540 |
| CCAGGCAACT | TCCAAGGGCA | CTCAGGGGCC | CAGTGCATTA | CCTGTTCCTA | CAAGGCAAGC | 600 |
| TCAGGACTGC | TCTACCCGCT | GGAGCGGGGC | TTCATCTACG | TCCACAAGCC | ACCTGTGCAC | 660 |
| ATCCGCTTCG | ATGAGATCTC | CTTTGTCAAC | TTTGCTCGTG | GTACCACTAC | TACTCGTTCC | 720 |
| TTTGACTTTG | AAATTGAGAC | CAAGCAGGGC | ACTCAGTATA | CCTTCAGCAG | CATTGAGAGG | 780 |
| GAGGAGTACG | GGAAACTGTT | TGATTTTGTC | AACGCGAAAA | AGCTCAACAT | CAAAAACCGA | 840 |
| GGATTGAAAG | AGGGCATGAA | CCCAAGCTAC | GATGAATATG | CTGACTCTGA | TGAGGACCAG | 900 |
| CATGATGCCT | ACTTGGAGAG | GATGAAGGAG | GAAGGCAAGA | TCCGGGAGGA | GAATGCCAAT | 960 |
| GACAGCAGCG | ATGACTCAGG | AGAAGAAACC | GATGAGTCAT | TCAACCCAGG | TGAAGAGGAG | 1020 |
| GAAGATGTGG | CAGAGGAGTT | TGACAGCAAC | GCCTCTGCCA | GCTCCTCCAG | TAATGAGGGT | 1080 |
| GACAGTGACC | GGGATGAGAA | GAAGCGGAAA | CAGCTCAAAA | AGGCCAAGAT | GGCCAAGGAC | 1140 |
| CGCAAGAGCC | GCAAGAAGCC | TGTGGAGGTG | AAGAAGGGCA | AGACCCCAA | TGCCCCCAAG | 1200 |
| AGGCCCATGT | CTGCATACAT | GCTGTGGCTC | AATGCCAGCC | GAGAGAAGAT | CAAGTCAGAC | 1260 |
| CATCCTGGCA | TCAGCATCAC | GGATCTTTCC | AAGAAGGCAG | GCGAGATCTG | GAAGGGAATG | 1320 |
| TCCAAAGAGA | AGAAAGAGGA | GTGGGATCGC | AAGGCTGAGG | ATGCCAGGAG | GGACTATGAA | 1380 |
| AAAGCCATGA | AAGAATATGA | AGGGGGCCGA | GGCGAGTCTT | CTAAGAGGGA | CAAGTCAAAG | 1440 |
| AAGA | | | | | | 1444 |

(2) INFORMATION FOR SEQ ID NO:10:

(i) SEQUENCE CHARACTERISTICS:
  (A) LENGTH: 2384 base pairs
  (B) TYPE: nucleic acid
  (C) STRANDEDNESS: double
  (D) TOPOLOGY: linear (ii) MOLECULE TYPE: cDNA (vi) ORIGINAL SOURCE:
  (A) ORGANISM: Drosophila melanogaster (vii) IMMEDIATE SOURCE:
  (B) CLONE: Drosophila SSRP - composite sequence (viii) POSITION IN GENOME:

(A) CHROMOSOME/SEGMENT: 2
(B) MAP POSITION: 60A 1-4

(ix) FEATURE:
(A) NAME/KEY: CDS
(B) LOCATION: 123..2291

(xi) SEQUENCE DESCRIPTION: SEQ ID NO:10:

```
GAATTCCGCG CGCAGTGTTG TTTTGTGTCT GCCGGAATTA TTGTAAATTG GTGACAATTT         60

CGCAAGGCGG CGTAATACAT AGTTGATCTA TTATCTTGTT ACTGGAGAGG AAGAAGTGCA        120

GG ATG ACA GAC TCT CTG GAG TAC AAC GAC ATA AAC GCC GAA GTG CGC          167
   Met Thr Asp Ser Leu Glu Tyr Asn Asp Ile Asn Ala Glu Val Arg
   1               5                   10                  15

GGA GTC TTG TGT TCC GGA CGC CTA AAG ATG ACC GAG CAG AAC ATC ATC         215
Gly Val Leu Cys Ser Gly Arg Leu Lys Met Thr Glu Gln Asn Ile Ile
            20                  25                  30

TTC AAG AAC ACC AAG ACC GGC AAG GTG GAG CAG ATC TCG GCA GAG GAC         263
Phe Lys Asn Thr Lys Thr Gly Lys Val Glu Gln Ile Ser Ala Glu Asp
                35                  40                  45

ATA GAC CTG ATC AAT TCG CAG AAG TTC GTG GGC ACC TGG GGA CTG AGG         311
Ile Asp Leu Ile Asn Ser Gln Lys Phe Val Gly Thr Trp Gly Leu Arg
        50                  55                  60

GTG TTC ACC AAA GGC GGC GTG CTC CAC CGC TTC ACC GGA TTC CGC GAC         359
Val Phe Thr Lys Gly Gly Val Leu His Arg Phe Thr Gly Phe Arg Asp
    65                  70                  75

AGC GAG CAC GAG AAG CTG GGC AAG TTT ATC AAG GCT GCC TAC TCG CAG         407
Ser Glu His Glu Lys Leu Gly Lys Phe Ile Lys Ala Ala Tyr Ser Gln
80                  85                  90                      95

GAG ATG GTC GAG AAG GAG ATG TGC GTC AAG GGC TGG AAC TGG GGC ACC         455
Glu Met Val Glu Lys Glu Met Cys Val Lys Gly Trp Asn Trp Gly Thr
                100                 105                 110

GCC CGC TTC ATG GGC TCC GTC CTG AGC TTC GAC AAG GAG TCG AAG ACC         503
Ala Arg Phe Met Gly Ser Val Leu Ser Phe Asp Lys Glu Ser Lys Thr
            115                 120                 125

ATC TTC GAG GTG CCG CTG TCG CAC GTT TCG CAG TGC GTG ACC GGC AAG         551
Ile Phe Glu Val Pro Leu Ser His Val Ser Gln Cys Val Thr Gly Lys
        130                 135                 140

AAC GAG GTC ACC CTG GAG TTC CAC CAA AAC GAC GAT GCG CCC GTG GGT         599
Asn Glu Val Thr Leu Glu Phe His Gln Asn Asp Asp Ala Pro Val Gly
    145                 150                 155

CTA CTG GAG ATG CGG TTC CAC ATA CCC GCC GTG GAG TCG GCC GAG GAG         647
Leu Leu Glu Met Arg Phe His Ile Pro Ala Val Glu Ser Ala Glu Glu
160                 165                 170                     175

GAT CCG GTA GAC AAG TTC CAC CAG AAC GTA ATG AGC AAG GCC TCG GTC         695
Asp Pro Val Asp Lys Phe His Gln Asn Val Met Ser Lys Ala Ser Val
                180                 185                 190

ATC TCG GCT TCG GGC GAG TCC ATC GCC ATT TTC AGA GAG ATC CAG ATC         743
Ile Ser Ala Ser Gly Glu Ser Ile Ala Ile Phe Arg Glu Ile Gln Ile
            195                 200                 205

CTC ACG CCT CGC GGT CGC TAT GAC ATC AAG ATC TTC TCG ACC TTC TTC         791
Leu Thr Pro Arg Gly Arg Tyr Asp Ile Lys Ile Phe Ser Thr Phe Phe
        210                 215                 220

CAG CTG CAC GGC AAG ACG TTC GAC TAC AAG ATT CCC ATG GAC TCG GTG         839
Gln Leu His Gly Lys Thr Phe Asp Tyr Lys Ile Pro Met Asp Ser Val
    225                 230                 235

CTG CGG CTC TTC ATG CTG CCC CAC AAA GAC AGT CGA CAG ATG TTC TTT         887
Leu Arg Leu Phe Met Leu Pro His Lys Asp Ser Arg Gln Met Phe Phe
240                 245                 250                     255

GTG CTC TCC TTG GAT CCG CCC ATC AAG CAG GGA CAA ACG CGT TAC CAC         935
Val Leu Ser Leu Asp Pro Pro Ile Lys Gln Gly Gln Thr Arg Tyr His
                260                 265                 270
```

| | | | | | | | | | | | | | | | | |
|---|---|---|---|---|---|---|---|---|---|---|---|---|---|---|---|---|
| TAC | CTG | GTC | CTG | CTG | TTT | GCT | CCC | GAT | GAG | GAG | ACC | ACC | ATT | GAG | CTG | 983 |
| Tyr | Leu | Val | Leu 275 | Leu | Phe | Ala | Pro | Asp 280 | Glu | Glu | Thr | Thr | Ile 285 | Glu | Leu | |
| CCA | TTC | TCG | GAA | GCC | GAG | TTG | CGA | GAC | AAG | TAC | GAG | GGC | AAG | CTG | GAG | 1031 |
| Pro | Phe | Ser 290 | Glu | Ala | Glu | Leu | Arg 295 | Asp | Lys | Tyr | Glu | Gly 300 | Lys | Leu | Glu | |
| AAA | GAG | ATC | TCC | GGG | CCG | GTG | TAC | GAG | GTG | ATG | GGC | AAA | GTG | ATG | AAG | 1079 |
| Lys | Glu 305 | Ile | Ser | Gly | Pro | Val 310 | Tyr | Glu | Val | Met | Gly 315 | Lys | Val | Met | Lys | |
| GTG | CTG | ATC | GGT | CGA | AAA | ATT | ACC | GGA | CCC | GGT | AAC | TTT | ATC | GGA | CAC | 1127 |
| Val 320 | Leu | Ile | Gly | Arg | Lys 325 | Ile | Thr | Gly | Pro | Gly 330 | Asn | Phe | Ile | Gly | His 335 | |
| TCT | GGC | ACG | GCT | GCA | GTG | GGC | TGC | TCG | TTC | AAG | GCT | GCA | GCT | GGA | TAT | 1175 |
| Ser | Gly | Thr | Ala | Ala 340 | Val | Gly | Cys | Ser | Phe 345 | Lys | Ala | Ala | Ala | Gly 350 | Tyr | |
| CTG | TAT | CCC | CTG | GAG | CGA | GGA | TTC | ATC | TAT | ATC | CAC | AAG | CCA | CCG | CTG | 1223 |
| Leu | Tyr | Pro | Leu 355 | Glu | Arg | Gly | Phe | Ile 360 | Tyr | Ile | His | Lys | Pro 365 | Pro | Leu | |
| CAT | ATC | CGC | TTT | GAG | GAG | ATT | AGT | TCT | GTG | AAC | TTT | GCC | CGC | AGC | GGC | 1271 |
| His | Ile | Arg 370 | Phe | Glu | Glu | Ile | Ser 375 | Ser | Val | Asn | Phe | Ala 380 | Arg | Ser | Gly | |
| GGA | TCC | ACG | CGA | TCT | TTC | GAC | TTC | GAA | GTG | ACG | CTC | AAG | AAC | GGA | ACT | 1319 |
| Gly | Ser | Thr 385 | Arg | Ser | Phe | Asp | Phe 390 | Glu | Val | Thr | Leu | Lys 395 | Asn | Gly | Thr | |
| GTT | CAC | ATC | TTC | TCC | TCC | ATC | GAG | AAG | GAG | GAG | TAT | GCC | AAG | CTC | TTC | 1367 |
| Val 400 | His | Ile | Phe | Ser | Ser 405 | Ile | Glu | Lys | Glu | Glu 410 | Tyr | Ala | Lys | Leu | Phe 415 | |
| GAC | TAC | ATC | ACA | CAG | AAG | AAG | TTG | CAT | GTC | AGC | AAC | ATG | GGC | AAG | GAC | 1415 |
| Asp | Tyr | Ile | Thr | Gln 420 | Lys | Lys | Leu | His | Val 425 | Ser | Asn | Met | Gly | Lys 430 | Asp | |
| AAG | AGC | GGC | TAC | AAG | GAC | GTG | GAC | TTT | GGT | GAT | TCG | GAC | AAC | GAG | AAC | 1463 |
| Lys | Ser | Gly | Tyr 435 | Lys | Asp | Val | Asp | Phe 440 | Gly | Asp | Ser | Asp | Asn 445 | Glu | Asn | |
| GAA | CCA | GAT | GCC | TAT | CTG | GCT | CGC | CTC | AAG | GCT | GAG | GCG | AGG | GAA | AAG | 1511 |
| Glu | Pro | Asp 450 | Ala | Tyr | Leu | Ala | Arg 455 | Leu | Lys | Ala | Glu | Ala 460 | Arg | Glu | Lys | |
| GAG | GAG | GAC | GAC | GAC | GAT | GGC | GAC | TCG | GAT | GAA | GAG | TCC | ACG | GAT | GAG | 1559 |
| Glu | Glu | Asp | Asp 465 | Asp | Asp | Gly | Asp | Ser 470 | Asp | Glu | Glu | Ser | Thr 475 | Asp | Glu | |
| GAC | TTC | AAG | CCC | AAC | GAG | AAC | GAG | TCC | GAT | GTG | GCC | GAG | GAG | TAT | GAC | 1607 |
| Asp 480 | Phe | Lys | Pro | Asn | Glu 485 | Asn | Glu | Ser | Asp | Val 490 | Ala | Glu | Glu | Tyr | Asp 495 | |
| AGC | AAC | GTG | GAG | AGT | GAT | TCG | GAC | GAT | GAC | AGC | GAT | GCT | AGT | GGC | GGC | 1655 |
| Ser | Asn | Val | Glu | Ser 500 | Asp | Ser | Asp | Asp | Asp 505 | Ser | Asp | Ala | Ser | Gly 510 | Gly | |
| GGA | GGC | GAC | AGC | GAC | GGC | GCC | AAG | AAA | AAG | AAG | GAG | AAG | AAG | TCC | GAG | 1703 |
| Gly | Gly | Asp | Ser 515 | Asp | Gly | Ala | Lys | Lys 520 | Lys | Lys | Glu | Lys | Lys 525 | Ser | Glu | |
| AAG | AAA | GAG | AAA | AAG | GAG | AAA | AAA | CAC | AAG | GAG | AAG | GAG | AGA | ACA | AAG | 1751 |
| Lys | Lys | Glu 530 | Lys | Lys | Glu | Lys | Lys 535 | His | Lys | Glu | Lys | Glu 540 | Arg | Thr | Lys | |
| AAA | CCC | TCC | AAG | AAG | AAG | AAG | GAC | TCT | GGC | AAA | CCC | AAG | CGC | GCC | ACC | 1799 |
| Lys | Pro 545 | Ser | Lys | Lys | Lys | Lys 550 | Asp | Ser | Gly | Lys | Pro 555 | Lys | Arg | Ala | Thr | |
| ACC | GCT | TTC | ATG | CTC | TGG | CTG | AAC | GAC | ACG | CGC | GAG | AGC | ATC | AAG | AGG | 1847 |
| Thr 560 | Ala | Phe | Met | Leu | Trp 565 | Leu | Asn | Asp | Thr | Arg 570 | Glu | Ser | Ile | Lys | Arg 575 | |
| GAA | AAT | CCG | GGC | ATA | AAG | GTT | ACC | GAG | ATC | GCC | AAG | AAG | GGC | GGC | GAG | 1895 |
| Glu | Asn | Pro | Gly | Ile 580 | Lys | Val | Thr | Glu | Ile 585 | Ala | Lys | Lys | Gly | Gly 590 | Glu | |
| ATG | TGG | AAG | GAG | CTG | AAG | GAC | AAG | TCC | AAG | TGG | GAG | GAT | GCG | GCG | GCC | 1943 |
| Met | Trp | Lys | Glu | Leu | Lys | Asp | Lys | Ser | Lys | Trp | Glu | Asp | Ala | Ala | Ala | |

| | | | | | | | | | | | | | | | | |
|---|---|---|---|---|---|---|---|---|---|---|---|---|---|---|---|---|
| | | 595 | | | | | 600 | | | | | | 605 | | | |
| AAG | GAC | AAG | CAG | CGC | TAC | CAC | GAC | GAG | ATG | CGC | AAC | TAC | AAG | CCT | GAA | 1991 |
| Lys | Asp | Lys<br>610 | Gln | Arg | Tyr | His | Asp<br>615 | Glu | Met | Arg | Asn | Tyr<br>620 | Lys | Pro | Glu | |
| GCG | GGC | GGT | GAC | AGC | GAC | AAC | GAG | AAG | GGT | GGA | AAG | TCC | TCC | AAG | AAG | 2039 |
| Ala | Gly<br>625 | Gly | Asp | Ser | Asp | Asn<br>630 | Glu | Lys | Gly | Gly | Lys | Ser<br>635 | Ser | Lys | Lys | |
| CGC | AAG | ACG | GAG | CCT | TCT | CCA | TCC | AAG | AAG | GCG | AAT | ACC | TCG | GGC | AGC | 2087 |
| Arg<br>640 | Lys | Thr | Glu | Pro | Ser<br>645 | Pro | Ser | Lys | Lys | Ala<br>650 | Asn | Thr | Ser | Gly | Ser<br>655 | |
| GGC | TTC | AAG | AGC | AAG | GAG | TAC | ATT | TCG | GAC | GAC | GAC | TCC | ACC | AGC | TCC | 2135 |
| Gly | Phe | Lys | Ser | Lys<br>660 | Glu | Tyr | Ile | Ser | Asp<br>665 | Asp | Asp | Ser | Thr | Ser<br>670 | Ser | |
| GAC | GAC | GAG | AAG | GAC | AAC | GAG | CCT | GCC | AAG | AAG | AAG | AGC | AAG | CCC | CCA | 2183 |
| Asp | Asp | Glu | Lys<br>675 | Asp | Asn | Glu | Pro | Ala | Lys<br>680 | Lys | Lys | Ser | Lys<br>685 | Pro | Pro | |
| TCC | GAC | GGC | GAT | GCC | AAG | AAG | AAA | AAG | GCC | AAG | AGC | GAG | AGC | GAA | CCG | 2231 |
| Ser | Asp | Gly<br>690 | Asp | Ala | Lys | Lys | Lys<br>695 | Lys | Ala | Lys | Ser | Glu<br>700 | Ser | Glu | Pro | |
| GAG | GAG | AGC | GAG | GAG | GAC | AGC | AAT | GCC | AGC | GAT | GAG | GAT | GAG | GAA | GAT | 2279 |
| Glu | Glu<br>705 | Ser | Glu | Glu | Asp | Ser<br>710 | Asn | Ala | Ser | Asp | Glu<br>715 | Asp | Glu | Glu | Asp | |
| GAG | GCC | AGT | GAT | TAGGGCCATA | AACACAACAA | ATCAATTCCA | TAAACACACA | | | | | | | | | 2331 |
| Glu | Ala | Ser | Asp<br>720 | | | | | | | | | | | | | |
| CCACGCTCCT | CACACACCCA | TGTCCCAAAT | CTAGTTTACA | TTCGCCGGAA | TTC | | | | | | | | | | | 2384 |

( 2 ) INFORMATION FOR SEQ ID NO:11:
        1:

( i ) SEQUENCE CHARACTERISTICS:
        ( A ) LENGTH: 723 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Drosophila melanogaster ( v i i ) IMMEDIATE SOURCE:
        ( B ) CLONE: Drosophila SSRP (predicted)

( i x ) FEATURE:
        ( A ) NAME/KEY: Domain
        ( B ) LOCATION: 458..507
        ( D ) OTHER INFORMATION: /label=Acidic ( i x ) FEATURE:
        ( A ) NAME/KEY: Domain
        ( B ) LOCATION: 518..547
        ( D ) OTHER INFORMATION: /label=Basic I ( i x ) FEATURE:
        ( A ) NAME/KEY: Domain
        ( B ) LOCATION: 547..620
        ( D ) OTHER INFORMATION: /label=HMG-box ( i x ) FEATURE:
        ( A ) NAME/KEY: Domain
        ( B ) LOCATION: 632..649
        ( D ) OTHER INFORMATION: /label=Basic II ( i x ) FEATURE:
        ( A ) NAME/KEY: Domain
        ( B ) LOCATION: 657..723
        ( D ) OTHER INFORMATION: /label=Mixed Charge ( x i ) SEQUENCE DESCRIPTION: SEQ ID NO:11:

| Met | Thr | Asp | Ser | Leu | Glu | Tyr | Asn | Asp | Ile | Asn | Ala | Glu | Val | Arg | Gly |
|---|---|---|---|---|---|---|---|---|---|---|---|---|---|---|---|
| 1 | | | | 5 | | | | | 10 | | | | | 15 | |

| | | | | | | | | | | | | | |
|---|---|---|---|---|---|---|---|---|---|---|---|---|---|
| Val | Leu | Cys | Ser 20 | Gly | Arg | Leu | Lys | Met 25 | Thr | Glu | Gln | Asn | Ile Ile Phe 30 |
| Lys | Asn | Thr 35 | Lys | Thr | Gly | Lys | Val 40 | Glu | Gln | Ile | Ser | Ala 45 | Glu Asp Ile |
| Asp | Leu 50 | Ile | Asn | Ser | Gln | Lys 55 | Phe | Val | Gly | Thr | Trp 60 | Gly | Leu Arg Val |
| Phe 65 | Thr | Lys | Gly | Gly 70 | Val | Leu | His | Arg | Phe | Thr 75 | Gly | Phe | Arg Asp Ser 80 |
| Glu | His | Glu | Lys | Leu 85 | Gly | Lys | Phe | Ile | Lys 90 | Ala | Ala | Tyr | Ser Gln Glu 95 |
| Met | Val | Glu | Lys 100 | Glu | Met | Cys | Val | Lys 105 | Gly | Trp | Asn | Trp | Gly Thr Ala 110 |
| Arg | Phe | Met 115 | Gly | Ser | Val | Leu | Ser 120 | Phe | Asp | Lys | Glu | Ser 125 | Lys Thr Ile |
| Phe | Glu 130 | Val | Pro | Leu | Ser | His 135 | Val | Ser | Gln | Cys | Val 140 | Thr | Gly Lys Asn |
| Glu 145 | Val | Thr | Leu | Glu | Phe 150 | His | Gln | Asn | Asp | Ala 155 | Pro | Val | Gly Leu 160 |
| Leu | Glu | Met | Arg | Phe 165 | His | Ile | Pro | Ala | Val 170 | Glu | Ser | Ala | Glu Asp 175 |
| Pro | Val | Asp | Lys 180 | Phe | His | Gln | Asn | Val 185 | Met | Ser | Lys | Ala | Ser Val Ile 190 |
| Ser | Ala | Ser 195 | Gly | Glu | Ser | Ile | Ala 200 | Ile | Phe | Arg | Glu | Ile 205 | Gln Ile Leu |
| Thr | Pro 210 | Arg | Gly | Arg | Tyr | Asp 215 | Ile | Lys | Ile | Phe | Ser 220 | Thr | Phe Phe Gln |
| Leu 225 | His | Gly | Lys | Thr | Phe 230 | Asp | Tyr | Lys | Ile | Pro 235 | Met | Asp | Ser Val Leu 240 |
| Arg | Leu | Phe | Met | Leu 245 | Pro | His | Lys | Asp | Ser 250 | Arg | Gln | Met | Phe Phe Val 255 |
| Leu | Ser | Leu | Asp 260 | Pro | Pro | Ile | Lys | Gln 265 | Gly | Gln | Thr | Arg | Tyr His Tyr 270 |
| Leu | Val | Leu | Leu 275 | Phe | Ala | Pro | Asp 280 | Glu | Glu | Thr | Thr | Ile 285 | Glu Leu Pro |
| Phe | Ser 290 | Glu | Ala | Glu | Leu | Arg 295 | Asp | Lys | Tyr | Glu | Gly 300 | Lys | Leu Glu Lys |
| Glu 305 | Ile | Ser | Gly | Pro | Val 310 | Tyr | Glu | Val | Met | Gly 315 | Lys | Val | Met Lys Val 320 |
| Leu | Ile | Gly | Arg | Lys 325 | Ile | Thr | Gly | Pro | Gly 330 | Asn | Phe | Ile | Gly His Ser 335 |
| Gly | Thr | Ala | Ala 340 | Val | Gly | Cys | Ser | Phe 345 | Lys | Ala | Ala | Ala | Gly Tyr Leu 350 |
| Tyr | Pro | Leu 355 | Glu | Arg | Gly | Phe | Ile 360 | Tyr | Ile | His | Lys | Pro 365 | Pro Leu His |
| Ile | Arg 370 | Phe | Glu | Glu | Ile | Ser 375 | Ser | Val | Asn | Phe | Ala 380 | Arg | Ser Gly Gly |
| Ser 385 | Thr | Arg | Ser | Phe | Asp 390 | Phe | Glu | Val | Thr | Leu 395 | Lys | Asn | Gly Thr Val 400 |
| His | Ile | Phe | Ser | Ser 405 | Ile | Glu | Lys | Glu 410 | Glu | Tyr | Ala | Lys | Leu Phe Asp 415 |
| Tyr | Ile | Thr | Gln 420 | Lys | Lys | Leu | His | Val 425 | Ser | Asn | Met | Gly | Lys Asp Lys 430 |
| Ser | Gly | Tyr 435 | Lys | Asp | Val | Asp | Phe 440 | Gly | Asp | Ser | Asp | Asn 445 | Glu Asn Glu |

```
        Pro Asp Ala Tyr Leu Ala Arg Leu Lys Ala Glu Ala Arg Glu Lys Glu
        450             455                 460

Glu Asp Asp Asp Asp Gly Asp Ser Asp Glu Glu Ser Thr Asp Glu Asp
        465                 470                 475                 480

Phe Lys Pro Asn Glu Asn Glu Ser Asp Val Ala Glu Glu Tyr Asp Ser
                        485                 490                 495

Asn Val Glu Ser Asp Ser Asp Asp Asp Ser Asp Ala Ser Gly Gly Gly
                        500                 505                 510

Gly Asp Ser Asp Gly Ala Lys Lys Lys Glu Lys Lys Ser Glu Lys
                    515                 520                 525

Lys Glu Lys Lys Glu Lys Lys His Lys Glu Lys Glu Arg Thr Lys Lys
                530                 535                 540

Pro Ser Lys Lys Lys Lys Asp Ser Gly Lys Pro Lys Arg Ala Thr Thr
        545                 550                 555                 560

Ala Phe Met Leu Trp Leu Asn Asp Thr Arg Glu Ser Ile Lys Arg Glu
                        565                 570                 575

Asn Pro Gly Ile Lys Val Thr Glu Ile Ala Lys Lys Gly Gly Glu Met
                        580                 585                 590

Trp Lys Glu Leu Lys Asp Lys Ser Lys Trp Glu Asp Ala Ala Ala Lys
                    595                 600                 605

Asp Lys Gln Arg Tyr His Asp Glu Met Arg Asn Tyr Lys Pro Glu Ala
            610                 615                 620

Gly Gly Asp Ser Asp Asn Glu Lys Gly Gly Lys Ser Ser Lys Lys Arg
        625                 630                 635                 640

Lys Thr Glu Pro Ser Pro Ser Lys Lys Ala Asn Thr Ser Gly Ser Gly
                        645                 650                 655

Phe Lys Ser Lys Glu Tyr Ile Ser Asp Asp Ser Thr Ser Ser Asp
                    660                 665                 670

Asp Glu Lys Asp Asn Glu Pro Ala Lys Lys Ser Lys Pro Pro Ser
            675                 680                 685

Asp Gly Asp Ala Lys Lys Lys Lys Ala Lys Ser Glu Ser Glu Pro Glu
                690                 695                 700

Glu Ser Glu Glu Asp Ser Asn Ala Ser Asp Glu Asp Glu Glu Asp Glu
        705                 710                 715                 720

Ala Ser Asp
```

( 2 ) INFORMATION FOR SEQ ID NO:12:

( i ) SEQUENCE CHARACTERISTICS:
     ( A ) LENGTH: 3292 base pairs
     ( B ) TYPE: nucleic acid
     ( C ) STRANDEDNESS: double
     ( D ) TOPOLOGY: linear ( i i ) MOLECULE TYPE: DNA (genomic)

( v i ) ORIGINAL SOURCE:
     ( A ) ORGANISM: Saccharomyces cerevisiae ( v i i ) IMMEDIATE SOURCE:
     ( B ) CLONE: lambda yPt ( i x ) FEATURE:
     ( A ) NAME/KEY: CDS
     ( B ) LOCATION: 1..1626

( x i ) SEQUENCE DESCRIPTION: SEQ ID NO:12:

```
GAA TTC GGG TTT CAA GCC CAG CCT CAA CAA CAA CAA CAG CAG CAG CAG      48
Glu Phe Gly Phe Gln Ala Gln Pro Gln Gln Gln Gln Gln Gln Gln Gln
 1               5                  10                  15

CAA CAA CAG CAA CAA CAA CAA GCG CCT TAT CAA GGT CAC TTC CAG CAG      96
Gln Gln Gln Gln Gln Gln Gln Ala Pro Tyr Gln Gly His Phe Gln Gln
```

|  |  |  |  |  |  |  |  |  |  |  |  |  |  |  |  |
|---|---|---|---|---|---|---|---|---|---|---|---|---|---|---|---|
| TCG | CCT | CAA | CAA | CAA | CAG | CAA | AAT | GTT | TAT | TTT | CCA | CTA | CCT | CCA | CAA | 144 |
| Ser | Pro | Gln | Gln | Gln | Gln | Gln | Asn | Val | Tyr | Phe | Pro | Leu | Pro | Pro | Gln |
|  |  | 35 |  |  |  |  | 40 |  |  |  |  | 45 |  |  |  |

| TCT | TTG | ACG | CAA | CCT | ACT | TCG | CAG | TCG | CAA | CAA | CAA | CAA | CAG | TAT | 192 |
| Ser | Leu | Thr | Gln | Pro | Thr | Ser | Gln | Ser | Gln | Gln | Gln | Gln | Gln | Tyr |
|  | 50 |  |  |  |  | 55 |  |  |  |  | 60 |  |  |  |

| GCT | AAT | TCG | AAC | TCA | AAT | TCA | AAC | AAC | AAT | GTT | AAT | GTT | AAC | GCG | CTA | 240 |
| Ala | Asn | Ser | Asn | Ser | Asn | Ser | Asn | Asn | Asn | Val | Asn | Val | Asn | Ala | Leu |
| 65 |  |  |  |  | 70 |  |  |  |  | 75 |  |  |  |  | 80 |

| CCT | CAG | GAT | TTC | GGT | TAC | ATG | CAA | CAA | ACC | GGA | TCG | GGC | CAA | AAC | TAT | 288 |
| Pro | Gln | Asp | Phe | Gly | Tyr | Met | Gln | Gln | Thr | Gly | Ser | Gly | Gln | Asn | Tyr |
|  |  |  |  | 85 |  |  |  |  | 90 |  |  |  |  | 95 |  |

| CCG | ACG | ATC | AAT | CAA | CAA | CAA | TTT | TCC | GAG | TTT | TAC | AAC | TCC | TTT | TTA | 336 |
| Pro | Thr | Ile | Asn | Gln | Gln | Gln | Phe | Ser | Glu | Phe | Tyr | Asn | Ser | Phe | Leu |
|  |  |  | 100 |  |  |  |  | 105 |  |  |  |  | 110 |  |  |

| AGT | CAT | TTA | ACT | CAA | AAA | CAG | ACA | AAC | CCT | TCT | GTC | ACG | GGT | ACA | GGC | 384 |
| Ser | His | Leu | Thr | Gln | Lys | Gln | Thr | Asn | Pro | Ser | Val | Thr | Gly | Thr | Gly |
|  |  | 115 |  |  |  |  | 120 |  |  |  |  | 125 |  |  |  |

| GCG | TCT | AGT | AAC | AAC | AAC | AGT | AAC | AAC | AAC | AAT | GTT | AGT | AGC | GGC | AAT | 432 |
| Ala | Ser | Ser | Asn | Asn | Asn | Ser | Asn | Asn | Asn | Asn | Val | Ser | Ser | Gly | Asn |
|  | 130 |  |  |  |  | 135 |  |  |  |  | 140 |  |  |  |  |

| AAC | AGC | ACT | AGC | AGT | AAT | CCT | ACC | CAG | CTG | GCA | GCC | TCC | CAA | TTA | AAC | 480 |
| Asn | Ser | Thr | Ser | Ser | Asn | Pro | Thr | Gln | Leu | Ala | Ala | Ser | Gln | Leu | Asn |
| 145 |  |  |  |  | 150 |  |  |  |  | 155 |  |  |  |  | 160 |

| CCT | GCC | ACG | GCT | ACT | ACG | GCC | GCC | GCA | AAC | AAT | GCT | GCT | GGC | CCG | GCT | 528 |
| Pro | Ala | Thr | Ala | Thr | Thr | Ala | Ala | Ala | Asn | Asn | Ala | Ala | Gly | Pro | Ala |
|  |  |  |  | 165 |  |  |  |  | 170 |  |  |  |  | 175 |  |

| TCG | TAC | TTG | TCT | CAG | CTC | CCA | CAG | GTG | CAG | AGA | TAC | TAC | CCG | AAC | AAC | 576 |
| Ser | Tyr | Leu | Ser | Gln | Leu | Pro | Gln | Val | Gln | Arg | Tyr | Tyr | Pro | Asn | Asn |
|  |  |  | 180 |  |  |  |  | 185 |  |  |  |  | 190 |  |  |

| ATG | AAC | GCT | CTG | TCT | AGT | CTT | TTG | GAC | CCT | TCC | TCT | GCA | GGA | AAT | GCT | 624 |
| Met | Asn | Ala | Leu | Ser | Ser | Leu | Leu | Asp | Pro | Ser | Ser | Ala | Gly | Asn | Ala |
|  |  | 195 |  |  |  |  | 200 |  |  |  |  | 205 |  |  |  |

| GCA | GGA | AAT | GCC | AAC | ACC | GCT | ACT | CAT | CCT | GGT | TTG | TTA | CCA | CCC | AAT | 672 |
| Ala | Gly | Asn | Ala | Asn | Thr | Ala | Thr | His | Pro | Gly | Leu | Leu | Pro | Pro | Asn |
| 210 |  |  |  |  | 215 |  |  |  |  | 220 |  |  |  |  |  |

| CTG | CAA | CCT | CAA | TTG | ACT | CAC | CAC | CAG | CAG | CAG | ATG | CAG | CAA | CAG | CTG | 720 |
| Leu | Gln | Pro | Gln | Leu | Thr | His | His | Gln | Gln | Gln | Met | Gln | Gln | Gln | Leu |
| 225 |  |  |  |  | 230 |  |  |  |  | 235 |  |  |  |  | 240 |

| CAA | TTA | CAA | CAA | CAA | CAG | CAG | TTG | CAG | CAA | CAG | CAG | CAG | CTA | CAA | CAG | 768 |
| Gln | Leu | Gln | Gln | Gln | Gln | Gln | Leu | Gln | Gln | Gln | Gln | Gln | Leu | Gln | Gln |
|  |  |  |  | 245 |  |  |  |  | 250 |  |  |  |  | 255 |  |

| CAA | CAC | CAG | TTG | CAA | CAA | CAA | CAA | CAA | CTT | CAA | CAA | CAA | CAT | CAT | CAT | 816 |
| Gln | His | Gln | Leu | Gln | Gln | Gln | Gln | Gln | Leu | Gln | Gln | Gln | His | His | His |
|  |  |  | 260 |  |  |  |  | 265 |  |  |  |  | 270 |  |  |

| CTA | CAA | CAG | CAA | CAG | CAG | CAA | CAA | CAG | CAT | CCA | GTG | GTG | AAG | AAA | TTA | 864 |
| Leu | Gln | Gln | Gln | Gln | Gln | Gln | Gln | Gln | His | Pro | Val | Val | Lys | Lys | Leu |
|  |  | 275 |  |  |  |  | 280 |  |  |  |  | 285 |  |  |  |

| TCT | TCC | ACT | CAA | AGC | AGA | ATT | GAG | AGA | AGA | AAA | CAA | CTG | AAA | AAG | CAA | 912 |
| Ser | Ser | Thr | Gln | Ser | Arg | Ile | Glu | Arg | Arg | Lys | Gln | Leu | Lys | Lys | Gln |
|  | 290 |  |  |  |  | 295 |  |  |  |  | 300 |  |  |  |  |

| GGC | CCA | AAG | AGA | CCT | TCT | TCC | GCT | TAT | TTC | CTG | TTT | TCT | ATG | TCC | ATA | 960 |
| Gly | Pro | Lys | Arg | Pro | Ser | Ser | Ala | Tyr | Phe | Leu | Phe | Ser | Met | Ser | Ile |
| 305 |  |  |  |  | 310 |  |  |  |  | 315 |  |  |  |  | 320 |

| AGA | AAT | GAG | TTG | CTT | CAA | CAA | TTC | CCT | GAA | GCA | AAG | GTC | CCC | GAA | TTG | 1008 |
| Arg | Asn | Glu | Leu | Leu | Gln | Gln | Phe | Pro | Glu | Ala | Lys | Val | Pro | Glu | Leu |
|  |  |  |  | 325 |  |  |  |  | 330 |  |  |  |  | 335 |  |

| TCT | AAA | TTG | GCT | TCT | GCA | AGG | TGG | AAA | GAG | TTA | ACG | GAT | GAT | CAA | AAA | 1056 |
| Ser | Lys | Leu | Ala | Ser | Ala | Arg | Trp | Lys | Glu | Leu | Thr | Asp | Asp | Gln | Lys |
|  |  |  | 340 |  |  |  |  | 345 |  |  |  |  | 350 |  |  |

| | | | | | | | | | | | | | | | |
|---|---|---|---|---|---|---|---|---|---|---|---|---|---|---|---|
|AAA|CCA|TTC|TAC|GAA|GAA|TTC|AGA|ACC|AAC|TGG|GAG|AAG|TAC|AGA|GTT|
|Lys|Pro|Phe|Tyr|Glu|Glu|Phe|Arg|Thr|Asn|Trp|Glu|Lys|Tyr|Arg|Val|
| |355| | | | |360| | | | |365| | | | |

1104

| | | | | | | | | | | | | | | | |
|---|---|---|---|---|---|---|---|---|---|---|---|---|---|---|---|
|GTG|AGA|GAT|GCT|TAC|GAA|AAG|ACT|TTG|CCC|CCA|AAG|AGA|CCC|TCT|GGT|
|Val|Arg|Asp|Ala|Tyr|Glu|Lys|Thr|Leu|Pro|Pro|Lys|Arg|Pro|Ser|Gly|
| |370| | | | |375| | | | |380| | | | |

1152

| | | | | | | | | | | | | | | | |
|---|---|---|---|---|---|---|---|---|---|---|---|---|---|---|---|
|CCC|TTT|ATT|CAG|TTC|ACC|CAG|GAG|ATT|AGA|CCT|ACC|GTC|GTC|AAG|GAA|
|Pro|Phe|Ile|Gln|Phe|Thr|Gln|Glu|Ile|Arg|Pro|Thr|Val|Val|Lys|Glu|
|385| | | | |390| | | | |395| | | | |400|

1200

| | | | | | | | | | | | | | | | |
|---|---|---|---|---|---|---|---|---|---|---|---|---|---|---|---|
|AAT|CCT|GAT|AAA|GGT|TTA|ATC|GAA|ATT|ACC|AAG|ATA|ATC|GGT|GAA|AGA|
|Asn|Pro|Asp|Lys|Gly|Leu|Ile|Glu|Ile|Thr|Lys|Ile|Ile|Gly|Glu|Arg|
| | | | |405| | | | |410| | | | |415| |

1248

| | | | | | | | | | | | | | | | |
|---|---|---|---|---|---|---|---|---|---|---|---|---|---|---|---|
|TGG|CGC|GAG|TTA|GAC|CCC|TGC|CAA|AAG|GCG|GAA|TAC|ACT|GAA|ACT|TAC|
|Trp|Arg|Glu|Leu|Asp|Pro|Cys|Gln|Lys|Ala|Glu|Tyr|Thr|Glu|Thr|Tyr|
| | | |420| | | | |425| | | | |430| | |

1296

| | | | | | | | | | | | | | | | |
|---|---|---|---|---|---|---|---|---|---|---|---|---|---|---|---|
|AAG|AAA|AGA|TTA|AAG|GAA|TGG|GAA|AGT|TGT|TAT|CCC|GAC|GAA|AAT|GAT|
|Lys|Lys|Arg|Leu|Lys|Glu|Trp|Glu|Ser|Cys|Tyr|Pro|Asp|Glu|Asn|Asp|
| | |435| | | | |440| | | | |445| | | |

1344

| | | | | | | | | | | | | | | | |
|---|---|---|---|---|---|---|---|---|---|---|---|---|---|---|---|
|CCA|AAC|GGT|AAC|CCA|ACC|GGT|CAC|TCA|CAT|AAG|GCC|ATG|AAC|ATG|AAT|
|Pro|Asn|Gly|Asn|Pro|Thr|Gly|His|Ser|His|Lys|Ala|Met|Asn|Met|Asn|
| | |450| | | | |455| | | | |460| | | |

1392

| | | | | | | | | | | | | | | | |
|---|---|---|---|---|---|---|---|---|---|---|---|---|---|---|---|
|TTG|AAT|ATG|GAC|ACT|AAA|ATC|ATG|GAG|AAC|CAA|GAC|AGT|ATC|GAG|CAC|
|Leu|Asn|Met|Asp|Thr|Lys|Ile|Met|Glu|Asn|Gln|Asp|Ser|Ile|Glu|His|
|465| | | | |470| | | | |475| | | | |480|

1440

| | | | | | | | | | | | | | | | |
|---|---|---|---|---|---|---|---|---|---|---|---|---|---|---|---|
|ATA|ACC|GCA|AAT|GCC|ATC|GAC|TCA|GTT|ACC|GGA|AGC|AAC|AGT|AAC|AGT|
|Ile|Thr|Ala|Asn|Ala|Ile|Asp|Ser|Val|Thr|Gly|Ser|Asn|Ser|Asn|Ser|
| | | | |485| | | | |490| | | | |495| |

1488

| | | | | | | | | | | | | | | | |
|---|---|---|---|---|---|---|---|---|---|---|---|---|---|---|---|
|ACC|ACC|CCA|AAT|ACG|CCC|GTT|TCT|CCT|CCG|ATT|TCA|TTA|CAG|CAG|CAG|
|Thr|Thr|Pro|Asn|Thr|Pro|Val|Ser|Pro|Pro|Ile|Ser|Leu|Gln|Gln|Gln|
| | | |500| | | | |505| | | | |510| | |

1536

| | | | | | | | | | | | | | | | |
|---|---|---|---|---|---|---|---|---|---|---|---|---|---|---|---|
|CCG|CTC|CAA|CAA|CAA|CAA|CAA|CAG|CAG|CAA|CAA|CAA|CAA|CAC|ATG|TTA|
|Pro|Leu|Gln|Gln|Gln|Gln|Gln|Gln|Gln|Gln|Gln|Gln|Gln|His|Met|Leu|
| | |515| | | | |520| | | | |525| | | |

1584

| | | | | | | | | | | | | |
|---|---|---|---|---|---|---|---|---|---|---|---|---|
|TTG|GCT|GAC|CCC|ACT|ACA|AAT|GGT|TCG|ATC|ATA|AAA|AAT|GAA|
|Leu|Ala|Asp|Pro|Thr|Thr|Asn|Gly|Ser|Ile|Ile|Lys|Asn|Glu|
| |530| | | | |535| | | | |540| | |

1626

| | | | | |
|---|---|---|---|---|
|TAACAAATAA|ACAACTTTAG|TTTTCCACTG|TAACATTATC|CGACGCAAAC AACGAGAATA|1686|
|AGGAATTCGA|ATTCCTTTTT|CAACATTTGT|TTAATATTGT|ACTACTCTAT TTCCTATTAC|1746|
|TACAAATTTT|ACTTTATTTA|ATAATAATTT|TTCTTTCCCT|TTTTCTAACT TCAGTCTATA|1806|
|TGTATTTGCC|TGTATACATA|TACGCATGTG|TGTAGTCTTC|CCTCCTTCTT GTTTTGTAA|1866|
|TATACTTAAG|CCAAATTCAA|GTTGCCTCT|GATGCTGTGC|GAGCTCAACT GACGAGCGTG|1926|
|ATGAAGCCAA|AAAAATTAAT|TGATTTCGCC|CAGATCGAAC|TGGGGATCTG CTGCGTGTTA|1986|
|AGCAGATCCA|TAGCGACTAG|ACCACGAAAC|CTATTAATCT|GTAAAATTGA TCATTTTAAA|2046|
|GTGGCATAGT|TGTACGATAC|ACAAGGGCGA|CTTATCAACT|TACACATAAA TATGTTTGAA|2106|
|ACATGTCAGA|AACACTCGTT|ACAAAGCAGA|CAAAATTTAT|TACATCAAAC GATACCCTGC|2166|
|CTAGACAAAC|CAGTTAAACG|TTGTAAATAC|CTGGACAACT|AGTTAGTTC CGAGATTCTG|2226|
|CGCTTCCATT|GAGTCTTATG|ACTGTTTCTC|AGTTTTCATG|TCATCTTTTG ACGCCGCATG|2286|
|GGATAATGTG|TACTAATAAC|ATAAATACTA|GTCAATAGAT|GATATTACGA TTCCATCCAC|2346|
|AAAGGTGAGG|TGCTAGTCAC|CACCTAAGGA|TATTAGATTG|TCAAGATGCC CGCTATTACT|2406|
|GGAGCCCTTA|GTATAACGGA|TATTTCAGG|ATAGCAGACT|TACTTCTCCA AGTGTAAGGG|2466|
|AACACCGAAT|CTAAAGTAGC|TACTGCTCCT|CCATTCCGTG|TATATAATCT TGCTTTTTTT|2526|
|TAGGAAAATA|CTAATACTCG|CATATATTGG|TTATTATCAT|TACTTGGACA CTGTCTGTTC|2586|
|TATCGCTTCA|TTTGTAATAT|GCGTATTGCC|CTTCTTATTA|ATTGGCTAAT ATTTCACCTG|2646|

| | | | | | |
|---|---|---|---|---|---|
| CAACATAGGT | CCCTGTTGAT | TAACGTGTTT | ATCCATTTCA | ATCATGAGAA | ATGTTTCTTC | 2706 |
| TGTTTTCCAA | TGCCTGGCCG | AGCTGGTAAT | ATATATATAT | ATATGTACAT | AATACTTTAT | 2766 |
| TAGATATATT | GTTGATGATT | AGTAGACAAG | TGGTACTACC | AACCGAGAAT | AAAAGCTGGT | 2826 |
| CTTCTTATAT | AATATGAGTA | TGGTATAAAT | AGCAGTCACC | GATATCATTG | GTTACCCAAA | 2886 |
| GTGACAATTC | ATGTCTTTCA | TAGATATAAA | TCGTAAGCTA | AAATTGAATT | AAAAGATCTT | 2946 |
| TAATTTAGCT | GCCCTGCTAA | TCTGAAGTCA | CATATCATTC | CTCATTCTGG | ATCACTCACA | 3006 |
| ACATTTATTG | TCTAATAACT | TATGTAATCA | CTATAGTCAC | TGGTGTGAAC | AATGTGAGCA | 3066 |
| ATAATAAACC | ACTGTATTAC | CATATACAAA | TGCATATGTT | TAGCCACATA | AGTTTAATTT | 3126 |
| ATATTTCTTA | TTTTCCACAC | GATATCCCCA | CTATCAATGA | CATAGATGAT | ATTTTCTCCA | 3186 |
| CTGGAACAAC | CTGAATACAA | CAATATATTA | TTTGTTCAAG | TACCGCTTCA | GAAATTAAAT | 3246 |
| ACTCTGTAAT | TTTGACCCCT | TCTAGCACCA | TATGTACCCC | GAATTC | | 3292 |

( 2 ) INFORMATION FOR SEQ ID NO:13:

( i ) SEQUENCE CHARACTERISTICS:
  ( A ) LENGTH: 542 amino acids
  ( B ) TYPE: amino acid
  ( D ) TOPOLOGY: linear ( i i ) MOLECULE TYPE: peptide ( v i ) ORIGINAL SOURCE:
  ( A ) ORGANISM: Saccharomyces cerevisiae ( v i i ) IMMEDIATE SOURCE:
  ( B ) CLONE: fractional yeast SSRP (fySSRP) (predicted)

( x i ) SEQUENCE DESCRIPTION: SEQ ID NO:13:

```
Glu Phe Gly Phe Gln Ala Gln Pro Gln Gln Gln Gln Gln Gln Gln
 1               5                  10                  15

Gln Gln Gln Gln Gln Gln Gln Ala Pro Tyr Gln Gly His Phe Gln Gln
            20                  25                  30

Ser Pro Gln Gln Gln Gln Gln Asn Val Tyr Phe Pro Leu Pro Pro Gln
            35                  40                  45

Ser Leu Thr Gln Pro Thr Ser Gln Ser Gln Gln Gln Gln Gln Gln Tyr
        50                  55                  60

Ala Asn Ser Asn Ser Asn Ser Asn Asn Asn Val Asn Val Asn Ala Leu
65                  70                  75                  80

Pro Gln Asp Phe Gly Tyr Met Gln Gln Thr Gly Ser Gly Gln Asn Tyr
                85                  90                  95

Pro Thr Ile Asn Gln Gln Gln Phe Ser Glu Phe Tyr Asn Ser Phe Leu
            100                 105                 110

Ser His Leu Thr Gln Lys Gln Thr Asn Pro Ser Val Thr Gly Thr Gly
        115                 120                 125

Ala Ser Ser Asn Asn Asn Ser Asn Asn Asn Asn Val Ser Ser Gly Asn
    130                 135                 140

Asn Ser Thr Ser Ser Asn Pro Thr Gln Leu Ala Ala Ser Gln Leu Asn
145                 150                 155                 160

Pro Ala Thr Ala Thr Thr Ala Ala Ala Asn Asn Ala Ala Gly Pro Ala
                165                 170                 175

Ser Tyr Leu Ser Gln Leu Pro Gln Val Gln Arg Tyr Tyr Pro Asn Asn
            180                 185                 190

Met Asn Ala Leu Ser Ser Leu Leu Asp Pro Ser Ser Ala Gly Asn Ala
        195                 200                 205

Ala Gly Asn Ala Asn Thr Ala Thr His Pro Gly Leu Leu Pro Pro Asn
    210                 215                 220
```

| | | | | | | | | | | | | | |
|---|---|---|---|---|---|---|---|---|---|---|---|---|---|
| Leu 225 | Gln | Pro | Gln | Leu | Thr 230 | His | His | Gln | Gln 235 | Met | Gln | Gln | Leu 240 |
| Gln | Leu | Gln | Gln | Gln 245 | Gln | Gln | Leu | Gln | Gln 250 | Gln | Gln | Leu | Gln 255 | Gln |
| Gln | His | Gln | Leu 260 | Gln | Gln | Gln | Gln 265 | Leu | Gln | Gln | Gln | His 270 | His | His |
| Leu | Gln | Gln 275 | Gln | Gln | Gln | Gln | Gln 280 | Gln | His | Pro | Val | Val 285 | Lys | Lys | Leu |
| Ser | Ser 290 | Thr | Gln | Ser | Arg | Ile 295 | Glu | Arg | Arg | Lys | Gln 300 | Leu | Lys | Lys | Gln |
| Gly 305 | Pro | Lys | Arg | Pro | Ser 310 | Ser | Ala | Tyr | Phe | Leu 315 | Phe | Ser | Met | Ser | Ile 320 |
| Arg | Asn | Glu | Leu | Leu 325 | Gln | Gln | Phe | Pro | Glu 330 | Ala | Lys | Val | Pro | Glu 335 | Leu |
| Ser | Lys | Leu | Ala 340 | Ser | Ala | Arg | Trp | Lys 345 | Glu | Leu | Thr | Asp 350 | Asp | Gln | Lys |
| Lys | Pro | Phe 355 | Tyr | Glu | Glu | Phe | Arg 360 | Thr | Asn | Trp | Glu | Lys 365 | Tyr | Arg | Val |
| Val | Arg 370 | Asp | Ala | Tyr | Glu | Lys 375 | Thr | Leu | Pro | Pro | Lys 380 | Arg | Pro | Ser | Gly |
| Pro 385 | Phe | Ile | Gln | Phe | Thr 390 | Gln | Glu | Ile | Arg | Pro 395 | Thr | Val | Val | Lys | Glu 400 |
| Asn | Pro | Asp | Lys | Gly 405 | Leu | Ile | Glu | Ile | Thr 410 | Lys | Ile | Ile | Gly | Glu 415 | Arg |
| Trp | Arg | Glu | Leu 420 | Asp | Pro | Ala | Lys | Lys 425 | Ala | Glu | Tyr | Thr | Glu 430 | Thr | Tyr |
| Lys | Lys | Arg 435 | Leu | Lys | Glu | Trp | Glu 440 | Ser | Cys | Tyr | Pro | Asp 445 | Glu | Asn | Asp |
| Pro | Asn 450 | Gly | Asn | Pro | Thr | Gly 455 | His | Ser | His | Lys | Ala 460 | Met | Asn | Met | Asn |
| Leu 465 | Asn | Met | Asp | Thr | Lys 470 | Ile | Met | Glu | Asn | Gln 475 | Asp | Ser | Ile | Glu | His 480 |
| Ile | Thr | Ala | Asn | Ala 485 | Ile | Asp | Ser | Val | Thr 490 | Gly | Ser | Asn | Ser | Asn 495 | Ser |
| Thr | Asn | Pro | Asn 500 | Thr | Pro | Val | Ser | Pro 505 | Pro | Ile | Ser | Leu | Gln 510 | Gln | Gln |
| Pro | Leu | Gln 515 | Gln | Gln | Gln | Gln | Gln 520 | Gln | Gln | Gln | Gln | Gln 525 | His | Met | Leu |
| Leu | Ala 530 | Asp | Pro | Thr | Thr | Asn 535 | Gly | Ser | Ile | Ile | Lys 540 | Asn | Glu |